US012582709B2

(12) United States Patent
Hartigan-O'Connor

(10) Patent No.: US 12,582,709 B2
(45) Date of Patent: Mar. 24, 2026

(54) PERSISTENT MEMORY T-CELL RESPONSES TO CANCER AND INFECTIOUS-DISEASE ANTIGENS BY MANIPULATION OF AMINO ACID-CATABOLISM PATHWAYS

(71) Applicant: THE REGENTS OF THE UNIVERSITY OF CALIFORNIA, Oakland, CA (US)

(72) Inventor: Dennis Hartigan-O'Connor, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 495 days.

(21) Appl. No.: 18/013,863

(22) PCT Filed: Jul. 1, 2021

(86) PCT No.: PCT/US2021/040132
§ 371 (c)(1),
(2) Date: Dec. 29, 2022

(87) PCT Pub. No.: WO2022/006424
PCT Pub. Date: Jan. 6, 2022

(65) Prior Publication Data
US 2023/0173056 A1     Jun. 8, 2023

Related U.S. Application Data

(60) Provisional application No. 63/047,737, filed on Jul. 2, 2020.

(51) Int. Cl.
| | |
|---|---|
| *C12Q 1/68* | (2018.01) |
| *A61K 39/21* | (2006.01) |
| *A61K 39/215* | (2006.01) |
| *A61P 31/14* | (2006.01) |
| *A61P 31/18* | (2006.01) |
| *A61P 37/04* | (2006.01) |
| *C07K 14/005* | (2006.01) |
| *C12N 9/78* | (2006.01) |
| *C12N 9/96* | (2006.01) |
| *C12N 15/00* | (2006.01) |
| *C12N 15/64* | (2006.01) |
| *C12N 15/66* | (2006.01) |
| *C12N 15/86* | (2006.01) |

(52) U.S. Cl.
CPC ............ *A61K 39/21* (2013.01); *A61K 39/215* (2013.01); *A61P 31/14* (2018.01); *A61P 31/18* (2018.01); *A61P 37/04* (2018.01); *C07K 14/005* (2013.01); *C12N 9/78* (2013.01); *C12N 15/86* (2013.01); *C12Y 305/03001* (2013.01); *C12N 2740/15034* (2013.01); *C12N 2740/15071* (2013.01); *C12N 2740/16234* (2013.01); *C12N 2740/16271* (2013.01); *C12N*

*2750/14143* (2013.01); *C12N 2750/14171* (2013.01); *C12N 2770/20034* (2013.01); *C12N 2770/20071* (2013.01)

(58) Field of Classification Search
CPC ........ C12N 15/10; C12N 15/64; C12N 15/66; C12N 2800/70; C12N 2810/50
See application file for complete search history.

(56) References Cited

U.S. PATENT DOCUMENTS

| | | |
|---|---|---|
| 4,795,805 A | 1/1989 | Itoh et al. |
| 2002/0055159 A1 | 5/2002 | Meyers |
| 2013/0022640 A1 | 1/2013 | Hurwitz et al. |
| 2017/0049868 A1 | 2/2017 | Andersen et al. |
| 2018/0038852 A1 | 2/2018 | Manuguerra et al. |
| 2018/0280451 A9 | 10/2018 | Falb et al. |

FOREIGN PATENT DOCUMENTS

| | | |
|---|---|---|
| WO | 2007081878 A2 | 7/2007 |
| WO | 20091 43843 A1 | 12/2009 |

OTHER PUBLICATIONS

Andersen , "The Specific Targeting of Immune Regulation: T-cell Responses Against Indoleamine 2,3-Dioxygenase", Cancer Immunology, Immunotherapy, vol. 61, No. 8, XP035088700, Mar. 3, 2012, pp. 1289-1297.
Bogdan , "Nitric Oxide Synthase in Innate and Adaptive Immunity: an Update", Trends in Immunology, vol. 36, No. 3, XP093223270, Mar. 1, 2015, pp. 161-178.
EP21833472.0 , "Partial Supplementary European Search Report", Jul. 8, 2024, 16 pages.
EP21833472.0 , "Extended European Search Report", Nov. 22, 2024, 22 pages.
Lee et al., "Restoring Ureagenesis in Hepatocytes by CRISPR/Cas9-mediated Genomic Addition to Arginase-deficient Induced Pluripotent Stem Cells", Molecular Therapy-Nucleic Acids, vol. 5, XP055971281, Jan. 1, 2016, pp. 1-14.

(Continued)

*Primary Examiner* — Barry A Chestnut
(74) *Attorney, Agent, or Firm* — Kilpatrick Townsend & Stockton LLP

(57) ABSTRACT

Provided herein are recombinant polynucleotides including a first nucleic acid sequence encoding an antigen, and a second nucleic acid sequence encoding an enzyme of an amino acid catabolic pathway. The provided recombinant polynucleotides are particularly useful for inducing long-lived immune responses having improved memory characteristics. Also provided are pharmaceutical compositions, viral particles, and host cells including the disclosed recombinant polynucleotides, and methods for using the disclosed materials.

19 Claims, 10 Drawing Sheets
Specification includes a Sequence Listing.

(56)                References Cited

OTHER PUBLICATIONS

Martinenaite et al., "Arginase-1-Based Vaccination Against the Tumor Microenvironment: The Identification of an Optimal T-cell Epitope", Cancer Immunology Immunotherapy, XP055640909, Nov. 6, 2019, 7 pages.

Nathan , "Perspectives Series: Nitric Oxide and Nitric Oxide Synthases Inducible Nitric Oxide Synthase: What Difference Does It Make?", Journal of Clinical Investigation, vol. 100, No. 10, XP093223376, Nov. 1, 1997, pp. 2417-2423.

Qiu , "Construction and Identification of Polycistron Adenoviral Expression Vector PCA13/FasL-IRES-iNOS", Chines Journal of Digestive Diseases, vol. 5, No. 1, XP093223364, Feb. 1, 2004, pp. 40-43.

Rath et al., "Metabolism via Arginase or Nitric Oxide Synthase: Two Competing Arginine Pathways in Macrophages", Frontiers in Immunology, vol. 5, XP093219680, Oct. 27, 2014, pp. 1-10.

Sorensen et al., "Indoleamine 2,3-Dioxygenase Specific, Cytotoxic T Cells as Immune Regulators", Blood, vol. 117, No. 7, XP093176559, Feb. 17, 2011, pp. 2200-2210.

Invitation to Pay Additional Fees and, Where Applicable, Protest Fee, mailed Oct. 12, 2021, for International Patent Application No. PCT/US2021/040132, 3 pages.

International Search Report and Written Opinion, mailed Jan. 6, 2022, for International Patent Application No. PCT/US2021/040132, 12 pages.

International Preliminary Report on Patentability, mailed Jan. 12, 2023, for International Patent Application No. PCT/US2021/040132, 8 pages.

Murray, "Amino Acid Auxotrophy as a System of Immunological Control Nodes", Nature Immunology, vol. 17, No. 2, Feb. 2016, pp. 132-139.

Sage et al., "Indoleamine 2,3-Dioxygenase (IDO) Activity During the Primary Immune Response to Influenza Infection Modifies the Memory T Cell Response to Influenza Challenge", Viral Immunology, vol. 27, Issue 3, Apr. 2014, pp. 112-123.

Sanchez, "Targeted Extracellular Delivery of Indoleamine 2,3 Dioxygenase via Fusion with Galectin 3", PhD Dissertation, Dec. 2017, pp. 1-7.

Sudowe S, Höhn Y, Renzing A, Maxeiner J, Montermann E, Habermeier A, Closs E, Bros M, Reske-Kunz AB. Inhibition of antigen-specific immune responses by co-application of an indoleamine 2,3-dioxygenase (IDO)-encoding vector requires antigen transgene expression focused on dendritic cells. Amino Acids. Mar. 2020;52(3):411-424. doi: 10.1007/s00726-020-02817-4. Epub Feb. 1, 2020. PMID: 32008091.

Codon optimized SIVgagNF-IRES-IDO1 cassette
4801 bp codon optimized SARSCoV2N-IRES-IDO1 cassette
4526 bp codon optimized SARSCoV2S1-IRES-IDO1 cassette
5339 bp codon optimized SIVgagNF-IRES-ARG1 cassette
4558 bp

PERSISTENT MEMORY T-CELL RESPONSES TO CANCER AND INFECTIOUS-DISEASE ANTIGENS BY MANIPULATION OF AMINO ACID-CATABOLISM PATHWAYS

CROSS-REFERENCE TO RELATED APPLICATIONS

The present application is a § 371 National Phase Application of International Patent Application No. PCT/US2021/040132 filed Jul. 1, 2021, which claims priority to U.S. Provisional Application No. 63/047,737 filed Jul. 2, 2020, the full disclosures of which are incorporated by reference in their entirety for all purposes.

STATEMENT AS TO RIGHTS TO INVENTIONS MADE UNDER FEDERALLY SPONSORED RESEARCH AND DEVELOPMENT

This invention was made with government support under Grant No. R01-AI143554 awarded by the National Institute of Allergy and Infectious Diseases. The government has certain rights in the invention.

BACKGROUND

The adaptive immune system reacts to infectious threats by production of two cell types in waves. The first and most urgent response consists of "effector" cells that function to fight an ongoing threat. Effector T cells are localized to infected tissues and help to control infection by killing infected cells, whereas effector B cells are short-lived plasmablasts that secrete antibodies. The second important facet of adaptive immunity is production of long-lived memory T and B cells. These memory cells contribute minimally or not at all to clearance of an ongoing infection. Instead, memory cells stand ready to proliferate and respond after subsequent pathogenic exposure. On second exposure, these "memory" cells respond by proliferating and differentiating quickly into new effector cells that can fight the infection in real time. The purpose of vaccination is to create long-lived memory cells without also introducing the danger of primary exposure to a pathogen. In an immune response to vaccination, therefore, the first wave of adaptive immunity—effector cell production—is superfluous except to the extent that an effector response may be required to generate memory. Indeed, effector and memory responses are in tension: inflammatory responses associated with infection promote effector-cell differentiation and inhibit memory-cell differentiation, while certain "regulatory" functions, which mediate the transition from effector to memory phases, are inhibitory to effectors and required for memory cells. Unfortunately, many vaccine candidates provoke relatively short-lived responses that are not protective over a span of years, as would be desirable.

As an example, the waning effectiveness of influenza vaccine has been reported from a number of surveillance studies in Europe and Australia (S. G. Sullivan et al., 86 J. Med. Virol. 1017 (2014); A. Zhang et al., 18 Euro. Surveill. 20657 (2013)). Protective immune response to the standard inactivated influenza vaccine consists of antibodies to surface haemagglutinin (S. E. Ohmit, J. G. Petrie, R. T. Cross, E. Johnson & A. S. Monto, 204 J. Infect. Dis. 1879 (2011)). Currently, age-specific immunogenicity criteria based on the hemagglutination inhibition (HI) titer are used by the Federal Drug Administration (L. Wijnans & B. Voordouw, 10 Influenza Other Respir. Viruses 2 (2016)). An HI titer of 1:40 is considered seroprotective, and more than 70% of younger adults or 60% of older adults must reach this threshold for licensing.

One study carried out in Spain, however, reported that vaccine effectiveness declined from 61% in the first 100 days after vaccination to 42% between days 100-119, and then to 0% after 120 days. This decline in effectiveness was most significant in people over 65 years of age. These results are paralleled by studies of antibody persistence after influenza infection. An observational study monitored titer trajectories in unvaccinated subjects who were assessed to be infected with influenza A/H1N1 during the 2009 pandemic (J. P. Hsu et al., 14 BMC Infect. Dis. 414 (2014)). In 71% of subjects, HI titers were >1:40 immediately after the epidemic peak. The prevalence of a protective titer declined to 25% of subjects at 6 months, and to only 14% one year after the pandemic. In a sub-group analysis of elderly subjects in the cohort, the rate of antibody decline was significantly faster.

Such waning antibody responses to vaccinations can lead to increased risk of infection if the time between vaccination and influenza exposure is long. In the United States, most influenza vaccination typically occurs between September and November each year; however, the vaccine may be available as early as July in some locations. Influenza activity typically peaks between December and February each year, but circulation can continue into the late spring (A. S. Monto, 26 Vaccine Suppl. 4 D45 (2008). Thus, long periods of time may elapse between vaccination and potential exposure, which could result in reduced protection.

Immunoprotective effector T cells are important for immediate pathogen control but are normally short lived, whereas the memory population can self-renew and is critical for the recall responses desired for vaccines. These different fates of effector vs. memory T-cells are thought to represent alternative differentiation pathways for a common set of precursors (J. A. Olson & S. C. Jameson, 35 Immunity 663 (2011) and thus the two fates are in tension. A vaccine designed to maximize memory-cell differentiation will likely also inhibit effector-cell differentiation.

T-cell responses, e.g., responses to vaccines, are not monolithic but rather reflect a mixture of responding cells with different phenotypes and functional capacities. CD4⁺ T cells generally react to peptides originating extracellularly or in sub-cellular compartments, which are processed and presented on class-II MHC molecules, while CD8⁺ T cells generally react to peptides originating intracellularly, e.g., in the cytoplasm, that are presented on class-I MHC molecules. The responding cells may producing varying numbers and kinds of cytokines, chemokines, and cytolytic molecules, the various combinations of which can be assessed combinatorially. For example, HIV nonprogressors develop CD8⁺ T-cell responses that are characterized by almost universal production of interferon-gamma (INFγ), CD107a, and MIP-1beta but individual responding cells express differing combinations of IL-2 and TNFα—that is, individual responders might express neither, one, or both of these latter cytokines (M. R. Betts et al., 107 Blood 4781 (2006)).

The scientific community has expended considerable effort to determine factors that drive these alternative fates, with the study of cytokines having been an especially fruitful focus. For example, inflammatory cytokines including IL-12, type-I interferon, and interferon-gamma have been shown to enhance generation of effector CD8⁺ T cells (W. Cui & S. M. Kaech, 236 Immunol. Rev. 151 (2010); J. T. Harty & V. P. Badovinac, 8 Nat. Rev. Immunol. 107 (2008)). Conversely, cytokines such as IL-6 and IL-21 activate the transcription factor STAT3 and promote the T-cell memory fate. These cytokines have a variety of functional associations. IL-6 is associated with inflammation, whereas IL-21 is well characterized for its participation in CD4$^+$ T cell-B cell collaboration in the germinal center. It has been shown that STAT3-deficient cells that persist through to the memory phase have characteristics of effector, not normal, memory cells. Phenotypically the cells manifest reduced expression of the IL-7 receptor alpha chain (CD127) and high expression of KLRG-1, which is typical of effectors. Expression of the memory-associated transcriptional regulators, Eomes and BCL-6, decline in STAT3-deficient T cells as those cells reach the memory phase of the response (W. Cui, Y. Liu, J. S. Weinstein, J. Craft & S. M. Kaech, 35 Immunity 792 (2011)). A defined target of STAT3, SOCS3, seems to play an important role in maintaining memory-cell differentiation by inhibiting cytokine receptor signaling, thereby "insulating" T cells from inflammatory signals that could derail normal memory-cell homeostasis (W. Cui, Y. Liu, J. S. Weinstein, J. Craft & S. M. Kaech, 35 Immunity 792 (2011)). Furthermore, human patients with dominant-negative mutations in STAT3 have a decreased frequency and absolute number of central memory T cells (A. M. Siegel et al., 35 Immunity 806 (2011)). Most impressively, in a patient who was mosaic for the mutation, STAT3 mutant cells were found among B cells and naïve T cells, but not among memory CD4$^+$ or CD8$^+$ T cells, confirming the importance of STAT3 function for differentiation of these cell types.

T cells also differ in their anatomic localization due to different expression of "homing receptors" that may position the cells optimally for response, e.g., to SARS-CoV-2 in the lung (J. Zhao et al., 44 Immunity 1379 (2016)), HIV in the gut (S. G. Hansen et al., 15 Nat. Med. 293 (2009)), tuberculosis in the lung (S. Sakai et al., 12 PLoS Pathog. e1005667 (2016)), or hepatitis C virus in the liver. Memory T cells elicited by vaccination are generally most effective against a pathogen when located in the pathogen's target tissue (S. G. Hansen et al., 15 Nat. Med. 293 (2009)). Memory CD4$^+$ T cells are more numerous at sites of infection than CD8$^+$ T cells (D. L. Turner & D. L. Farber, 5 Front. Immunol. 331 (2014)) and have multiple roles in initiating and propagating the immune response (S. L. Swain, K. K. McKinstry & T. M. Strutt, 12 Nat. Rev. Immunol. 136 (2012)). In the respiratory tract, memory CD4$^+$ T cells include cells in the airway and parenchyma and cells adhering to the pulmonary vasculature. Airway memory CD4$^+$ T cells are the first cells to encounter viral antigen during respiratory infections, suggesting a key role in protection. Indeed, Zhao and colleagues found that intranasal vaccination with Venezuelan equine encephalitis replicons encoding a SARS-CoV CD4$^+$ T cell epitope induced airway CoV-specific memory CD4$^+$ T cells that protected mice against lethal disease through rapid local IFNγ production (J. Zhao et al., 44 Immunity 1379 (2016)). Protection was dependent on IFNγ and required early induction of robust innate responses and recruitment of virus-specific CD8$^+$ T cells to lung in a CXCR3-dependent process. CXCR3 ligands (the chemokines CXCL9, CXCL10, and CXCL11) were expressed in the infected lungs only when airway CD4$^+$ T cells were present and able to express IFNγ. Systemic blockade of CXCR3 at days 3 or 5 p.i. decreased the frequency and numbers of pathogen-specific CD8$^+$ T cells in the lungs. Thus, airway memory CD4$^+$ T cells orchestrated both respiratory DC migration to the lymph nodes and virus-specific CD8$^+$ T cell trafficking to the lungs, improving clinical outcomes.

Furthermore, it has been demonstrated in the "Step" trial that non-specific IFNγ secretion is associated with increased HIV infection risk. Step was a phase-2b randomized double-blind human clinical trial of a preventive HIV vaccine in 3000 participants. The trial tested if the adenovirus serotype 5 (Ad5)-vectored MRKAd5 HIV-1 gag/pol/nef vaccine could reduce either HIV-1 infection rates or plasma viremia after infection. This study showed no evidence for vaccine efficacy. Rather, risk of HIV infection was elevated among male recipients who had pre-existing Ad5 neutralizing antibodies (S. P. Buchbinder et al., 372 Lancet 1881 (2008); A. Duerr et al., 206 J. Infect. Dis. 258 (2012)). The elevated risk of HIV infection with vaccination suggested a harmful immune response to the vaccine that was responsible for increased risk. Indeed, in a related non-human primate study a greater risk of infection was observed in animals pre-exposed to Ad5 and immunized with an Ad5 simian immunodeficiency virus (SIV) vaccine, compared to those not pre-exposed to Ad5 (H. Kureshi et al., 86 J. Virol. 2239 (2012)). Subsequent analysis of the immune responses of Step-trial participants found that HIV-specific immune responses were not associated with risk of HIV-1 infection (Y. Huang, wt al., 9 PLoS One e108631 (2014)). However, each one-natural-log increase of mock responses measured by ELISpot (i.e., IFNγ secretion in the absence of antigen-specific stimulation) was associated with a 62% increase of HIV-1 infection risk (p=0.001) (Y. Huang, wt al., 9 PLoS One e108631 (2014)). Together these studies demonstrate that vectored vaccines such as Ad-based vaccines can be associated with harmful responses that must be avoided for the vaccine to have the intended benefit for recipients.

Subsequent authors more closely examined the effects of vaccine insert-specific T-cell responses on HIV acquisition. It was demonstrated that a vaccine regimen based on DNA prime and modified vaccinia Ankara boost induced interferon-gamma-producing CD4$^+$ T cells (Th1 cells) that rapidly migrated to multiple tissues including colon, cervix, and vaginal mucosa (V. Chamcha et al., 11 Sci. Transl. Med. eaav1800 (2019)). These mucosal Th1 cells expressed higher density of CCR5, a coreceptor for the SIV virus, compared to cells in blood. After intravaginal or intrarectal simian-human immunodeficiency virus (SHIV) challenges, strong vaccine protection was evident only in animals that had lower frequencies of vaccine-specific Th1 cells but not in animals that had higher frequencies of Th1 cells, despite comparable antibody and CD8$^+$ T-cell immunity in both groups. An RNA transcriptome signature of fewer Th1 cells in blood at 7 days after priming immunization was associated in one study with enhanced protection. Thus, high frequencies of HIV vaccine-induced Th1-biased CD4$^+$ T cells in the intestinal and genital mucosa can mitigate beneficial effects of protective antibodies and CD8$^+$ T cells.

IFNγ producing cells can similarly have negative consequences for infection with *Mycobacterium tuberculosis* (Mtb). IFNγ—producing CD4 T cells are required for protection against Mtb. However, it was not previously known if further increasing IFNγ production by CD4 T cells is desirable in Mtb. In particular, although some such cells are needed it was unclear if supraphysiologic IFNγ production by CD4 T cells would be beneficial. It was shown recently that increasing the IFNγ—producing capacity of CD4 T cells by ~2 fold exacerbates lung infection and leads to the early death of the host, despite enhancing control in the spleen. In addition, the inhibitory receptor PD-1 facilitates host resistance to Mtb by preventing detrimental over-production of IFNγ by CD4 T cells. In summary, the primary role for T cell-derived IFNγ in Mtb infection is at extra-pulmonary sites such as spleen, and the host-protective subset of CD4 T cells requires negative regulation of IFNγ production by PD-1 to prevent lethal immunopathology.

In view of these observations and results, there is a need in the art for improved vaccines that create long-lived memory cells having the character needed for protection against disease. The present disclosure addresses this need and provides associated and other advantages.

BRIEF SUMMARY

In general, provided herein are novel materials and methods for promoting development of long-lived memory cells through increased amino-acid catabolism. In one aspect, the disclosure provides a recombinant polynucleotide including a first nucleic acid sequence encoding an antigen, and a second nucleic acid sequence encoding an enzyme of an amino acid catabolic pathway.

In some embodiments, the amino acid catabolic pathway is an L-tryptophan catabolic pathway. In some embodiments, the enzyme of the L-tryptophan catabolic pathway is indoleamine 2,3-dioxygenase 1 or a paralogue or isoform thereof. In some embodiments, the enzyme of the L-tryptophan catabolic pathway is tryptophan 2,3-dioxygenase or a paralogue or isoform thereof. In some embodiments, the amino acid catabolic pathway is an L-arginine catabolic pathway. In some embodiments, the enzyme of the L-arginine catabolic pathway is arginase 1 or a paralogue or isoform thereof. In some embodiments, the enzyme of the L-arginine catabolic pathway is nitric oxide synthase 2 or a paralogue or isoform thereof. In some embodiments, the enzyme is interleukin 4-induced gene 1. In some embodiments, the enzyme is an L-amino acid oxidase.

In some embodiments, the antigen includes a viral nucleoprotein. In some embodiments, the antigen includes a secreted protein. In some embodiments, the antigen includes an infectious disease antigen. In some embodiments, the infectious disease antigen is a bacterial antigen, a viral antigen, a fungal antigen, a protozoal antigen, and/or a helminthic antigen. In some embodiments, the infectious disease antigen is a severe acute respiratory syndrome coronavirus (SARS-CoV) antigen, a severe acute respiratory syndrome coronavirus 2 (SARS-CoV-2) antigen, a Middle East respiratory syndrome coronavirus (MERS-CoV) antigen, a simian immunodeficiency virus (SIV) antigen, a human immunodeficiency virus (HIV) antigen, a hepatitis C virus antigen, a herpes simplex virus antigen, an Epstein-Barr virus antigen, a cytomegalovirus antigen, and/or an influenza virus antigen. In some embodiments, the infectious disease antigen is an SIV group-specific antigen (gag) protein and/or an HIV gag protein. In some embodiments, the infectious disease antigen is a bacterial disease antigen from *Mycobacterium tuberculosis, Borrelia burgdorferi, Brucella abortus, Listeria monocytogenes, Chlamydia trachomatis, Coxiella burnetii, Salmonella enterica, Francisella tularensis*, or *Rickettsia* spp. In some embodiments, the infectious disease antigen is a protozoal disease antigen from *Plasmodium falciparum* or *Toxoplasma gondii*. In some embodiments, the antigen includes a tumor-associated antigen. In some embodiments, the tumor-associated antigen is a prostate-specific antigen, melanoma-associated antigen 4 (MAGEA4), melanoma-associated antigen 10 (MAGEA10), New York esophageal squamous cell carcinoma 1 (NY-ESO-1), and/or a neoantigen.

In some embodiments, at least one of the first nucleic acid sequence and the second nucleic acid sequence is codon optimized. In some embodiments, the recombinant polynucleotide further includes at least one promoter sequence. In some embodiments, the recombinant polynucleotide further includes at least one internal ribosome entry site sequence. In some embodiments, the recombinant polynucleotide further includes at least one polyadenylation sequence.

In another aspect, the disclosure provides a viral particle including any of the recombinant polynucleotides disclosed herein.

In another aspect, the disclosure provides a host cell including any of the recombinant polynucleotides disclosed herein.

In another aspect, the disclosure provides a pharmaceutical composition including any of the recombinant polynucleotides disclosed herein, and a pharmaceutically acceptable carrier and/or pharmaceutically acceptable excipient.

In another aspect, the disclosure provides a method for inducing an immune response against an antigen in a subject. The method includes administering to the subject a therapeutically effective amount of any of the pharmaceutical compositions disclosed herein.

In some embodiments, the immune response includes increased production of CD4$^+$ memory cells. In some embodiments, the immune response includes an increased ratio of CD4$^+$ cells to CD8$^+$ cells. In some embodiments, the immune response includes increased production of T memory stem cells. In some embodiments, the immune response includes increased production of interleukin 10 (IL-10). In some embodiments, the immune response includes activation of the general control nonderepressible 2 (GCN2) kinase. In some embodiments, the immune response includes activation of the arylhydrocarbon receptor (AhR). In some embodiments, the immune response includes increased production of nitric oxide (NO). In some embodiments, the immune response includes increased production of spermidine. In some embodiments, the immune response induced in the subject is greater than an immune response induced using a corresponding recombinant polynucleotide that does not include the second nucleic acid sequence. In some embodiments, the immune response includes generation of antibodies that recognize the antigen.

In some embodiments, the method further includes obtaining a test sample from the subject. In some embodiments, the test sample includes a blood sample, a tissue sample, a urine sample, a saliva sample, and/or a cerebrospinal fluid sample. In some embodiments, the method further includes determining the level of one or more biomarkers in the test sample. In some embodiments, the one or more biomarkers include C-reactive protein, IFNγ, tumor necrosis factor alpha, interleukin 4, interleukin 5, interleukin 6, IL-10, interleukin 12, interleukin 15, GCN2 kinase, AhR, SHP-1, SHP-2, NO, and/or spermidine. In some embodiments, the method further includes comparing the level of the one or more biomarkers in the test sample to the level of the one or more biomarkers in a reference sample. In some embodiments, the reference sample was obtained from the subject prior to the obtaining of the test sample. In some embodiments, the reference sample is obtained from a different subject or from a population of subjects.

In another aspect, the disclosure provides a method for preventing or treating a disease in a subject. The method includes administering to the subject a therapeutically effective amount of any of the pharmaceutical compositions disclosed herein. In some embodiments, the disease is an infectious disease or a cancer. In some embodiments, the infectious disease is caused by a bacterial infection, a viral infection, a fungal infection, a protozoal infection, and/or a helminthic infection. In some embodiments, the infectious disease is caused by a SARS-CoV virus, a SARS-CoV-2 virus, a MERS-CoV virus, an SIV virus, an HIV virus, a hepatitis C virus, a herpes simplex virus, an Epstein-Barr virus, a cytomegalovirus antigen, and/or an influenza virus antigen. In some embodiments, the infectious disease is caused by *Mycobacterium tuberculosis, Borrelia burgdorferi, Brucella abortus, Listeria monocytogenes, Chlamydia trachomatis, Coxiella burnetii, Salmonella enterica, Francisella tularensis,* or *Rickettsia* spp. In some embodiments, the infectious disease is caused by a protozoal disease antigen from *Plasmodium falciparum* or *Toxoplasma gondii.* In some embodiments, the treating of the disease includes decreasing or eliminating one or more signs or symptoms of the disease.

DETAILED DESCRIPTION

Figure 1:
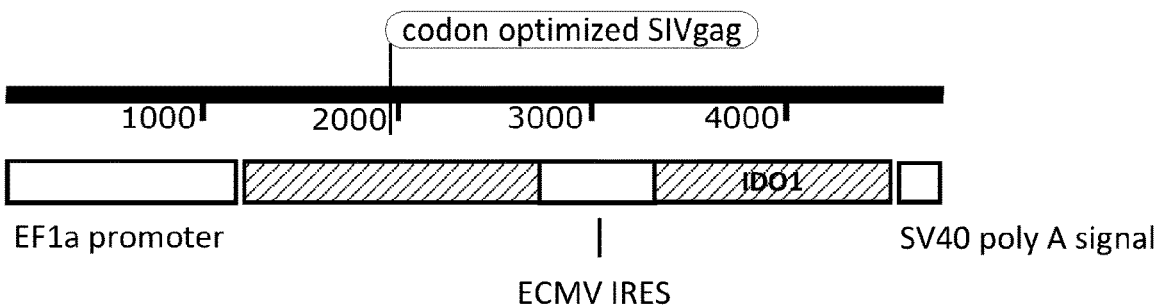
FIG. 1 is an illustration of a bicistronic expression cassette for driving production of both the SIV Gag gene and indoleamine 2,3-dioxygenase in cells. Ad-Gag-IRES-IDO1 vaccine contains this cassette in "vectorized" Ad5 or Ad26. Expression of the bicistronic transcript is driven by a human EF1α promoter containing the first intron; the coding regions for SIV Gag and rhesus macaque IDO1 are separated by an ECMV internal ribosomal entry site; and the cassette is terminated by an SV40 virus polyadenylation signal.

Some amino acid catabolic pathways have been found to be associated with aspects of immunity, allowing limitation of adaptive immune responses in the effector phase and preventing exaggerated inflammation (U. Grohmann & V. Bronte, 236 Immunol. Rev. 243 (2010); P. J. Murray, 17 Nat. Immunol. 132 (2016)). Despite the importance of the immunoregulatory pathways engaged in contraction of the effector responses and generation of memory, the relationship of these effector-phase checkpoints to memory-cell generation has been little examined.

For example, IDO and other amino acid catabolizing enzymes have been targeted for inhibition, on the theory that such inhibition would lead broadly to a greater immune reaction against cancer cells. In particular, it has been argued that amino acid catabolism within tumor tissue plays an important role in establishing the microenvironment that prevents effective immune responses and sustains the tumor. Due to the immunosuppressive microenvironment, tumor-infiltrating cells are those most heavily suppressed, as demonstrated by defective cytolytic activity when the cells are extracted from the tumor and tested ex vivo. To counter this metabolic dysregulation at tumor sites, inhibition of amino-acid metabolism has therefore been explored (T. F. Gajewski et al., 213 Immunol. Rev. 131; P. C. Rodriguez et al., 64 Cancer Res. 5839 (2004)). It has not been previously recognized, however, that amino acid catabolism modulates different arms and phases of the adaptive immune response to varying degrees, and that blanket inhibition of the pathway will stimulate only some aspects of adaptive immunity, while likely interfering with others (such as memory-cell generation). The overall effect is therefore best characterized as a rebalancing rather than unidimensional stimulation.

A surprising advantage realized by the materials and methods disclosed herein is the enabling of amino acid catabolic enzyme expression in the context of vaccinations to provide such rebalanced responses, e.g., with greater intensity of CD4$^+$ T-cell responses relative to CD8$^+$ T-cell responses. This advantage can be realized through, for example, the counterintuitive step of increasing, rather than decreasing, amino acid catabolism enzyme activity with vaccine administration. Such an approach recognizes that enzymes of amino acid catabolic pathways can inhibit certain counter-productive or irrelevant immune responses while augmenting others. Most importantly, this strategy results in vaccines with the capacity to elicit unusually strong memory responses that persist without appreciable degradation for many months after vaccination. These amino acid-catabolizing vaccines also elicit greater responses among CD4$^+$ T cells accompanied by lesser responses among CD8$^+$ T cells, which is a profile not observed with many other vaccine types. The provided materials and methods can also beneficially result in modestly reduced IFNγ production among responding T cells, which may be desired under circumstances related to, e.g., infectious diseases or cancers.

Recombinant Polynucleotides

In one aspect, a recombinant polynucleotide is disclosed. The recombinant polynucleotide provides surprising improvements in inducing an immune response in a subject. For example, the disclosed recombinant polynucleotide can advantageously improve the memory effects of the induced immune response as discussed in further detail herein.

As used herein, the terms "polynucleotide" and "nucleic acid" refer to deoxyribonucleic acids (DNA) or ribonucleic acids (RNA) and polymers thereof. The term includes, but is not limited to, single-, double-, or multi-stranded DNA or RNA, genomic DNA, cDNA, and DNA-RNA hybrids, as well as other polymers comprising purine and/or pyrimidine bases or other natural, chemically modified, biochemically modified, non-natural, synthetic, or derivatized nucleotide bases. Unless specifically limited, the term encompasses nucleic acids containing known analogs of natural nucleotides that have similar binding properties as the reference nucleic acid. Unless otherwise indicated, a particular nucleic acid sequence also implicitly encompasses conservatively modified variants thereof, e.g., degenerate codon substitutions, homologs, and complementary sequences as well as the sequence explicitly indicated. Specifically, degenerate codon substitutions can be achieved by generating sequences in which the third position of each of one or more, e.g., all, selected codons is independently substituted with mixed-base and/or deoxyinosine residues (Batzer et al., 19 Nucleic Acid Res. 5081 (1991); Ohtsuka et al., 260 J. Biol. Chem. 2605 (1985); Rossolini et al., 8 Mol. Cell. Probes 91 (1994)).

As used herein, the term "recombinant polynucleotide" refers to a polynucleotide that has been modified by the introduction of a heterologous nucleic acid or protein sequence, or by the alteration of a native nucleic acid or protein sequence. For example, recombinant polynucleotides contain nucleic acid sequences that are not found within the native (non-recombinant) form of the polynucleotide.

The recombinant polynucleotide includes a first nucleic acid sequence and a second nucleic acid sequence. The first nucleic acid sequence of the recombinant polynucleotide encodes an antigen. The second nucleic acid sequence of the recombinant polynucleotide encodes an enzyme of an amino acid catabolic pathway. In some embodiments, the recombinant polynucleotide is bicistronic, e.g., the polynucleotide has two loci, i.e., nucleic acid sequences, each encoding a separate protein, such that the polynucleotide enables simultaneous expression of the two proteins. In some embodiments, the recombinant polynucleotide is tricistronic, e.g., having three loci each encoding a separate protein. In some embodiments, the recombinant polynucleotide is multicistronic, e.g., having four loci, five loci, six loci, seven loci, eight loci, nine loci, ten loci, or more than ten loci, each encoding a separate protein.

Amino Acid Catabolic Pathway Enzymes

The provided recombinant polynucleotide includes at least one nucleic acid sequence encoding an enzyme of an amino acid catabolic pathway. In some embodiments, the recombinant polynucleotide includes two nucleic acid sequences that each independently encode an enzyme of an amino acid catabolic pathway. In some embodiments, the recombinant polynucleotide includes more than two nucleic acid sequences, e.g., more than three nucleic acid sequences, more than four nucleic acid sequences, more than five nucleic acid sequences, more than six nucleic acid sequences, more than seven nucleic acid sequences, more than eight nucleic acid sequences, more than nine nucleic acid sequences, or more than ten nucleic acid sequences that each independently encode an enzyme of an amino acid catabolic pathway.

As used herein, the term "nucleic acid sequence" refers to a segment of DNA, which in some embodiments may be a gene or a portion thereof, that is involved in producing a peptide chain, e.g., an amino acid catabolic pathway enzyme or an antigen. A gene will generally include regions, e.g., leaders and trailers, preceding and following the coding region and involved in the transcription and/or translation of the gene product. A gene can also include intervening sequences, e.g., introns, between individual coding segments, e.g., exons. Leaders, trailers, and introns can include regulatory elements that are necessary during the transcription and the translation of a gene. Such regulatory elements include, for example, promoters, terminators, translational regulatory sequences such as ribosome binding sites and internal ribosome entry sites, enhancers, silencers, insulators, boundary elements, replication origins, matrix attachment sites, and locus control regions, etc.

The immunoregulatory effects of amino acid-catabolizing enzymes rely on the depletion of specific amino acids in the microenvironment (preventing, e.g., proliferation of effector T cells requiring those amino acids) and/or downstream generation of biologically active metabolites. Each degradative pathway is characterized by a rate-limiting enzyme, whose expression is normally subjected to strict regulation but which can be expressed in the context of a vaccine, as provided herein, to limit effector and shape memory T-cell responses. For example, indoleamine 2,3-dioxygenase 1 (IDO1) and arginase 1 (ARG1) limit the catabolism of L-tryptophan (Trp) and L-arginine (Arg), respectively (G. Mondanelli, S. Ugel, U. Grohmann & V. Bronte, 35 Curr. Opin. Pharmacol. 30 (2017)). Natural immunoregulatory mechanisms can work via induction of these enzymes. For example, transforming growth factor β (TGF-β), an immunosuppressive cytokine, promotes the sequential activation of ARG1 and IDO1 thus inducing a potent immunoregulatory phenotype in dendritic cells (G. Mondanelli et al., 46 Immunity 233 (2017)).

In some embodiments, a nucleic acid sequence, e.g., the second nucleic acid sequence, of the provided recombinant polynucleotide encodes an enzyme of an L-trytophan catabolic pathway. In the case of tryptophan catabolism, three distinct enzymes are capable of catalyzing the rate-limiting step: tryptophan 2,3-dioxygenase (TDO), IDO1, and the IDO1 paralogue indoleamine 2,3-dioxygenase 2 (IDO2). In some embodiments, the recombinant polynucleotide includes a nucleic acid sequence encoding tryptophan 2,3-dioxygenase or a paralogue or isoform thereof. In some embodiments, the recombinant polynucleotide includes a nucleic acid sequence encoding indoleamine 2,3-dioxygenase 1 or an isoform thereof. In some embodiments, the recombinant polynucleotide includes a nucleic acid sequence encoding indoleamine 2,3-dioxygenase 2 or an isoform thereof. In some embodiments, the recombinant polynucleotide includes a nucleic acid sequence encoding tryptophan 2,3-dioxygenase or a paralogue or isoform thereof, and a nucleic acid sequence encoding indoleamine 2,3-dioxygenase or a paralogue or isoform thereof.

Tryptophan catabolism leads to Trp starvation (resulting in inhibited replication of immune cells in the vicinity), production of metabolites collectively known as kynurenines, and synthesis of nicotinamide adenine dinucleotide (NAD+) (R. Schwarz, 4 Curr. Opin. Pharmacol. 12 (2004)). These effects have downstream impacts on immune responses occurring concomitantly with Trp catabolism, including conversion of effector T helper cells into regulatory T cells (F. Fallarino et al., 4 Nat. Immunol. 1206 (2003)), a type of memory T cell, and blockade of the conversion of Treg into pro-inflammatory type 17 Th (Th17) cells (B. Baban et al, 183 J. Immunol. 2475 (2009)). Some of the mechanisms of these and other immunoregulatory effects have been elucidated. For example, Trp deprivation results in an elevated level of uncharged Trp tRNA, which in turn activates an integrated stress response mediated by the general control nonderepressible 2 (GCN2) kinase, phosphorylation of the translation initiation factor 2 (eIF2a), and consequent reduced protein synthesis. GCN2 activation can trigger differentiation, compensatory adaptation, cell-cycle arrest, or apoptosis, depending on the cell type (K. Pakos-Zebrucka et al., 17 EMBO Rep 1374 (2016)). In T lymphocytes, sufficient GCN2 activation induced by IDO1+ dendritic cells leads to proliferative arrest and anergy (D. H. Munn et al., 22 Immunity 633 (2005)). These effects, in turn, alter the balance of resulting immune responses, with florid inflammatory responses of the kind thought to be harmful in HIV infection inhibited. Kyn, the direct IDO1 product, and kynurenic acid can activate the arylhydrocarbon receptor (AhR). When activated in immune cells (either dendritic cells or T lymphocytes), AhR mediates immunoregulatory responses favoring Treg cell generation and production of anti-inflammatory cytokines (M. Jaronen & F. J. Quintana, 5 Front. Immunol. 521 (2014); B. Stockinger, P. Di Meglio, M. Gialitakis & J. H. Duarte, 32 Annu. Rev. Immunol. 403 (2014)).

The signaling pathways that regulate T-cell metabolic reprogramming have been the subject of intense research in the past decade. mTOR is an evolutionarily conserved ser/thr kinase that, in T cells, integrates nutrient sensing and antigen-receptor signaling (R. J. Salmond & R. Zamoyska, 41 Eur. J. Immunol. 2137 (2011); R. J. Salmond & R. Zaoyska, 9 Cell Cycle 2952 (2010)). mTOR forms two main signaling complexes, mTORC1 and mTORC2, that differ in their sensitivity to the macrolide inhibitor rapamycin. mTORC1 activity is regulated by intracellular amino acids, such as tryptophan, via the nutrient-sensing Rag GTPases (R. L. Wolfson & D. M. Sabatini, 26 Cell Metab. 301 (2017)). Upon TCR stimulation, T cells upregulate the expression of plasma membrane transporters that enable the uptake of amino acids such as leucine and glutamine from the extracellular environment, which in turn sustain mTORC1 activation. Whilst the anti-proliferative and immunosuppressive properties of rapamycin have been known for decades, recent studies determined that mTOR activity also influences T cell effector-memory cell fate decisions in vivo (K. Araki et al., 460 Nature 108 (2009)). Specifically, rapamycin treatment and mTOR inhibition enhanced the quantity and quality of virus-specific CD8[+] memory T cells in mice and macaques. Consistent with these findings, activation of the AMPK1 pathway via metformin or via glucose-deprivation restrains mTOR activity (J. Rolf et al., 43 Eur. J. Immunol. 889 (2013); E. L. Pearce et al., 460 Nature 103 (2009)) and enhances T cell memory.

Like rapamycin, indoleamine 2,3-dioxygenase activity and resulting tryptophan depletion inhibit mTOR activity. Trp depletion caused by IDO leads to an accumulation of uncharged Trp-tRNA in cells. This accumulation activates the integrated stress response kinase, GCN2, which then phosphorylates and inhibits the translation initiation factor 2a (eIF2a), blocking protein synthesis and arresting cell growth (D. H. Munn et al., 22 Immunity 633 (2005)). Notably, the genetic or pharmacological manipulation of GCN2 in T cells phenocopies the effect of IDO-targeted manipulation (D. H. Munn et al., 22 Immunity 633 (2005); M. S. Sundrod et al., 324 Science 1334 (2009)). Recent findings indicate that cells employ different signaling pathways to monitor the depletion of essential amino acids such as Trp, resulting eventually in inhibition of the master metabolic regulator, mTOR (K. Inoki, J. Kim & K. L. Guan, 52 Annu. Rev. Pharmacol. Toxicol. 381 (2012)). IDO-mediated Trp depletion thus provides a molecular signal to flip the mTOR-controlled switch away from glycolysis and to fatty-acid oxidation and long-term memory. By analogy to the mTOR-inhibitory agent, rapamycin, IDO drives memory T cell differentiation by controlling Trp sufficiency signals that converge to diminish mTOR activity, diverting activated cells away from short-lived, inflammatory, effector responses.

IDO1 does not merely degrade Trp and produce kynurenines, but it also acts as a signal-transducing molecule, an effect that leads to long-term expression of IDO1 in dendritic cells and to immune responses with an altered character in vivo (M. T. Pallotta et al., 12 Nat Immunol 870 (2011)). IDO1's signaling function relies on the presence of two immunoreceptor tyrosine-based inhibitory motifs (ITIMs) in the small domain of IDO1 (E. Albini et al., 21 J. Cell. Mol. Med. 165 (2016); C. Orabona, 105 Proc. Natl. Adad. Sci. U.S.A. 20828 (2008)). In response to transforming growth factor β (TGF-β), IDO1 ITIMs are tyrosine phosphorylated by Src kinases, creating docking sites for binding and activation of SHP-1 and SHP-2 tyrosine phosphatases. These enzymes in turn dephosphorylate the IRAK kinase, shifting the balance of NF-κB signaling from the canonical, inflammatory pathway to the noncanonical, anti-inflammatory one.

In some embodiments, a nucleic acid sequence, e.g., the second nucleic acid sequence, of the provided recombinant polynucleotide encodes an enzyme of an L-arginine catabolic pathway. Arginine is a conditionally essential amino acid, meaning that its endogenous production in normal conditions is sufficient to fulfill demand, but in catabolic stress conditions the demand increases to such a level that endogenous production is insufficient R. Barazzoni et al., 303 Am. J. Physiol. Endocrinol. Metab. E1177 (2012); G. Wu & S. M. Morris Jr., 336-1 Biochem. J. 1 (1998)). Quickly proliferating cells such as cancer cells and responding immune cells can become highly dependent on the extracellular supply of arginine (G. Wu & S. M. Morris Jr., 336-1 Biochem. J. 1 (1998)).

The major arginine-degrading enzymes are the isoforms of nitric oxide (NO) synthase (NOS1-3) and arginase 1 and 2 (ARG1 and ARG2). In some embodiments, the recombinant polynucleotide includes a nucleic acid sequence encoding nitric oxide synthase 1 or a paralogue thereof. In some embodiments, the recombinant polynucleotide includes a nucleic acid sequence encoding nitric oxide synthase 2 or a paralogue thereof. In some embodiments, the recombinant polynucleotide includes a nucleic acid sequence encoding nitric oxide synthase 3 or a paralogue thereof. In some embodiments, the recombinant polynucleotide includes a nucleic acid sequence encoding arginase 1 or a paralogue thereof. In some embodiments, the recombinant polynucleotide includes a nucleic acid sequence encoding arginase 2 or a paralogue thereof. In some embodiments, the recombinant polynucleotide includes a nucleic acid sequence encoding nitric oxide synthase 2 or a paralogue or isoform thereof, and a nucleic acid sequence encoding arginase 1 or a paralogue or isoform thereof.

The three NOS isozymes catalyze the same reaction but have different distribution and regulation (C. Bogdan, 2 Nat. Immunol. 907 (2001)). NOS1 (also known as the neuronal form) and NOS3 (known as the endothelial form) are constitutive enzymes, whereas NOS2 (referred as inducible NOS; iNOS) is induced by pro-inflammatory cytokines and microbial products. The metabolism of Arg by NOS generates NO, a relatively stable gas that diffuses through the lipid membrane and acts as signaling molecule. Myeloid cells, including macrophages, dendritic cells, and myeloid derived suppressor cells, express ARG1 in response to Th2-type cytokines, cyclic AMP, toll-like receptor agonists and several tumor-derived soluble factors, such as IL-6 and TGF-β M. Munder, 158 Br. J. Pharmacol. 638 (2009); R. Noy & J. W. Pollard, 41 Immunity 49 (2014)). In humans, ARG1 is constitutively present in an inactive form in the granular compartment of polymorphonuclear neutrophils, where it becomes activated upon extracellular release during inflammation (R. Rotondo et al., 89 J. Leukoc. Biol. 721 (2011)). When Arg is limiting in the microenvironment, T lymphocytes lose CD3 zeta chain expression, which is required to transduce their primary activating signal, and become unable to proliferate (P. C. Rodriguez, D. G. Quicenero & A. C. Ochoa, 109 Blood 1568 (2006)). In addition to the effects of Arg starvation, the metabolites originated from its breakdown, particularly polyamines, have immunoregulatory properties including attenuation of proinflammatory-cytokine production and activation of Trp catabolism (Y. H. Choi & H. Y Park, 19 J. Biomed. Sci. 31 (2012); G. Mondanelli, S. Ugel, U. Grohmann & V. Bronte, 35 Curr. Opin. Pharmacol. 30 (2017); G. Mondanelli et al., 46 Immunity 233 (2017)). Specifically, spermidine, through activation of the Src kinase, promotes the phosphorylation of IDO1 and thus favors the initiation of immunoregulatory signaling events in dendritic cells, creating a self-sustaining circuitry responsible for long-term immunoregulation (G. Mondanelli et al., 46 Immunity 233 (2017)).

Enzymes involved in the metabolism of arginine and tryptophan, such as inducible NO synthase and IDO, can additionally regulate B cell survival and proliferation, respectively (A. S. Saini, G. N. Shenoy, S. Rath, V. Bal & A. George, 15 Nat. Immunol. 275 (2014); R. Shinde et al., 195 J. Immunol. 2374 (2015)). Such regulation leads to an altered balance between B-cell and T-cell responses to an immunogen, depending on presentation of an immunogen in the presence of Trp and/or Arg catabolism.

In some embodiments, a nucleic acid sequence, e.g., the second nucleic acid sequence, of the provided recombinant polynucleotide encodes interleukin 4-induced gene 1 or a paralogue or isoform thereof. IL-4-induced gene-1 (IL4I1), initially isolated from mouse B lymphocytes, is limited in expression to primarily immune tissues and genetically maps to a region of susceptibility to autoimmune disease.

The predicted IL4I1 protein (IL4I1) sequence is most similar to apoptosis-inducing protein and Apoxin I, both L-amino acid oxidases (LAAO; Enzyme Commission 1.4.3.2). IL4I1 has the unique property of being most active at acidic pH (pH 4), suggesting it may reside preferentially in lysosomes. IL4I1 is N-linked glycosylated, a requirement for lysosomal localization. Confocal microscopy of cells expressing IL4I1 translationally fused to red fluorescent protein demonstrated that IL4I1 colocalized with GFP targeted to lysosomes and with acriflavine, a green fluorescent dye that is taken up into lysosomes. Thus, IL4I1 is a unique mammalian LAAO targeted to lysosomes, an important subcellular compartment involved in Ag processing.

The secreted IL4I1 enzyme catabolizes the essential amino acid phenylalanine and, to a lesser extent, the semi-essential amino acid arginine, to produce the corresponding α-keto acids (phenylpyruvate and 2-oxo-5-guanidinovaleric acid, respectively), hydrogen peroxide ($H_2O_2$), and ammonia (NH3) (M.-L. Boulland et al., 110 Blood 220 (2007); V. Moliner-Frenkel, D. Mestivier & F. Castellano, 17 Genes Immun. 148 (2016)). IL4I1 is induced in human monocytes after stimulation by proinflammatory stimuli such as IFNγ or TLR ligands and in B cells after stimulation with IL-4 (J. Marquet et al., 40 Eur. J. Immunol. 2557 (2010); C. C. Chu & W. E. Paul, 94 Proc. Natl. Adad. Sci. U.S.A. 2507 (1997)). The first data published on the immunoregulatory properties of IL4I1 indicate that it inhibits T cell activation and proliferation in vitro and in vivo, partially through $H_2O_2$ production (M.-L. Boulland et al., 110 Blood 220 (2007); F. Lasoudris et al., 41 Eur. J. Immunol. 1629 (2011)). IL4I1 drives the polarization of mouse macrophages toward an M2 phenotype (Y. Yue et al., 10 PLoS One e0142979 (2015)).

Stable lines expressing IL4I1 are not be easily obtained, due to toxic effects of the protein; therefore, repressible expression may be needed for inclusion into vaccine vectors. Alternatively, a DNA-based vaccine including the enzyme coding sequence could be used.

In some embodiments, at least one of the one or more nucleic acid sequences encoding an amino acid catabolic pathway enzyme is a nucleic acid sequence encoding an amino acid oxidase, e.g., an L-amino acid oxidase.

Antigens

The provided recombinant polynucleotide includes at least one nucleic acid sequence encoding an antigen. In some embodiments, the recombinant polynucleotide includes two nucleic acid sequences that each independently encode an antigen. In some embodiments, the recombinant polynucleotide includes more than two nucleic acid sequences, e.g., more than three nucleic acid sequences, more than four nucleic acid sequences, more than five nucleic acid sequences, more than six nucleic acid sequences, more than seven nucleic acid sequences, more than eight nucleic acid sequences, more than nine nucleic acid sequences, or more than ten nucleic acid sequences that each independently encode an antigen.

As used herein, the term "antigen" refers to a molecule, or a portion thereof, that is capable of inducing an immune response, e.g., an immune response in a subject. While in many instances an immune response involves the production of an antibody that targets or specifically binds to the antigen, as used herein the term "antigen" also refers to molecules that induce immune responses other than those that specifically involve the production of an antibody that targets the antigen. For example, an antigen can induce a cell-mediated immune response involving expansion of T cells that target antigen-derived peptides presented on the surface of target cells. In particular embodiments, the antigens of the invention are derived from pathogens, such that the immune response of the subject provides immune protection against the pathogen. In particular embodiments, the pathogen is a virus, such as SARS-CoV-2.

In some embodiments, a nucleic acid sequence, e.g., the first nucleic acid sequence, of the provided recombinant polynucleotide encodes a viral nucleoprotein antigen. In some embodiments, a nucleic acid sequence, e.g., the first nucleic acid sequence, of the recombinant polynucleotide encodes a secreted protein antigen.

In some embodiments, a nucleic acid sequence, e.g., the first nucleic acid sequence, of the provided recombinant polynucleotide encodes an infectious disease antigen. The infectious disease antigen encoded by the provided recombinant polynucleotide can include, for example, a bacterial antigen, a viral antigen, a fungal antigen, a protozoal antigen, a helminthic antigen, or a combination thereof.

In some embodiments, a nucleic acid sequence, e.g., the first nucleic acid sequence, of the provided recombinant polynucleotide encodes a viral antigen. The viral antigen can include, for example, a severe acute respiratory syndrome coronavirus (SARS-CoV) antigen, a severe acute respiratory syndrome coronavirus 2 (SARS-CoV-2) antigen, a Middle East respiratory syndrome coronavirus (MERS-CoV) antigen, a simian immunodeficiency virus (SIV) antigen, a human immunodeficiency virus (HIV) antigen, a hepatitis C virus antigen, a herpes simplex virus antigen, an Epstein-Barr virus antigen, a cytomegalovirus antigen, an influenza virus antigen, or a combination thereof.

In some embodiments, the infectious disease antigen encoded by the provided recombinant polynucleotide includes an SIV group-specific antigen (gag) protein, an HIV gag protein, or a combination thereof. As used herein, the term "group-specific antigen" or "gag" refers to a protein encoded by a retroviral gag gene. Gag genes encode the core structural proteins of retroviruses. For example, in human immunodeficiency virus (HIV), the gag gene encodes a gag polyprotein precursor ($Pr55^{Gag}$), which is subsequently proteolytically processed into the p17 matrix protein (MA), the p24 capsid protein (CA), the p7 nucleocapsid protein (NC), the SP1 and SP2 spacer peptides, and the p6 polypeptide that is located at the N-terminus of the gag polyprotein. In the closely related simian immunodeficiency viruses (SIV), the gag gene similarly encodes a gag polyprotein precursor, which is subsequently proteolytically processed into proteins having similar molecular weights to their HIV equivalents. Non-limiting examples of HIV and SIV gag protein sequences are set forth under UniProt reference numbers P04591 and P89153, respectively.

In some embodiments, a nucleic acid sequence, e.g., the first nucleic acid sequence, of the provided recombinant polynucleotide encodes a bacterial disease antigen. The bacterial disease antigen can originate from, for example, *Mycobacterium tuberculosis, Borrelia burgdorferi, Brucella abortus, Listeria monocytogenes, Chlamydia trachomatis, Coxiella burnetii, Salmonella enterica, Francisella tularensis*, or *Rickettsia* spp.

In some embodiments, a nucleic acid sequence, e.g., the first nucleic acid sequence, of the provided recombinant polynucleotide encodes a protozoal disease antigen. The protozoal disease antigen can originate from, for example, *Plasmodium falciparum* or *Toxoplasma gondii*.

In some embodiments, a nucleic acid sequence, e.g., the first nucleic acid sequence, of the provided recombinant polynucleotide encodes a tumor-associated antigen. A tumor-associated antigen (TAA) can be derived from any cancer cell. TAAs include, but are not limited to, products of mutated oncogenes and mutated tumor suppressor genes, overexpressed or aberrantly expressed cellular proteins, antigens that are produced by oncogenic viruses, oncofetal antigens, altered cell surface glycolipids and glycoproteins, antigens that are aberrantly processed in tumor cells for presentation on MHC molecules, and antigens that are tumor cell type-specific. In some embodiments, a TAA is one that newly arises in a tumor, e.g., a subject's tumor. Such neoantigens can arise, for example, as a consequence of a tumor-specific mutation. In some embodiments, a TAA is a cell surface protein, e.g., a protein that is normally present on the surface of a cell, or a portion thereof, that is altered as a consequence of a mutation in a gene encoding the cell surface protein.

Non-limiting examples of TAAs include the melanoma-associated antigens (MAGEs). MAGE proteins contain a conserved domain that is about 200 amino acids in length and is usually located near the C-terminal end of the protein, although the conserved domain is located closer to the central portion of some MAGE proteins. Human MAGE proteins include MAGEA1, MAGEA2, MAGEA2B, MAGEA3, MAGEA4, MAGEA5, MAGEA6, MAGEA7P, MAGEA8, MAGEA9, MAGEA9B, MAGEA10, MAGEA11, MAGEA12, MAGEA13P, MAGEB1, MAGEB2, MAGEB3, MAGEB4, MAGEB5, MAGEB6, MAGEB10, MAGEB16, MAGEB17, MAGEB18, MAGEC1, MAGEC2, MAGEC3, MAGED1, MAGED2, MAGED3 (also known as "trophin" or "TRO"), MAGED4, MAGED4B, MAGEE1, MAGEE2, MAGEF1, MAGEEG1 (also known as "NSMCE3"), MAGEH1, MAGEL2, and NDN. Additional non-limiting examples of TAAs that are useful for methods of the present invention include NY-ESO-1 and prostate-specific antigen (PSA).

Other Recombinant Polynucleotide Features

In some embodiments, the first nucleic acid sequence of the provided recombinant polynucleotide, e.g., the nucleic acid sequence encoding an antigen, is codon optimized. In some embodiments, the second nucleic acid sequence of the provided recombinant polynucleotide, e.g., the nucleic acid sequence encoding an enzyme of an amino acid catabolic pathway, is codon optimized. In some embodiments, the first nucleic acid sequence and the second nucleic acid sequence of the recombinant polynucleotide are codon optimized.

As used herein, the terms "codon optimized" and "codon optimization" refer to altering a nucleic acid sequence, without changing the encoded amino acid sequence, in such a way that codon bias, i.e., the preferential use of particular codons that can vary between species, is reduced or rebalanced. In some embodiments, codon optimization increases translational efficiency, e.g., of an antigen or amino acid catabolic pathway enzyme. As a non-limiting example of codon optimization, leucine is encoded by six different codons, some of which are rarely used. By rebalancing codon usage, e.g., within a reading frame, preferred leucine codons can be selected over rarely used codons. The nucleic acid sequence encoding the protein of interest is altered such that the rarely used codons are converted to preferred codons. Codon optimization can also be used, for example, to modulate GC content, e.g., to increase mRNA stability or reduce secondary structure; or to otherwise minimize codons that may result in stretches of sequence that impair expression of the protein of interest. Rare codons, for example, can be defined and targeted for alteration through codon optimization by using a codon usage table derived from the sequenced genome of a host species, i.e., the species in which the provided recombinant polynucleotide will be expressed. See, e.g., the codon usage table obtained from Kazusa DNA Research Institute, Japan used in conjunction with software, e.g., "Gene Designer 2.0" software, from DNA 2.0 at a cut-off threshold of 15%.

In some embodiments, the provided recombinant polynucleotide includes at least one promoter sequence. In some embodiments, the recombinant polynucleotide includes a promoter sequence promoting transcription of the first nucleic acid sequence of the polynucleotide. In some embodiments, the recombinant polynucleotide includes a promoter sequence promoting transcription of the second nucleic acid sequence of the polynucleotide. In some embodiments, the recombinant polynucleotide includes a first promoter sequence promoting transcription of the first nucleic acid sequence, and a second promoter sequence promoting transcription of the second nucleic acid sequence. In some embodiments, the recombinant polynucleotide includes a promoter sequence that promotes transcription of both the first nucleic acid sequence and the second nucleic acid sequence.

At least one promoter of the recombinant polynucleotide can be, for example, a constitutive promoter, e.g., a constitutive mammalian promoter. A non-limiting example of a constitutive mammalian promoter suitable for use with the provided recombinant polynucleotide is EF1α (Wang et al., 21 J. Cell Mol. Med. 3044 (2017); Edmonds et al., 109 J. Cell Sci. 2705 (1996)). Useful promoters can also be derived from viruses or any other organism, e.g., prokaryotic or eukaryotic organisms. Promoters can also be inducible, i.e., capable of responding to environmental factors and/or external stimuli that can be artificially controlled. Additional non-limiting examples of promoters include unmodified and modified bacterial T7 promoters such as the EM7 promoter; RNA polymerase II promoters such as pGAL7 and pTEF1; RNA polymerase III promoters such as RPR-tetO, SNR52, and tRNA-tyr; the SV40 early promoter; mouse mammary tumor virus long terminal repeat (LTR) promoter; adenovirus major late promoter (Ad MLP); a herpes simplex virus (HSV) promoter; a cytomegalovirus (CMV) promoter such as the CMV immediate early promoter region (CMVIE); a rous sarcoma virus (RSV) promoter; a human U6 small nuclear promoter (U6); an enhanced U6 promoter; and a human H1 promoter (H1).

In some embodiments, the provided recombinant polynucleotide includes at least one internal ribosomal entry site sequence. In some embodiments, the provided recombinant polynucleotide includes two or more, e.g., three, four, five, six, seven, eight, nine, ten, or more than ten internal ribosomal entry site sequences.

In some embodiments, the provided recombinant polynucleotide includes at least one polyadenylation sequence. In some embodiments, the provided recombinant polynucleotide includes two or more, e.g., three, four, five, six, seven, eight, nine, ten, or more than ten polyadenylation sequences. Suitable polyadenylation sequences and terminators that can be part of the recombinant polynucleotide include, but are not limited to, SV40, hGH, BGH, rbGlob SNR52, and RPR polyadenylation and terminator sequences. Additionally, various primer binding sites can be incorporated into a vector to facilitate vector cloning, sequencing, genotyping, and the like.

In some embodiments, the provided recombinant polynucleotide is circular. In some embodiments, the provided recombinant polynucleotide is linear.

In some embodiments, the provided recombinant polynucleotide includes at least one selectable marker. A selectable marker is useful, for example, when a polynucleotide of the present invention is being recombinantly modified, especially when it is desirable to screen a population of modified polynucleotides, e.g., using bacterial, yeast, plant, or animal cells, for those that have incorporated the desired modification(s). Whether the polynucleotide is recombinantly modified within a cell, e.g., a bacterial cell, for example using Red/ET recombination, or is recombinantly modified and subsequently introduced into a cell, e.g., a bacterial, yeast, plant, or animal cell, for screening, the selectable marker can be used to identify which cells contain polynucleotides that have incorporated a modification of interest. Taking antibiotic resistance genes as an example of a selectable marker, treating the cells that contain the recombinant polynucleotides with the antibiotic will identify which cells contain recombinant polynucleotides that have incorporated the antibiotic resistance gene, i.e., which cells survive after antibiotic treatment through incorporation of the antibiotic resistance gene. If desired, the recombinant polynucleotides can be further screened, e.g., purified from the cells, amplified, and/or sequenced, in order to verify that the desired modification has been recombinantly introduced into the polynucleotide at the correct position.

When the selectable marker of the provided recombinant polynucleotide is an antibiotic resistance gene, the gene can confer resistance to, for example, chloramphenicol, phleomycin, ampicillin, kanamycin, tetracycline, or another appropriate antibiotic that will be known to one of skill in the art. In some embodiments, a selectable marker is used that produces a visible phenotype, such as the color of an organism or population of organisms. As a non-limiting example, the phenotype can be examined by growing the organisms, e.g., cells or other organisms that contain the recombinant polynucleotide, and/or their progeny under conditions that result in a phenotype, wherein the phenotype may not be visible under ordinary growth conditions.

In some embodiments, the selectable marker used for identifying cells that contain the provided recombinant polynucleotide is a fluorescently tagged protein, a chemical stain, a chemical indicator, or a combination thereof. In some embodiments, the selectable marker responds to a stimulus, a biochemical agent, or a change in environmental conditions. In some instances, the selectable marker responds to the concentration of a metabolic product, a protein product, a drug, a cellular phenotype of interest, a cellular product of interest, or a combination thereof.

The size of the provided recombinant polynucleotide will depend on, among other factors, the particular antigen(s) and catabolic enzyme pathway enzyme(s) encoded by nucleic acid sequences of the polynucleotide, the presence and choice of regulatory sequences and/or expression vectors, e.g., viral vectors, etc. The recombinant polynucleotide can have a length, for example, between 1 kilobase and 300 kilobases, e.g., between 1 kilobase and 31 kilobases, between 1.8 kilobases and 54 kilobases, between 3.1 kilobases and 96 kilobases, between 5.5 kilobases and 170 kilobases, or between 9.8 kilobases and 300 kilobases. In terms of upper limits, the recombinant polynucleotide can have a length less than 300 kilobases, e.g., less than 170 kilobases, less than 96 kilobases, less than 54 kilobases, less than 31 kilobases, less than 17 kilobases, less than 9.8 kilobases, less than 5.5 kilobases, less than 3.1 kilobases, or less than 1.8 kilobases. In terms of lower limits, the recombinant polynucleotide can have a length greater than 1 kilobase, e.g., greater than 1.8 kilobases, greater than 3.1 kilobases, greater than 5.5 kilobases, greater than 9.8 kilobases, greater than 17 kilobases, greater than 54 kilobases, greater than 96 kilobases, or greater than 170 kilobases.

Longer lengths, e.g., greater than 300 kilobases, and shorter lengths, e.g., less than 1 kilobase, are also contemplated.

Viral Particles

In another aspect, a viral particle is disclosed. The provided viral particle includes any of the recombinant polynucleotides disclosed herein and described in further detail above. In some embodiments, the viral particle includes a recombinant polynucleotide having a first nucleic acid sequence encoding an antigen, and a second nucleic acid sequence encoding an enzyme of an amino acid catabolic pathway. In some embodiments, the viral particle is one that replicates in and/or is released from an infected, transfected, or transformed host cell.

Host Cells

In another aspect, a host cell is disclosed. The provided host cell includes any of the recombinant polynucleotides disclosed herein and described in further detail above. In some embodiments, the host cell includes a recombinant polynucleotide having a first nucleic acid sequence encoding an antigen, and a second nucleic acid sequence encoding an enzyme of an amino acid catabolic pathway.

In some embodiments, the host cell includes a recombinant polynucleotide as disclosed herein and/or a viral particle as disclosed herein. In some embodiments, the host cell has been transfected or transformed by a provided recombinant polynucleotide. In some embodiments, the host cell has been infected by a provided viral particle of the present invention. In some embodiments, the host cell includes a plurality of provided recombinant polynucleotides and/or provided viral particles. In some embodiments, the host cell includes a plurality of different recombinant polynucleotides and/or viral particles. In some embodiments, a viral particle as disclosed herein is replicating inside the provided host cell.

The host cell can be any cell of interest. The cell can be a cell from any organism, e.g., a bacterial cell, a cell of a single-cell eukaryotic organism, the cell of a multicellular eukaryotic organism, a plant cell (e.g., a rice cell, a wheat cell, a tomato cell, an *Arabidopsis thaliana* cell, a *Zea mays* cell and the like), an animal cell, a cell from an invertebrate animal (e.g., fruit fly, cnidarian, echinoderm, nematode, and the like), a cell from a vertebrate animal (e.g., fish, amphibian, reptile, bird, mammal, and the like), a cell from a mammal, a cell from a human, a cell from a healthy human, a cell from a human patient, or a cell from a cancer patient. In some cases, the host cell can be transplanted to a subject. In some embodiments, the cell is derived from the subject to be treated.

Furthermore, the cell can be a stem cell, e.g., embryonic stem cell, induced pluripotent stem cell, adult stem cell, mesenchymal stem cell, neural stem cell, hematopoietic stem cell, or organ stem cell. The cell can be a progenitor cell, a somatic cell, fibroblast, epithelial cell, endothelial cell, heart cell, liver cell, pancreatic cell, muscle cell, skin cell, blood cell, neural cell, immune cell, and any other cell of the body, e.g., human body. The cell can be a primary cell or a primary cell culture derived from a subject, e.g., an animal subject or a human subject, and allowed to grow in vitro for a limited number of passages. The cell can be a healthy cell or a diseased cell. In some embodiments, the host cell is a fibroblast, e.g., telomerized fibroblast. In particular embodiments, a provided recombinant polynucleotide and/or provided viral particle is purified from the host cell.

Pharmaceutical Compositions

In another aspect, a pharmaceutical composition is disclosed. The provided pharmaceutical composition includes any of the recombinant polynucleotides disclosed herein and described in further detail above. In some embodiments, the viral particle includes a recombinant polynucleotide having a first nucleic acid sequence encoding an antigen, and a second nucleic acid sequence encoding an enzyme of an amino acid catabolic pathway.

In some embodiments, the provided pharmaceutical composition further includes a pharmaceutically acceptable carrier. In some embodiments, the provided pharmaceutical composition further includes a pharmaceutically acceptable excipient. In some embodiments, the provided pharmaceutical composition includes a pharmaceutically acceptable carrier and a pharmaceutically acceptable excipient.

The terms "pharmaceutically acceptable carrier" and "pharmaceutically acceptable excipient" refer to substances that aid the administration of an active agent to a cell, an organism, or a subject. A carrier or excipient can be included in the provided pharmaceutical compositions of the invention if causing no significant adverse toxicological effect on the patient. Non-limiting examples of pharmaceutically acceptable carriers include water, sodium chloride (NaCl), normal saline solutions, lactated Ringer's, normal sucrose, normal glucose, binders, fillers, disintegrants, lubricants, coatings, sweeteners, flavors and colors, liposomes, dispersion media, microcapsules, cationic lipid carriers, isotonic and absorption delaying agents, and the like. The pharmaceutically acceptable carrier can comprise or consist of one or more substances for providing the formulation with stability, sterility and isotonicity, e.g., antimicrobial preservatives, antioxidants, chelating agents and buffers. The pharmaceutically acceptable carrier can comprise or consist of one or more substances for preventing the growth or action of microorganisms, e.g., antimicrobial and antifungal agents, such as parabens, chlorobutanol, phenol, sorbic acid and the like. The pharmaceutically acceptable carrier can comprise or consist of one or more substances for providing the formulation with a more palatable or edible flavor. In some instances, the pharmaceutically acceptable excipient is an agent that facilitates the delivery of a polynucleotide to a target cell or tissue. One of skill in the art will recognize that other pharmaceutical carriers or excipients are useful in the present invention.

The provided pharmaceutical composition can further include one or more buffers, e.g., neutral buffered saline or phosphate buffered saline; one or more carbohydrates, e.g., glucose, mannose, sucrose or dextrans; mannitol; one or more proteins, polypeptides or amino acids such as glycine; one or more antioxidants, e.g., ascorbic acid, sodium metabisulfite, butylated hydroxytoluene, or butylated hydroxyanisole; one or more bacteriostats; one or more chelating agents, e.g., EDTA or glutathione; one or more solutes that render the formulation isotonic, hypotonic or weakly hypertonic with the blood of a recipient; one or more suspending agents; one or more thickening agents; one or more preservatives; one or more flavoring agents; one or more sweetening agents; one or more coloring compounds; or a combination thereof.

The pharmaceutical compositions disclosed herein can be provided in a desired dosage formulation, suitable, for example, to be administered in a therapeutically or prophylactically effective manner. The quantity to be administered can depend at least in part on a variety of factors including, e.g., the age, body weight, physical activity, hereditary characteristics, general health, sex, and diet of the individual subject; the condition or disease to be treated or prevented; and the stage or severity of the condition or disease. In certain embodiments, the size of the dose may also be determined by the existence, nature, and extent of any adverse side effects that accompany the administration of a therapeutic or prophylactic agent(s) in a particular individual. Other factors that can influence the specific dose level and frequency of dosage for any particular patient include the activity of the specific compound employed, the metabolic stability and length of action of that compound, the mode and time of administration, and the rate of excretion.

In some embodiments, the provided pharmaceutical compositions include an adjuvant, e.g., a compound administered to a subject in conjunction with the recombinant polynucleotide for enhancing an immune response to the antigen. Adjuvants can increase the immunogenicity of vaccines in any of a number of ways, and can include inorganic compounds such as salts, e.g., aluminum salts, as well as organic compounds and mixtures of compounds, including extracts and preparations, e.g., Freund's incomplete adjuvant, squalene, MF59, monophosphoryl lipid A, QS-21.

In some embodiments, the pharmaceutical composition dose can take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages. As used herein, the term "unit dosage form" refers to physically discrete units suitable as unitary dosages, e.g., an ampoule, for humans and other mammals with each unit containing a predetermined quantity calculated to produce the desired onset, tolerability, and/or therapeutic or prophylactic effects, in association with a suitable pharmaceutical excipient. In addition, more concentrated dosage forms may be prepared, from which the more dilute unit dosage forms may then be produced. The more concentrated dosage forms thus will contain substantially more than, e.g., at least one, two, three, four, five, six, seven, eight, nine, ten, or more than ten times the amount of the pharmaceutical composition. The dosage forms typically include a conventional pharmaceutical carrier or excipient and may additionally include other medicinal agents, carriers, adjuvants, diluents, tissue permeation enhancers, solubilizers, and the like.

Methods for Inducing an Immune Response

In another aspect, a method for inducing an immune response against an antigen in a subject is disclosed. The method includes administering to the subject a therapeutically effective amount of any of the pharmaceutical compositions, viral particles, and/or host cells disclosed herein and described in further detail above.

As used herein, the term "administering" includes oral administration, topical contact, administration as a suppository, intravenous, intraperitoneal, intramuscular, intralesional, intratumoral, intrathecal, intranasal, intraosseous, or subcutaneous administration to a subject. Administration is by any route, including parenteral and transmucosal, e.g., buccal, sublingual, palatal, gingival, nasal, vaginal, rectal, or transdermal. Parenteral administration includes, e.g., intravenous, intramuscular, intra-arterial, intradermal, subcutaneous, intraperitoneal, intraventricular, intraosseous, and intracranial. Other modes of delivery include, but are not limited to, the use of liposomal formulations, intravenous infusion, and transdermal patches.

As used herein, the term "subject" refers to a vertebrate, preferably a mammal, more preferably a human. Mammals include, but are not limited to, murines, mice, rats, simians, humans, farm animals, sport animals, and pets. Tissues, cells and their progeny of a biological entity obtained in vivo or cultured in vitro are also encompassed. In some embodiments, the subject is human. In some embodiments, the subject is male. In some embodiments, the subject is female. In some embodiments, the subject is an adult. In some embodiments, the subject is an adolescent. In some embodiments, the subject is a child. In some embodiments, the subject is above 60, 70, or 80 years of age.

As used herein, the term "therapeutically effective amount" refers to the amount of a recombinant polynucleotide or pharmaceutical composition described herein that is sufficient to effect beneficial or desired results. The therapeutically effective amount can vary depending upon one or more of the subject and disease condition being treated, the weight and age of the subject, the severity of the disease condition, the immune status of the subject, the manner of administration and the like, which can readily be determined by one of ordinary skill in the art. The specific amount can further vary depending on one or more of the particular agent chosen, the target cell type, the location of the target cell in the subject, the dosing regimen to be followed, whether the provided polynucleotide or composition is administered in combination with other compounds, the timing of administration, and the physical delivery system in which it is carried.

For the purposes herein an effective amount is determined by such considerations as may be known in the art. The amount must be effective to achieve the desired therapeutic effect in a subject suffering from a disease such as an infectious disease or cancer. The desired therapeutic effect can include, for example, amelioration of undesired symptoms associated with the disease, prevention of the manifestation of such symptoms before they occur, slowing down the progression of symptoms associated with the disease, slowing down or limiting any irreversible damage caused by the disease, lessening the severity of or curing the disease, or improving the survival rate or providing more rapid recovery from the disease. Further, in the context of prophylactic treatment the amount can also be effective to prevent the development of the disease.

The disclosed pharmaceutical compositions can be administered using the provided method as a single dose or as multiple doses, for example, two doses administered at an interval of about one month, about two months, about three months, about six months, or about 12 months. Other suitable dosage schedules can be determined by a medical practitioner. In some embodiments, additional compounds or medications can be co-administered to the subject. Such compounds or medications can be co-administered to, for example, alleviate signs or symptoms of the disease being treated, or reduce side effects caused by induction of the immune response.

In some embodiments, the immune response induced by the provided method is assessed by immunophenotyping or by characterizing specific T-cell responses from the subject, for example by using flow cytometry. In some embodiments, the immune response includes an increased production and/or activation of CD4$^+$ memory cells. In some embodiments, the immune response includes an increased ratio of the number and/or activation of CD4$^+$ cells to CD8$^+$ cells. In some embodiments, the immune response includes increased production of interleukin 10 (IL-10). In some embodiments, the immune response includes activation of the general control nonderepressible 2 (GCN2) kinase. In some embodiments, the immune response includes activation of the arylhydrocarbon receptor (AhR). In some embodiments, the immune response includes increased production of nitric oxide (NO). In some embodiments, the immune response includes increased production of spermidine.

In some embodiments, the immune response is assessed by detecting antibodies obtained from the subject, for example using an antigen binding assay such as an enzyme-linked immunosorbent assay (ELISA). In some embodiments, the immune response includes generation of antibodies that recognize the antigen encoded by the nucleic acid sequence, e.g., the first nucleic acid sequence, of the provided recombinant polynucleotide.

In some embodiments, the immune response induced by the provided method is greater than an immune response induced using a corresponding recombinant polynucleotide, e.g., a negative control recombinant polynucleotide, that does include the nucleic acid sequence, e.g., the first nucleic acid sequence, encoding the antigen, but that does not include the nucleic acid sequence, e.g., the second nucleic acid sequence, encoding the enzyme of the amino acid catabolic pathway.

In some embodiments, the provided method further includes obtaining a test sample from the subject in which the immune response is induced. The test sample can include, for example, a blood sample, a tissue sample, a urine sample, a saliva sample, a cerebrospinal fluid sample, or a combination thereof. In some embodiments, the provided method further includes determining the level of one or more biomarkers in the obtained test sample. The biomarkers can include, for example, IFNγ, tumor necrosis factor alpha, interleukin 4, interleukin 5, interleukin 6, IL-10, interleukin 12, interleukin 15, GCN2 kinase, AhR, SHP-1, SHP-2, NO, spermidine, or a combination thereof. Determining the presence or level of biomarkers(s) can be used to, as non-limiting examples, determine response to treatment or to select an appropriate composition or method for the prevention or treatment of a disease.

In some embodiments, the provided method further includes comparing the determined level of the one of more biomarkers in the obtained test sample to the level of the one or more biomarkers in a reference sample. The reference sample can be obtained, for example, from the subject in which the immune response is induced, with the reference sample being obtained prior to the obtaining of the test sample, e.g., prior to the administering to the subject of the therapeutically effective amount of the provided pharmaceutical composition. In this way, the reference sample can provide information about baseline levels of the biomarkers in the sample before the immune response against the antigen is induced in the subject, and the test sample can provide information about levels of the biomarkers after the immune response is induced.

Alternatively, the reference sample can be obtained, for example, from a different subject, e.g., a subject in which the immune response against the antigen is not induced according to the provided method. In this way, the reference sample can provide information about baseline levels of the biomarkers without immune response inducement, and the test sample can provide information about levels of the biomarkers with immune response inducement. The reference sample can also be obtained, for example, from a population of subjects, e.g., subjects in which the immune response against the antigen is not induced according to the provided method. In this way, the reference sample can provide population-averaged information about baseline levels of the biomarkers without immune response inducement, and the test sample can provide information about levels of the biomarkers with immune response inducement.

The reference sample can also be obtained from an individual or a population of individuals after an immune response against the antigen is induced, and can serve as, for example, a positive control sample. In some embodiments, the reference sample is obtained from normal tissue. In some embodiments, the reference sample is obtained from abnormal tissue.

Depending on the biomarker, an increase or a decrease relative to a normal control or reference sample can be indicative of the presence of a disease, or response to treatment for a disease. In some embodiments, an increased level of a biomarker in a test sample, and hence the presence of a disease, e.g., an infectious disease or cancer, increased risk of the disease, or response to treatment is determined when the biomarker levels are at least, 1.1-fold, e.g., at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, or at least 20-fold higher in comparison to a negative control. In other embodiments, a decreased level of a biomarker in the test sample, and hence the presence of the disease, increased risk of the disease, or response to treatment is determined when the biomarker levels are at least 1.1-fold, e.g., at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, or at least 20-fold lower in comparison to a negative control.

The biomarker levels can be detected using any method known in the art, including the use of antibodies specific for the biomarkers. Exemplary methods include, without limitation, polymerase chain reaction (PCR), Western Blot, dot blot, ELISA, radioimmunoassay (MA), immunoprecipitation, immunofluorescence, FACS analysis, electrochemiluminescence, and multiplex bead assays, e.g., using Luminex or fluorescent microbeads. In some instances, nucleic acid sequencing is employed.

In certain embodiments, the presence of decreased or increased levels of one or more biomarkers is indicated by a detectable signal, e.g., a blot, fluorescence, chemiluminescence, color, or radioactivity, in an immunoassay or PCR reaction, e.g., quantitative PCR. This detectable signal can be compared to the signal from a reference sample or to a threshold value.

In some embodiments, the results of the biomarker level determinations are recorded in a tangible medium. For example, the results of diagnostic assays, e.g., the observation of the presence or decreased or increased presence of one or more biomarkers, and the diagnosis of whether or not there is an increased risk or the presence of a disease, e.g., an infectious disease or cancer, or whether or not a subject is responding to treatment can be recorded, for example, on paper or on electronic media, e.g., audio tape, a computer disk, a CD-ROM, or a flash drive.

In some embodiments, the provided method further includes the step of providing to the subject a diagnosis and/or the results of treatment.

Methods for Disease Prevention or Treatment

In another aspect, a method for preventing or treating a disease in a subject is disclosed. The method includes administering to the subject a therapeutically effective amount of any of the pharmaceutical compositions disclosed herein and described in further detail above. As used herein, the term "treating" refers to an approach for obtaining beneficial or desired results including, but not limited to, a therapeutic benefit and/or a prophylactic benefit. "Therapeutic benefit" means any therapeutically relevant improvement in or effect on one or more diseases, conditions, or symptoms under treatment. Therapeutic benefit can also mean to effect a cure of one or more diseases, conditions, or symptoms under treatment. Furthermore, therapeutic benefit can also refer to an increase in survival. For prophylactic benefit, the compositions can be administered to a subject at risk of developing a particular disease, condition, or symptom, or to a subject reporting one or more of the physiological symptoms of a disease, even though the disease, condition, or symptom may not yet be present.

In some embodiments, the disease prevented or treated with the provided method can be any of those described herein. The disease can be, for example, an infectious disease or cancer. The infectious disease can be any of those described herein. The infectious disease can be caused by, for example, a bacterial infection, a viral infection, a fungal infection, a protozoal infection, a helminthic infection, or a combination thereof. In some embodiments, the treating of the disease in the subject includes decreasing or eliminating one or more signs or symptoms of the disease.

As used herein, the term "cancer" refers to any of various malignant neoplasms characterized by the proliferation of anaplastic cells that tend to invade surrounding tissue and metastasize to new body sites. Non-limiting examples of different types of cancer suitable for treatment using the methods and compositions disclosed herein include colorectal cancer, colon cancer, anal cancer, liver cancer, ovarian cancer, breast cancer, lung cancer, bladder cancer, thyroid cancer, pleural cancer, pancreatic cancer, cervical cancer, prostate cancer, testicular cancer, bile duct cancer, gastrointestinal carcinoid tumors, esophageal cancer, gall bladder cancer, rectal cancer, appendix cancer, small intestine cancer, stomach (gastric) cancer, renal cancer such as renal cell carcinoma, cancer of the central nervous system, skin cancer, oral squamous cell carcinoma, choriocarcinomas, head and neck cancers, bone cancer, osteogenic sarcomas, fibrosarcoma, neuroblastoma, glioma, melanoma, leukemia (acute lymphocytic leukemia, chronic lymphocytic leukemia, acute myelogenous leukemia, chronic myelogenous leukemia, or hairy cell leukemia), lymphoma (non-Hodgkin's lymphoma, Hodgkin's lymphoma, B-cell lymphoma, or Burkitt's lymphoma), and multiple myeloma.

The provided methods can be used to treat cancer at any stage. In some embodiments, the cancer is an advanced cancer. In some embodiments, the cancer is a metastatic cancer. In some embodiments, the cancer is a drug-resistant cancer.

Kits

In another aspect, a kit is provided. The kit includes any of the pharmaceutical compositions disclosed herein and described in further detail above. In some embodiments, the kit further includes a pharmaceutically acceptable carrier, excipient, and/or adjuvant. In some embodiments, the kit is useful for inducing an immune response against the antigen encoded by a nucleic acid sequence, e.g., the first nucleic acid sequence, of the recombinant polynucleotide of the pharmaceutical composition.

The provided kit can be packaged in a way that allows for safe or convenient storage or use. The kit can be packaged, for example, in a box or other container having a lid. Typically, the provided kit includes one or more containers, with each container storing a particular kit component such as, for example, a reagent or a control sample. The choice of container will depend on the particular form, e.g., liquid form, solid form, suspension form, or powder form, of its contents. Furthermore, containers can be made of materials that are designed to maximize the shelf-life of the kit components. As a non-limiting example, kit components that are light-sensitive can be stored in containers that are opaque.

In some embodiments, the provided kit contains one or more elements, e.g., a syringe, useful for administering the disclosed pharmaceutical composition to a subject, e.g., using a provided method. In some embodiments, the kit further includes one or more elements, e.g., test tubes or slides, useful for obtaining and/or processing one or more samples obtained from the subject. In some embodiments, the kit further includes instructions for use, e.g., containing directions for the practice of a provided method. While the instructional materials typically include written or printed materials they are not limited to such. Any medium capable of storing such instructions and communicating them to an end user is contemplated by this invention. Such media include, but are not limited to electronic storage media, e.g., magnetic discs, tapes, cartridges, chips; optical media, e.g., CD-ROM; and the like. Such media can include addresses to internet sites that provide such instructional materials.

EMBODIMENTS

The following embodiments are contemplated. All combinations of features and embodiment are contemplated.

Embodiment 1: A recombinant polynucleotide comprising: a first nucleic acid sequence encoding an antigen; and a second nucleic acid sequence encoding an enzyme of an amino acid catabolic pathway.

Embodiment 2: An embodiment of embodiment 1, wherein the amino acid catabolic pathway is an L-tryptophan catabolic pathway.

Embodiment 3: An embodiment of embodiment 2, wherein the enzyme of the L-tryptophan catabolic pathway is indoleamine 2,3-dioxygenase 1 or a paralogue or isoform thereof.

Embodiment 4: An embodiment of embodiment 2, wherein the enzyme of the L-tryptophan catabolic pathway is indoleamine 2,3-dioxygenase 2 or a paralogue or isoform thereof.

Embodiment 5: An embodiment of embodiment 2, wherein the enzyme of the L-tryptophan catabolic pathway is tryptophan 2,3-dioxygenase or a paralogue or isoform thereof.

Embodiment 6: An embodiment of embodiment 1, wherein the amino acid catabolic pathway is an L-arginine catabolic pathway.

Embodiment 7: An embodiment of embodiment 6, wherein the enzyme of the L-arginine catabolic pathway is arginase 1 or a paralogue or isoform thereof.

Embodiment 8: An embodiment of embodiment 6, wherein the enzyme of the L-arginine catabolic pathway is nitric oxide synthase 2 or a paralogue or isoform thereof.

Embodiment: An embodiment of embodiment 1, wherein the enzyme is interleukin 4-induced gene 1.

Embodiment 10: An embodiment of embodiment 1, wherein the enzyme is an L-amino acid oxidase.

Embodiment 11: An embodiment of any of the embodiments of embodiment 1-10, wherein the antigen comprises a viral nucleoprotein.

Embodiment 12: An embodiment of any of the embodiments of embodiment 1-10, wherein the antigen comprises a secreted protein.

Embodiment 13: An embodiment of any of the embodiments of embodiment 1-12, wherein the antigen comprises an infectious disease antigen.

Embodiment 14: An embodiment of embodiment 13, wherein the infectious disease antigen is a bacterial antigen, a viral antigen, a fungal antigen, a protozoal antigen, a helminthic antigen, or a combination thereof.

Embodiment 15: An embodiment of embodiment 13, wherein the infectious disease antigen is a severe acute respiratory syndrome coronavirus (SARS-CoV) antigen, a severe acute respiratory syndrome coronavirus 2 (SARS-CoV-2) antigen, a Middle East respiratory syndrome coronavirus (MERS-CoV) antigen, a simian immunodeficiency virus (SIV) antigen, a human immunodeficiency virus (HIV) antigen, a hepatitis C virus antigen, a herpes simplex virus antigen, an Epstein-Barr virus antigen, a cytomegalovirus antigen, an influenza virus antigen, or a combination thereof.

Embodiment 16: An embodiment of embodiment 13, wherein the infectious disease antigen is an SIV group-specific antigen (gag) protein, an HIV gag protein, or a combination thereof.

Embodiment 17: An embodiment of embodiment 13, wherein the infectious disease antigen is a bacterial disease antigen from *Mycobacterium tuberculosis, Borrelia burgdorferi, Brucella abortus, Listeria monocytogenes, Chlamydia trachomatis, Coxiella burnetii, Salmonella enterica, Francisella tularensis*, or *Rickettsia* spp.

Embodiment 18: An embodiment of embodiment 13, wherein the infectious disease antigen is a protozoal disease antigen from *Plasmodium falciparum* or *Toxoplasma gondii*.

Embodiment 19: An embodiment of any of the embodiments of embodiment 1-12, wherein the antigen comprises a tumor-associated antigen.

Embodiment 20: An embodiment of embodiment 19, wherein the tumor-associated antigen is a prostate-specific antigen, melanoma-associated antigen 4 (MAGEA4), melanoma-associated antigen 10 (MAGEA10), New York esophageal squamous cell carcinoma 1 (NY-ESO-1), a neoantigen, or a combination thereof.

Embodiment 21: An embodiment of any of the embodiments of embodiment 1-20, wherein at least one of the first nucleic acid sequence and the second nucleic acid sequence is codon optimized.

Embodiment 22: An embodiment of any of the embodiments of embodiment 1-21, further comprising: at least one promoter sequence.

Embodiment 23: An embodiment of any of the embodiments of embodiment 1-22, further comprising: at least one internal ribosome entry site sequence.

Embodiment 24: An embodiment of any of the embodiments of embodiment 1-23, further comprising: at least one polyadenylation sequence.

Embodiment 25: A viral particle comprising the recombinant polynucleotide of an embodiment of any of the embodiments of embodiment 1-24.

Embodiment 26: A host cell comprising the recombinant polynucleotide of an embodiment of any of the embodiments of embodiment 1-24.

Embodiment 27: A pharmaceutical composition comprising: the recombinant polynucleotide of an embodiment of any of the embodiments of embodiment 1-24; and a pharmaceutically acceptable carrier, a pharmaceutically acceptable excipient, or a combination thereof.

Embodiment 28: A method for inducing an immune response against an antigen in a subject, the method comprising: administering to the subject a therapeutically effective amount of the pharmaceutical composition of embodiment 27.

Embodiment 29: An embodiment of embodiment 28, wherein the subject has a previously existing immune response to the antigen.

Embodiment 30: An embodiment of embodiment 28 or 29, wherein the immune response comprises increased production of CD4+ memory cells.

Embodiment 31: An embodiment of any of the embodiments of embodiment 28-30, wherein the immune response comprises an increased ratio of CD4+ cells to CD8+ cells.

Embodiment 32: An embodiment of any of the embodiments of embodiment 28-31, wherein the immune response comprises increased production of T memory stem cells.

Embodiment 33: An embodiment of any of the embodiments of embodiment 28-32, wherein the immune response comprises increased production of interleukin 10 (IL-10).

Embodiment 34: An embodiment of any of the embodiments of embodiment 28-33, wherein the immune response comprises activation of the general control nonderepressible 2 (GCN2) kinase.

Embodiment 35: An embodiment of any of the embodiments of embodiment 28-34, wherein the immune response comprises activation of the arylhydrocarbon receptor (AhR).

Embodiment 36: An embodiment of any of the embodiments of embodiment 28-35, wherein the immune response comprises increased production of nitric oxide (NO).

Embodiment 37: An embodiment of any of the embodiments of embodiment 28-36, wherein the immune response comprises increased production of spermidine.

Embodiment 38: An embodiment of any of the embodiments of embodiment 28-37, wherein the immune response induced in the subject is greater than an immune response induced using a corresponding recombinant polynucleotide that does not comprise the second nucleic acid sequence.

Embodiment 39: An embodiment of any of the embodiments of embodiment 28-38, wherein the immune response comprises generation of antibodies that recognize the antigen.

Embodiment 40: An embodiment of any of the embodiments of embodiment 28-39, further comprising: obtaining a test sample from the subject.

Embodiment 41: An embodiment of embodiment 40, wherein the test sample comprises a blood sample, a tissue sample, a urine sample, a saliva sample, a cerebrospinal fluid sample, or a combination thereof.

Embodiment 42: An embodiment of embodiment 40 or 41, further comprising: determining the level of one or more biomarkers in the test sample.

Embodiment 43: An embodiment of embodiment 42, wherein the one or more biomarkers comprise C-reactive protein, IFNγ, tumor necrosis factor alpha, interleukin 4, interleukin 5, interleukin 6, IL-10, interleukin 12, interleukin 15, GCN2 kinase, AhR, SHP-1, SHP-2, NO, spermidine, or a combination thereof.

Embodiment 44: An embodiment of embodiment 42 or 43, further comprising: comparing the level of the one or more biomarkers in the test sample to the level of the one or more biomarkers in a reference sample.

Embodiment 45: An embodiment of embodiment 44, wherein the reference sample was obtained from the subject prior to the obtaining of the test sample.

Embodiment 46: An embodiment of embodiment 44, wherein the reference sample is obtained from a different subject or from a population of subjects.

Embodiment 47: A method for preventing or treating a disease in a subject, the method comprising administering to the subject a therapeutically effective amount of the pharmaceutical composition of embodiment 27.

Embodiment 48: An embodiment of embodiment 47, wherein the disease is an infectious disease or a cancer.

Embodiment 49: An embodiment of embodiment 48, wherein the infectious disease is caused by a bacterial infection, a viral infection, a fungal infection, a protozoal infection, a helminthic infection, or a combination thereof.

Embodiment 50: An embodiment of embodiment 48, wherein the infectious disease is caused by a SARS-CoV virus, a SARS-CoV-2 virus, a MERS-CoV virus, an SIV virus, an HIV virus, a hepatitis C virus, a herpes simplex virus, an Epstein-Barr virus, a cytomegalovirus antigen, an influenza virus antigen, or a combination thereof.

Embodiment 51: An embodiment of embodiment 48, wherein the infectious disease is caused by *Mycobacterium tuberculosis, Borrelia burgdorferi, Brucella abortus, Listeria monocytogenes, Chlamydia trachomatis, Coxiella burnetii, Salmonella enterica, Francisella tularensis*, or *Rickettsia* spp.

Embodiment 52: An embodiment of embodiment 48, wherein the infectious disease is caused by a protozoal disease antigen from *Plasmodium falciparum* or *Toxoplasma gondii*.

Embodiment 53: An embodiment of any of the embodiments of embodiment 47-52, wherein the treating of the disease comprises decreasing or eliminating one or more signs or symptoms of the disease.

EXAMPLES

The present disclosure will be better understood in view of the following non-limiting examples. The following examples are intended for illustrative purposes only and do not limit in any way the scope of the present invention.

Figure 2:
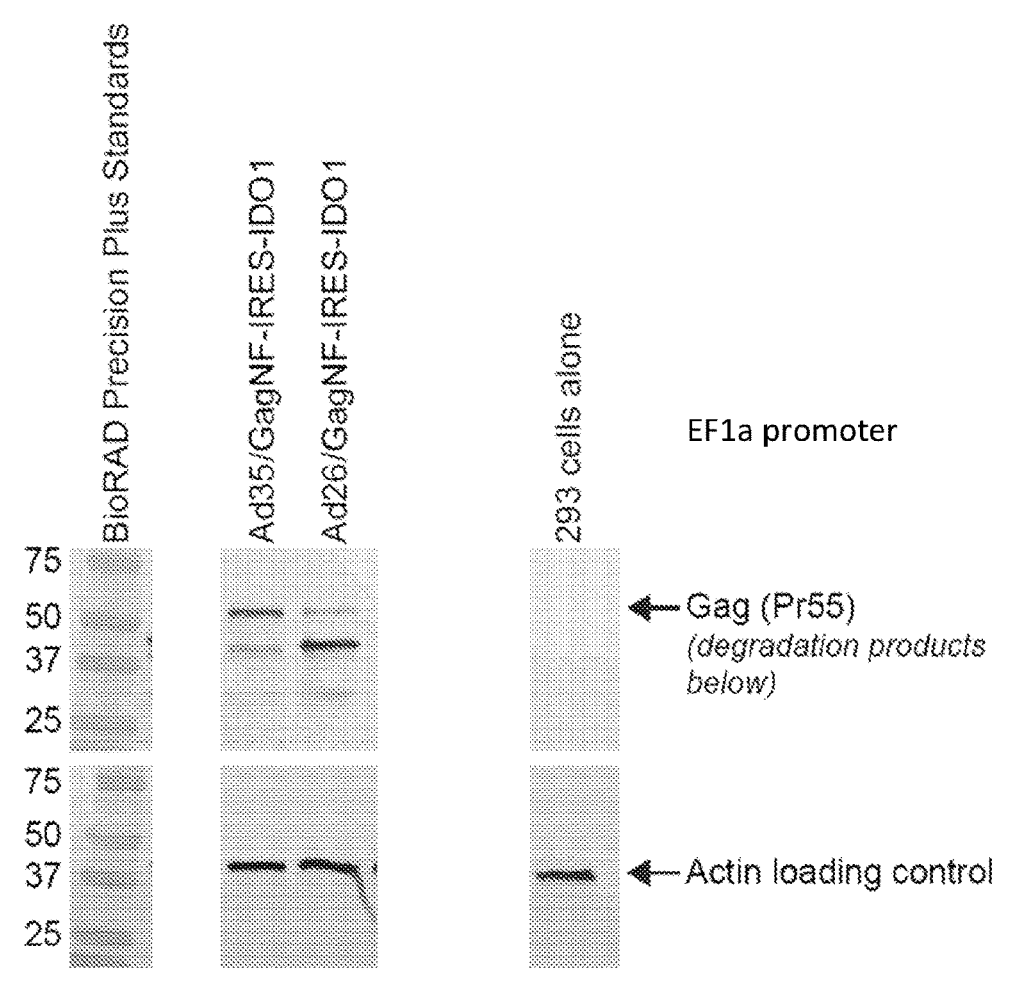
FIG. 2 is an image showing expression of vaccine antigens in vaccines expressing the antigen together with indoleamine 2,3-dioxygenase (IDO1), a tryptophan-catabolizing enzyme. Lanes 2 and 3 show expression of the vaccine antigen, SIV Gag, in vaccines that also express rhesus macaque IDO1. Ad26/GagNF-IRES-IDO1 is based on vectorized adenovirus type 26; Ad35/GagNF-IRES-IDO1 is based on vectorized adenovirus type 35. Both vaccines carry a Gag coding region, followed by an internal ribosomal entry site (IRES), followed by the rhesus macaque IDO1 coding region.

Example 1. Strong, Durable CD4-Focused Responses after Ad-Gag-IRES-IDO1 Vaccination Ad5- and Ad26-vectored vaccines were created carrying a bicistronic expression cassette to drive production of both the SIV Gag gene (a model antigen) and IDO1 (FIG. 1; SEQ ID NO:1). Briefly, the wild-type Ad genomes were "vectorized," with deletion of the E1 and E3 regions and, in the case of Ad26, and replacement of the E4orf6 ORF with the equivalent ORF from Ad5. These manipulations resulted in Ad5 and Ad26 vectors that were capable of growth to high titer in conventional 293 cells that express the E1A and E1B proteins from Ad5. The bicistronic message was then created by recombinant PCR from three components, i.e., a synthetic, codon-optimized SIV Gag ORF; a synthetic internal ribosomal entry site from encephalomyocarditis virus (ECMV); and the rhesus macaque IDO1 ORF amplified from blood cells. The resulting vectors were demonstrated to express Gag protein by western blot (FIG. 2).

Figure 3:
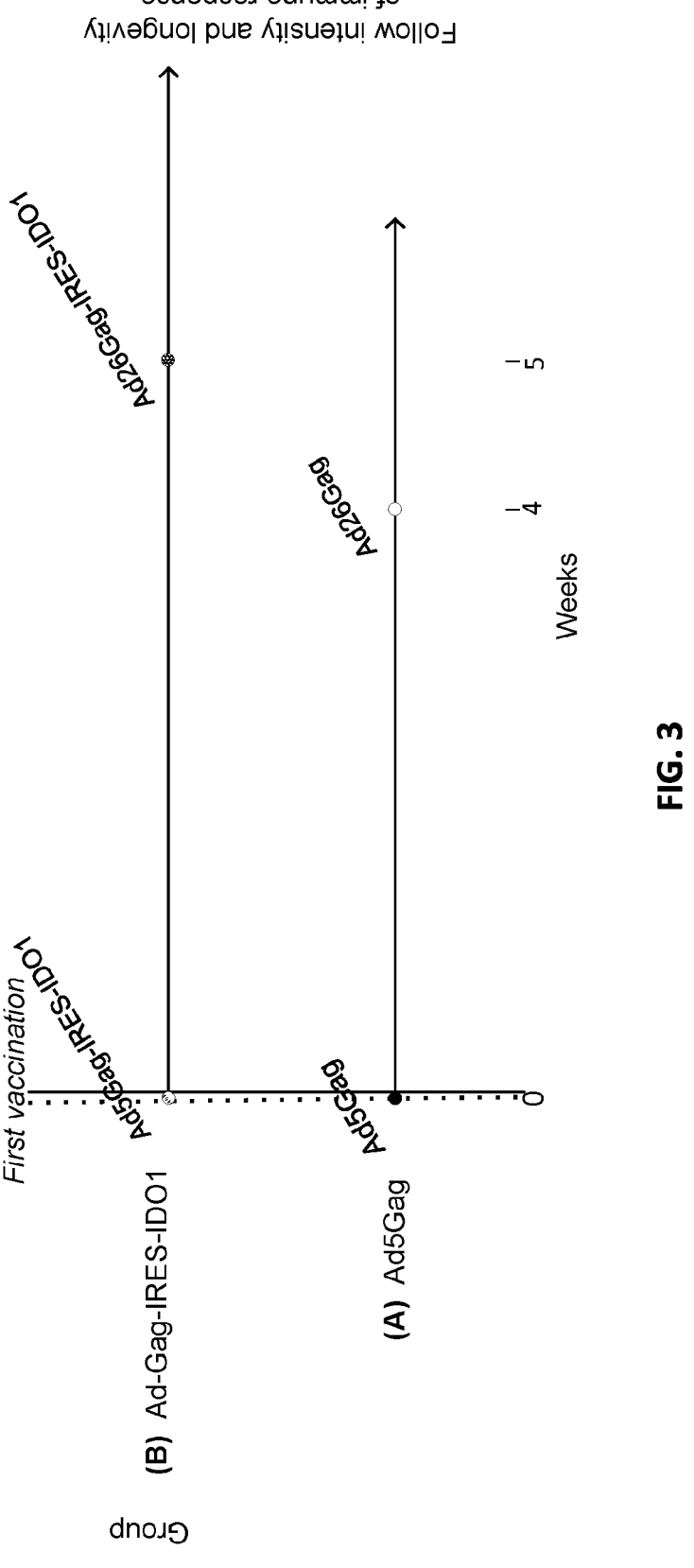
FIG. 3 is an illustration of an experimental design for comparison of immune responses to Ad-Gag (group A) or Ad-Gag-IRES-IDO1 (group B). We prepared Ad5- and Ad26-based versions of each vaccine, which were administered at 0 and 28 days (group A) or 0 and 35 days (group B).
Figure 4:
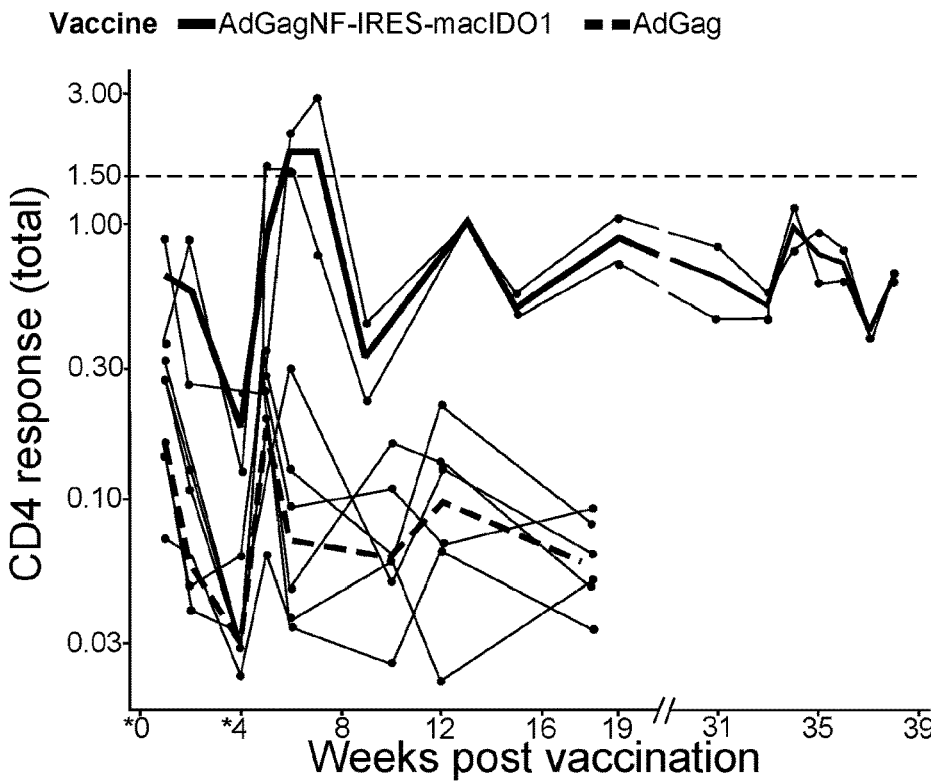
FIG. 4 is a graph showing a strong immune responses among CD4$^+$ T cells to Ad-Gag-IRES-IDO vaccination. Fainter, thinner lines represent responses from individual vaccinated rhesus macaques; darker, thicker lines represent median responses. The graph presents frequencies of CD4$^+$ T cells producing IFNγ and/or TNFα after stimulation with overlapping peptides from the vaccine antigen, SIV Gag. Responses in Ad-Gag-IRES-IDO recipients are both stronger and more durable.
Figure 5:
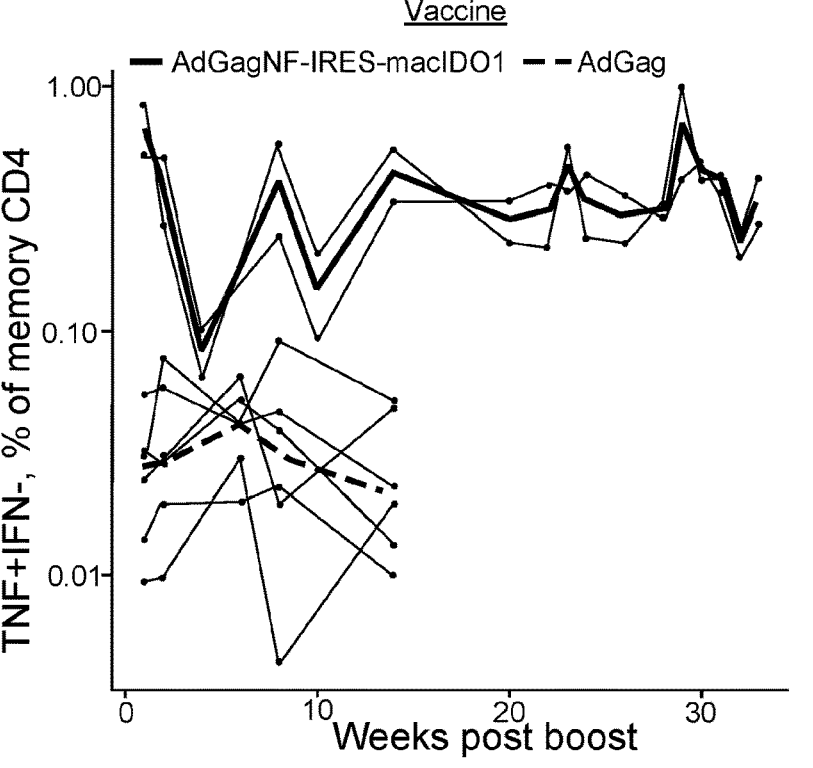
FIG. 5 is a graph showing the appearance of CD4$^+$ T cells that express TNFα without IFNγ only among Ad-Gag-IRES-IDO recipients. Cells expressing TNFα alone in response to stimulation with vaccine antigen are rare in recipients of prior adenoviral vectors but easily detected in Ad-Gag-IRES-IDO recipients.
Figure 6:
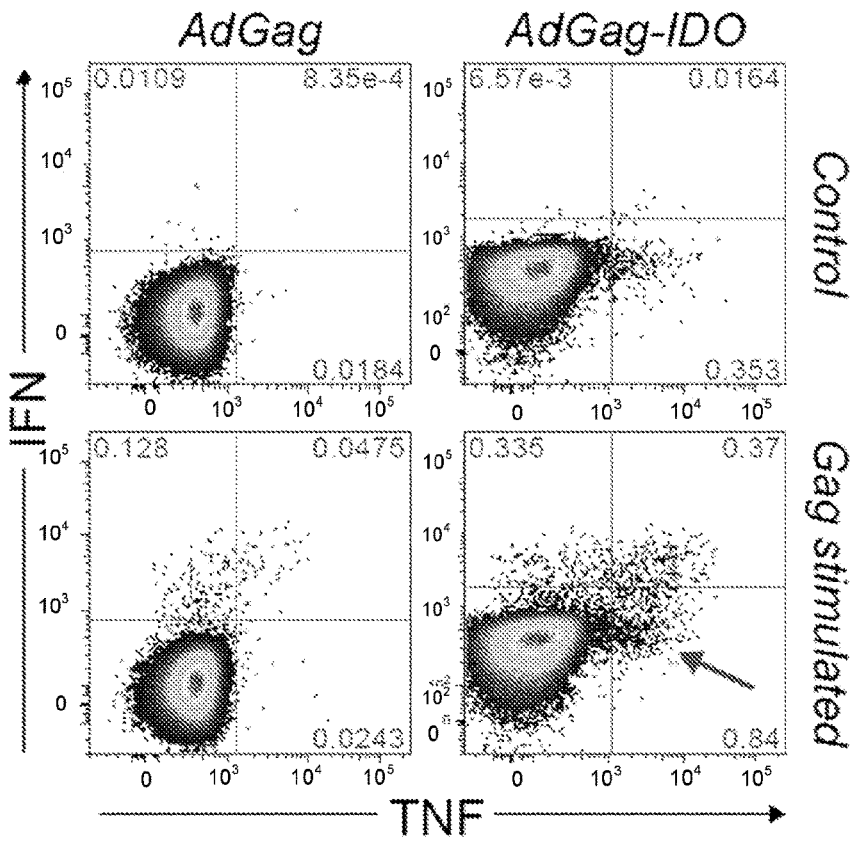
FIG. 6 presents plots showing the appearance of CD4$^+$ T cells that express TNFα without IFNγ only among Ad-Gag-IRES-IDO recipients. The cells of interest express TNFα but not IFNγ (lower right quadrant, marked by arrow). All vaccine recipients shown demonstrate a clear response to vaccine antigen. Only Ad-Gag-IRES-IDO recipients (rightmost column) show responsive cells expressing TNFα alone.
Figure 7:
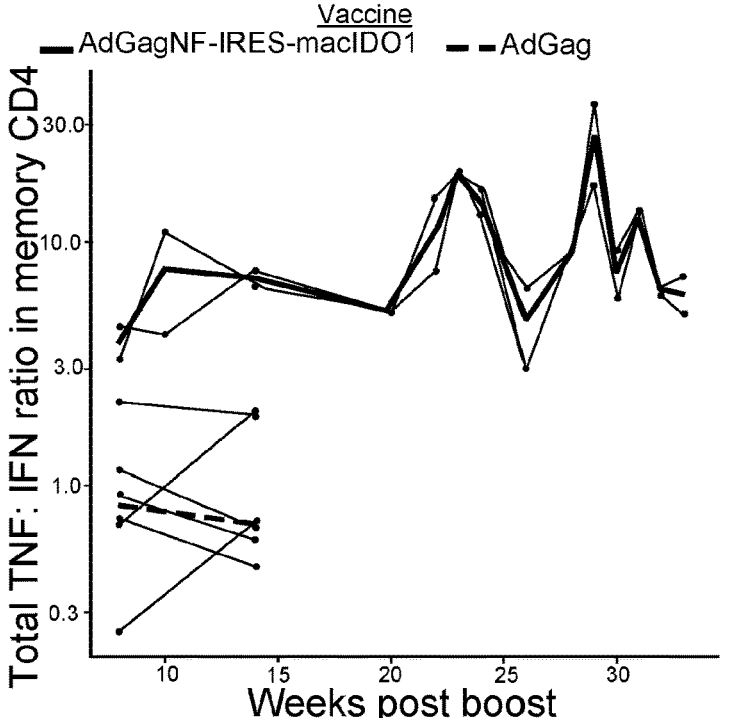
FIG. 7 is a graph showing increased ratio of TNFα expression to IFNγ expression in the vaccine antigen-responsive T cells of Ad-Gag-IRES-IDO recipients. The graph presents the ratio of CD4$^+$ T cells that made TNFα to those that made IFNγ only, when stimulated with overlapping peptides from the vaccine antigen, SIV Gag.
Figure 8:
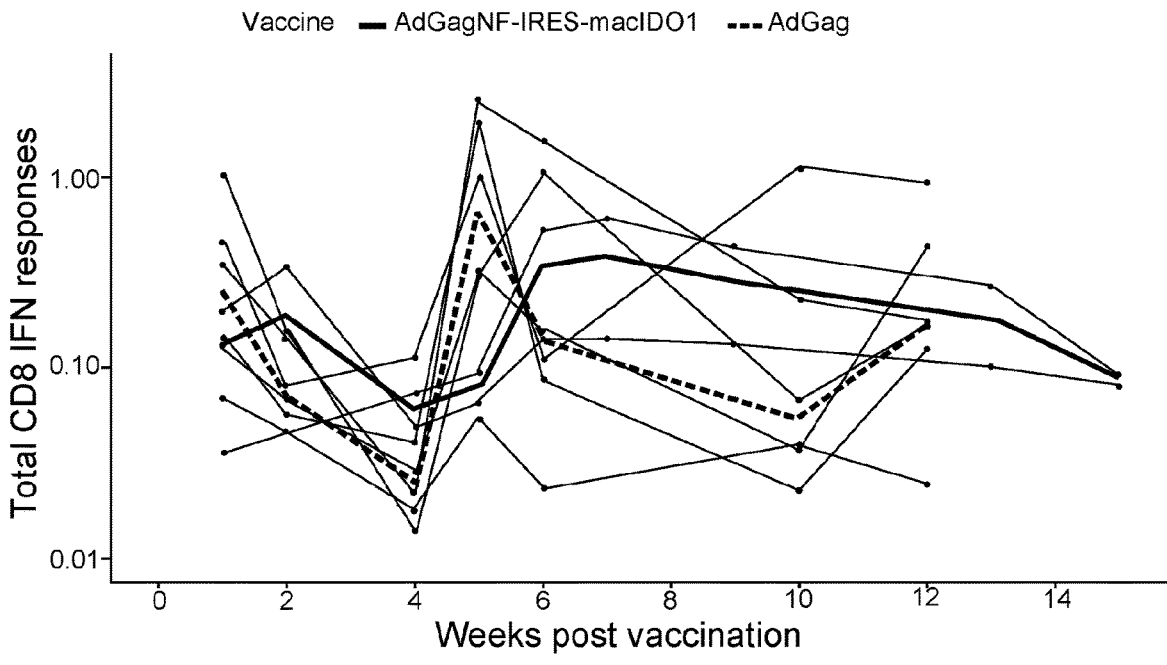
FIG. 8 is a graph showing comparable CD8$^+$ T-cell responses to vaccine antigen in recipients of Ad-Gag or Ad-Gag-IRES-IDO.
Figure 9:
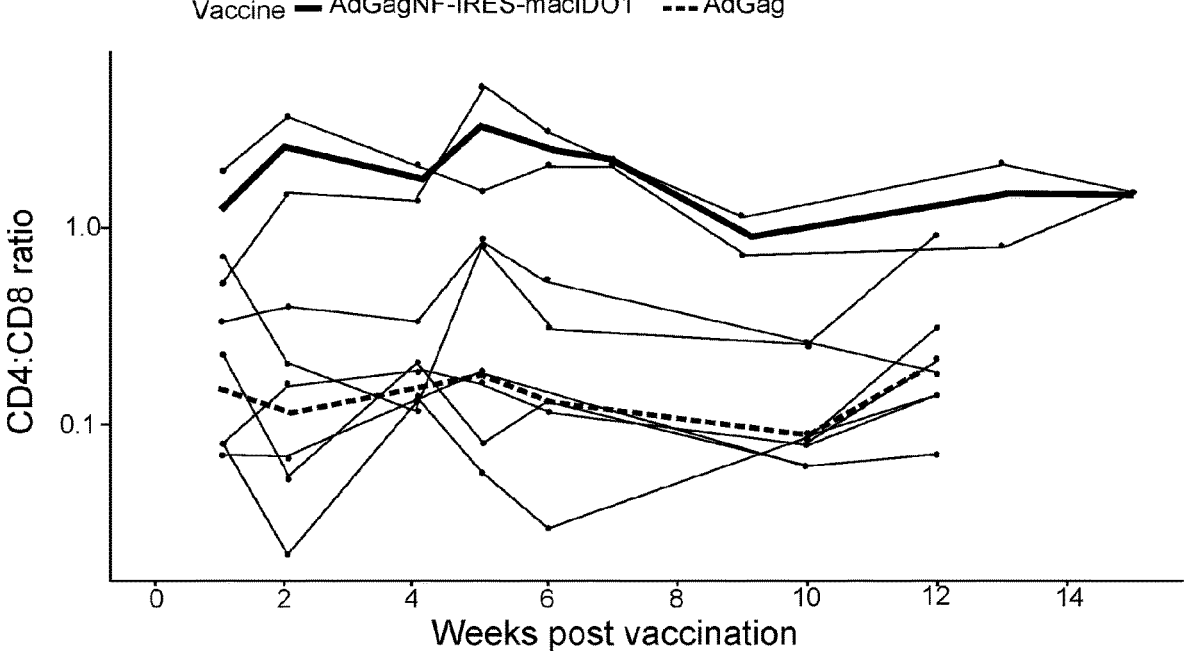
FIG. 9 is a graph showing increased ratio of vaccine antigen-specific CD4$^+$ T cells to CD8$^+$ T cells among Ad-Gag-IRES-IDO recipients. Conventional adenovirus-vectored vaccine (Ad-Gag) produces more responses among CD8$^+$ than CD4$^+$ T cells, resulting in CD4:CD8 ratios that are usually below 1 (dashed line). IDO-expressing vaccines produce a response that is concentrated in the CD4 compartment, resulting in a CD4:CD8 ratio that is usually greater than 1 (solid line).

These vectors were then prepared at medium scale in 293 cells and purified on cesium chloride gradients. Two groups of macaques were then injected with the following vaccines and their immune responses followed: (A) conventional adenoviral vectors (n=6), or (B) Ad-Gag-IRES-IDO1 (n=2; FIG. 3). Assessing T-cell responses to Ad-Gag-IRES-IDO1 (group B) revealed several remarkable and useful features of the response. Responses in the CD4 compartment were unusually strong, as compared to group A, peaking at >1.5%, a level not reached by any of the other 6 animals receiving previously described adenoviral vectors (FIG. 4). In addition, at all time points following boost, Ad-Gag-IRES-IDO vaccination produced a unique population of antigen-specific CD4$^+$ T cells expressing only TNFα, not seen in the other group (FIGS. 5 and 6). Animals receiving Ad-Gag-IRES-IDO had a general tendency to TNFα-skewed responses, as the ratio of cells expressing TNF to those expressing IFN was higher for these animals than for recipients of the other vector (FIG. 7). Most importantly, perhaps, the elicited responses were durable: whereas responses in group A declined markedly in the 18 weeks following vaccination, those in group B (receiving Ad-Gag-IRES-IDO1) persisted without significant decline for at least 39 weeks (average 0.65% at 39 weeks; FIG. 4). The CD8$^+$ T-cell responses in group B were comparable to those in the other group (FIG. 8), and as a result the ratio of responding CD4:CD8$^+$ T cells was significantly greater (FIG. 9).

Example 2. Ad-SARS2N-IRES-IDO1 Preparation and Vaccination

Figures 10, 11:
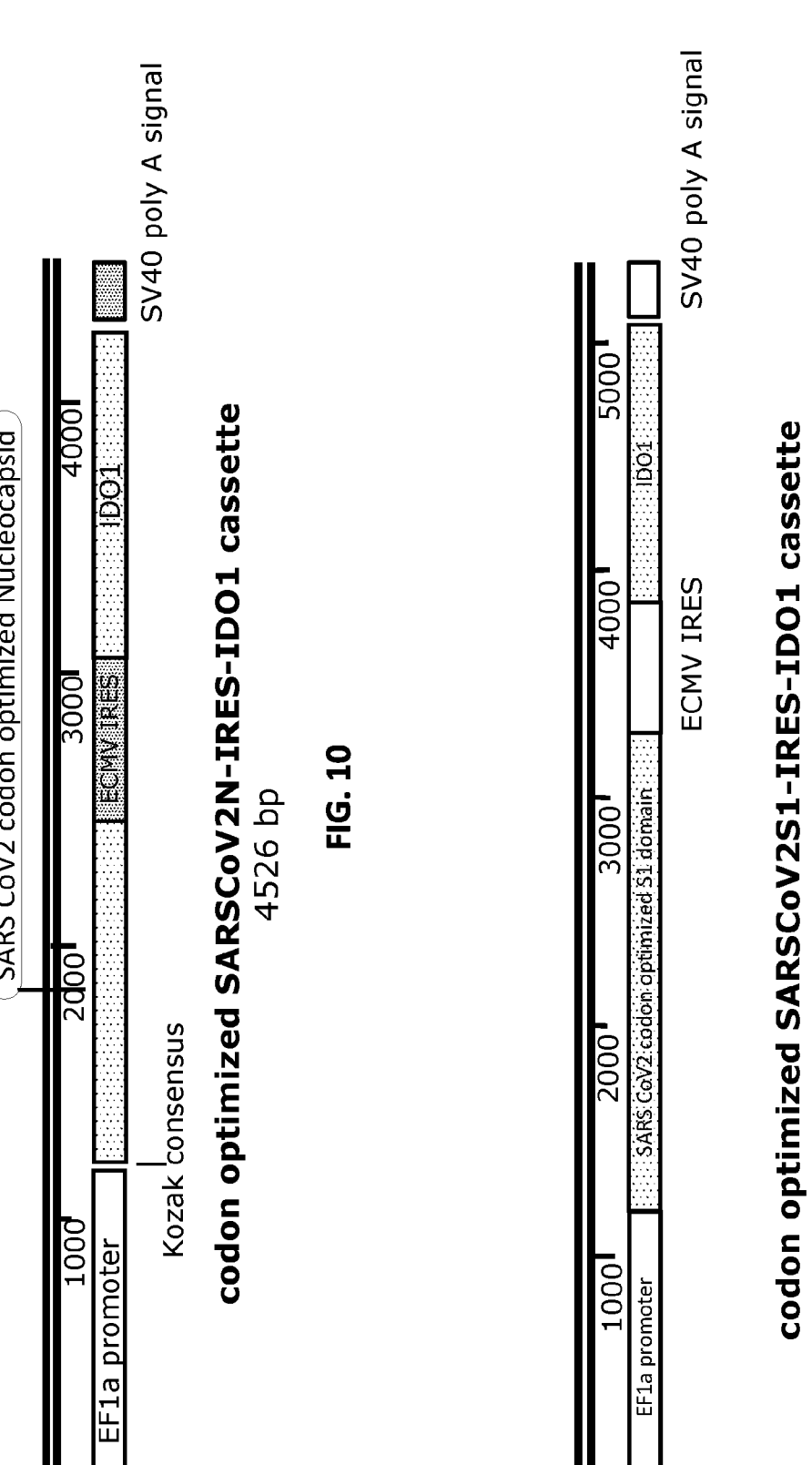
FIG. 10 is an illustration of a bicistronic expression cassette for driving production of both SARS-CoV-2 nucleoprotein (N) and indoleamine 2,3-dioxygenase in cells. Ad-SARSCoV2N-IRES-IDO1 vaccine contains this cassette in "vectorized" adenoviruses. Expression of the bicistronic transcript is driven by a human EF1α promoter containing the first intron; the coding regions for SARS-CoV-2 nucleoprotein and IDO1 are separated by an ECMV internal ribosomal entry site; and the cassette is terminated by an SV40 virus polyadenylation signal.
FIG. 11 illustrates a bicistronic expression cassette for driving production of both SARS-CoV-2 spike domain 1 (S1) and indoleamine 2,3-dioxygenase in cells. Ad-SARSCoV2S1-IRES-IDO1 vaccine contains this cassette in "vectorized" adenoviruses. Expression of the bicistronic transcript is driven by a human EF1α promoter containing the first intron, the coding regions for SARS-CoV-2 Si and IDO1 are separated by an ECMV internal ribosomal entry site, and the cassette is terminated by an SV40 virus polyadenylation signal.
Figure 13:
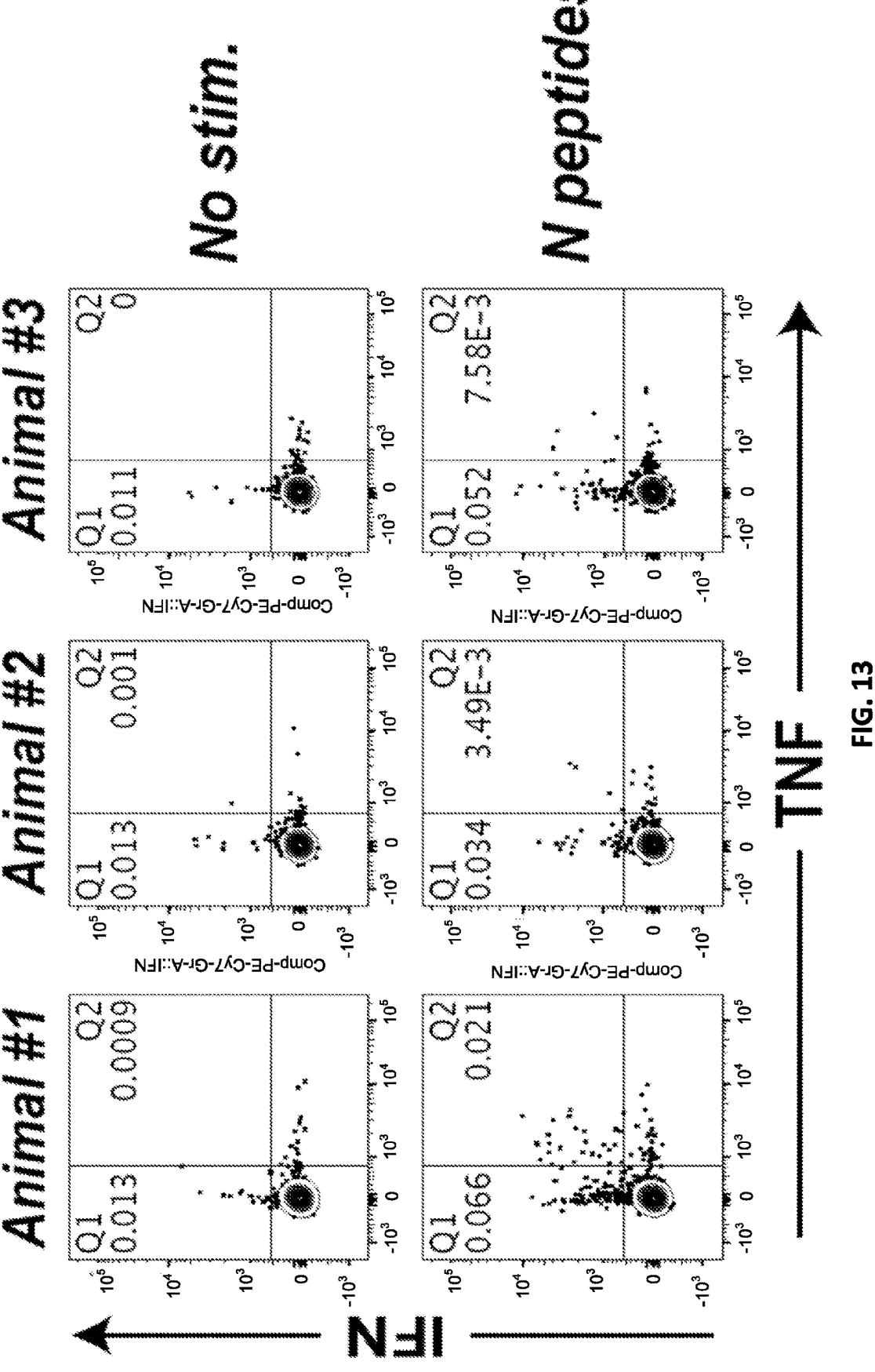
FIG. 13 demonstrates immune responses to Ad26-SARSCoV2N-IRES-IDO1 ($10^{12}$ vector particles IM) detected in CD4$^+$ T cells two weeks after immunization. Three animals were vaccinated and all developed responses, as indicated by detection of few or no cells producing cytokine without stimulation (top row), but a significant number produced cytokine after stimulation with overlapping peptides from SARS-CoV-2 nucleocapsid (bottom row).

CD4$^+$ T-cell responses were demonstrated necessary for protection against SARS-CoV and MERS-CoV in an animal model (J. Zhao et al., 44 Immunity 1379 (2016)). Because IDO1-expressing vaccines provoke such strong immune responses in the CD4 compartment, we created IDO1-expressing Ad26 and Ad35 vaccines that express the nucleoprotein from SARS-CoV-2 (SEQ ID NO:2). Ad35 was vectorized by deletion of the E1 and E3 regions and replacement of the endogenous E4orf6 with that from Ad5, as described above for Ad26 vaccines. Ad26 and Ad35 backbones were then engineered to contain a bicistronic expression cassette for SARS-CoV-2 nucleoprotein (codon optimized) and rhesus macaque IDO1, separated by an ECMV IRES (FIG. 10; SEQ ID NO:3). Expression of the message was confirmed by RT-PCR. The Ad26 vectored vaccine was then injected into rhesus macaques ($10^{12}$ vector particles intramuscularly) to provoke robust, protective CD4$^+$ T-cell responses to the SARS-CoV-2 N protein. Of three animals injected, all developed the expected CD4$^+$ T-cell response two weeks following this single priming immunization (FIG. 13).

Figures 14, 15:
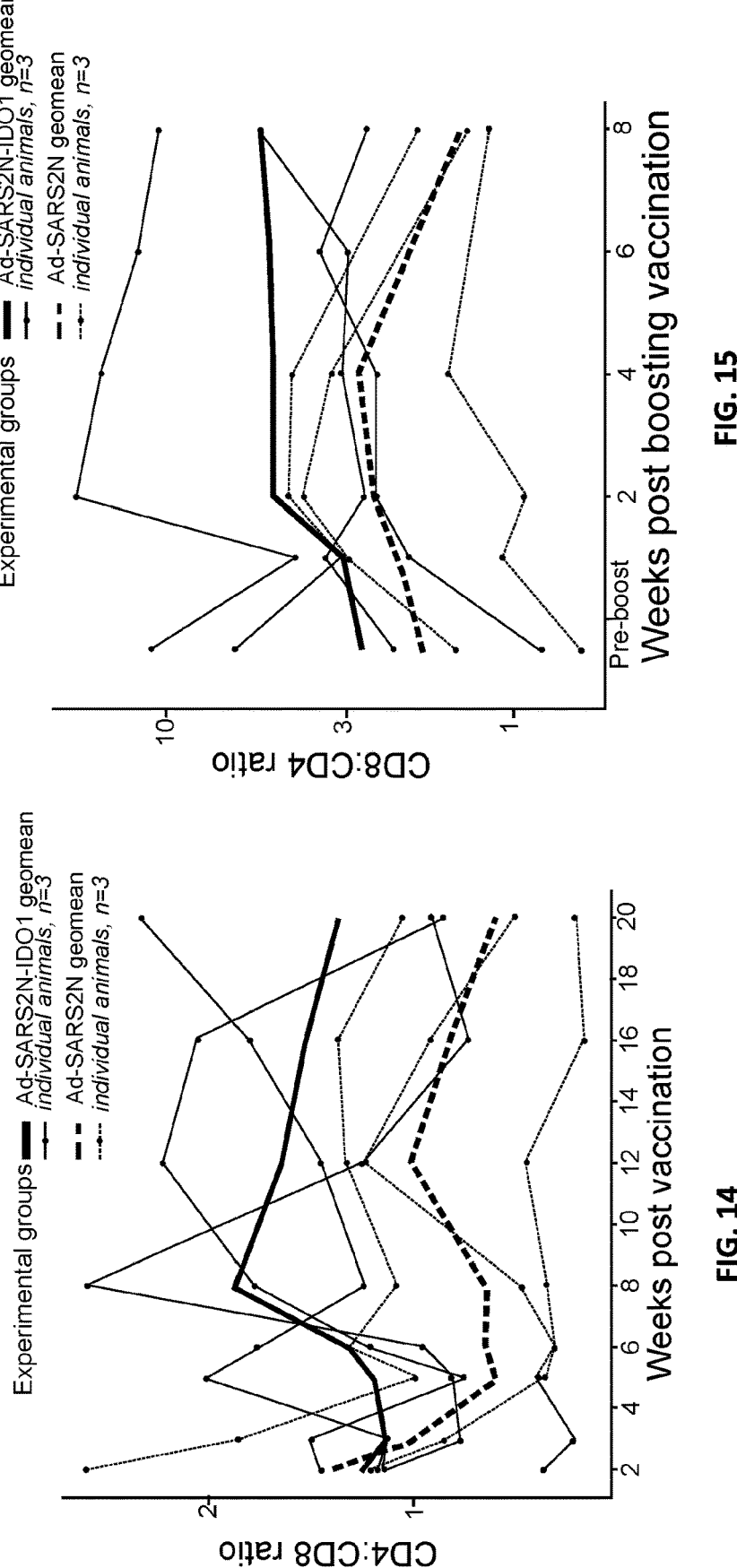
FIG. 14 is a graph showing an increased ratio of vaccine antigen-specific CD4$^+$ T cells to CD8$^+$ T cells among Ad-SARS2N-IRES-IDO1 recipients, where the measured responses include memory cells expressing IFNγ and/or TNFα. Fainter, thinner lines represent responses from individual vaccinated rhesus macaques; darker, thicker lines represent geometric mean responses. Conventional adenovirus-vectored vaccine (Ad-SARS2N, grey lines) produces more responses among CD8$^+$ than CD4$^+$ T cells, resulting in CD4:CD8 ratios that are usually below 1 (dashed gray line). IDO-expressing vaccines produce a response that is concentrated in the CD4 compartment, resulting in a CD4:CD8 ratio that is usually greater than 1 (Ad-SARS2N-IRES-IDO1, solid lines).
FIG. 15 is a graph showing the effect of boosting with IDO1-expressing vaccines vs. conventional vaccines in terms of the ratio of vaccine antigen-specific CD8$^+$ T cells to CD4$^+$ T cells, where the measured responses include memory cells expressing IFNγ. Conventional adenovirus-vectored vaccine (Ad35-SARS2N, grey lines) boosts the ratio only slightly before allowing it to fall by week 8. The Ad35-SARS2N-IRES-IDO1 produces a greater boost among CD8$^+$ than CD4$^+$ T cells, resulting in a higher CD8:CD4 ratio that is sustained for eight weeks after boosting.

A vaccine regimen lacking IDO1 expression ($10^{12}$ particles each of Ad26-SARS2N and Ad35-SARS2N at 0 and 4 weeks, respectively) was next compared to one that included IDO1 expression ($10^{12}$ particles each of Ad26-SARS2N-IDO1 and Ad35-SARS2N-IDO1 at 0 and 4 weeks, respectively). Rhesus macaques were vaccinated intramuscularly and their immune responses were monitored for 20 weeks after prime. As previously observed in the case of Ad-Gag-IRES-IDO1 (FIG. 9), the ratio of responding CD4:CD8$^+$ T cells was greater in recipients of the IDO1-expressing vaccines (FIG. 14). Furthermore, the observed ratio again exceeded 1, confirming CD4 predominance.

Example 3. Unique Features of a Boosting Vaccine Expressing IDO1

As shown in the previous Examples, when IDO1,-expressing vaccines are used alone, the T-cell response in vaccinated macaques is highly concentrated in CD4$^+$ T cells. In some circumstances, however, it is desirable to maintain and/or augment pre-existing T-cell responses by so-called "boosting" vaccination. For example, HIV vaccines that have an important CD8$^+$ T-cell component (e.g., inducing CD8$^+$ T-cell responses to the viral Gag protein) would be more efficacious over a longer period, if IDO1-expressing vaccines could boost and then maintain the functionally important CD8$^+$ T cells. IDO1-expressing vaccines can be superior boosters due to induction of supportive CD4$^+$ T-cell responses and/or to extension of transgene expression.

Figure 16:
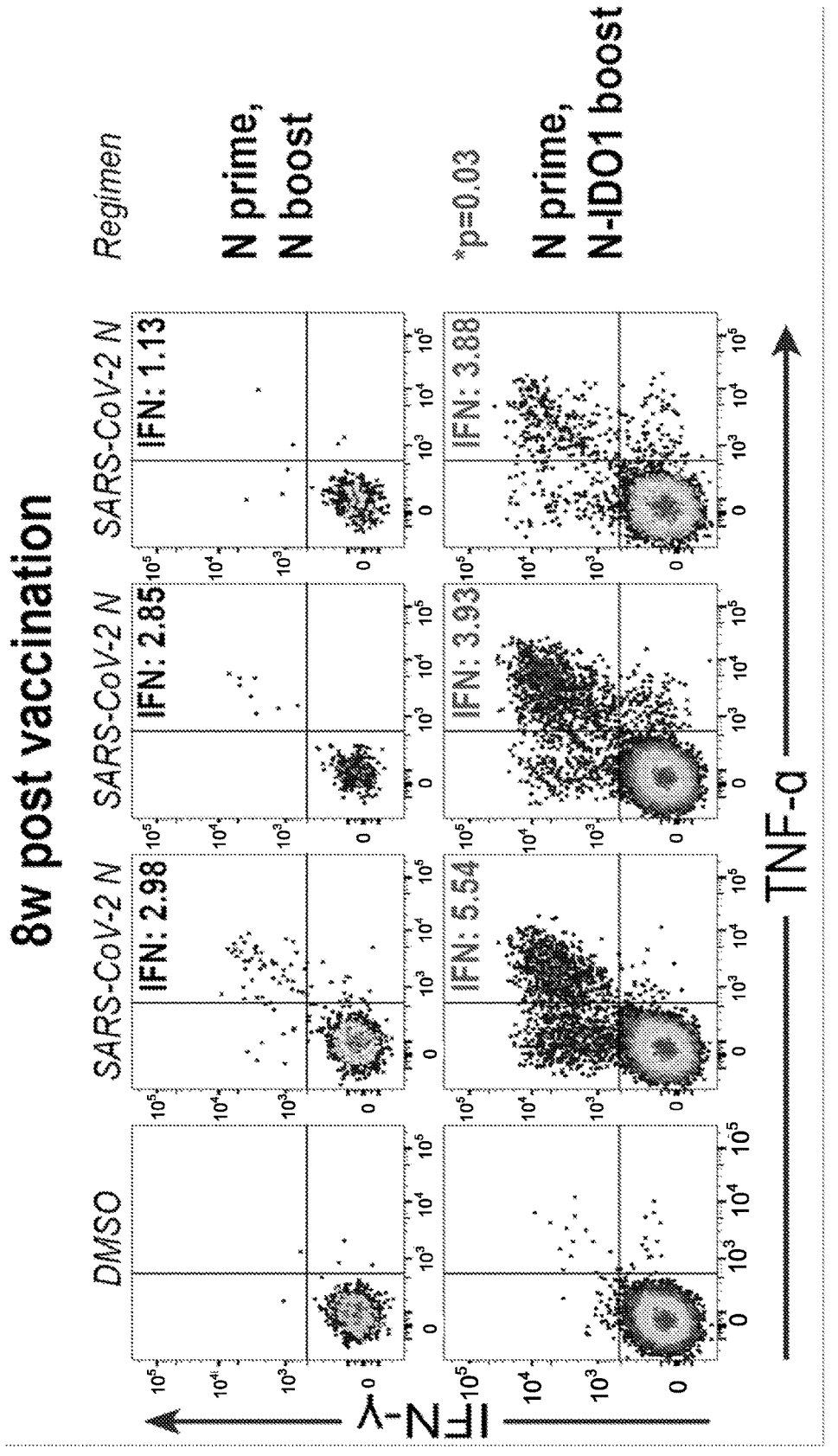
FIG. 16 shows that boosting vaccination with Ad35-SARS2N-IRES-IDO1 is superior to boosting with Ad35-SARS2N. Shown are CD8$^+$ T(EM) responses in broncho-alveolar lavage cells eight weeks after priming vaccination. Macaques receiving Ad35-SARS2N-IRES-IDO1 boosting have 2-3-fold more responsive CD8$^+$ cells (p=0.03 by one-sided Student's t test).

To demonstrate that IDO1-expressing vaccines can be superior boosters, six macaques were vaccinated intramuscularly with $10^{12}$ particles of Ad26-SARS2N. Four weeks later, three macaques were boosted with Ad35-SARS2N and three with Ad35-SARS2N-IRES-IDO1 at an identical dose of $10^{12}$ particles. Immune responses were followed by cytokine flow cytometry, using cells from peripheral blood or bronchoalveolar lavage. Isolated cells were stained with overlapping peptides from SARS-CoV-2 nucleocapsid in the presence of Brefeldin A to block cytokine export. Antibodies were then used to detect production of cytokines by T cells that are reactive to the vaccine immunogen. Two outcomes were noted indicative of the boosting power of IDO1-expressing vaccines when given to individuals with pre-existing T-cell responses. First, IDO1-expressing boosters led to greater expansion of vaccine-responsive CD8$^+$ T cells, as reflected in the CD8:CD4 ratio among responding cells in blood (FIG. 15). Second, this expansion of vaccine-responsive cells in blood was mirrored by similar expansion of CD8$^+$ T cells in lung (bronchoalveolar lavage fluid), which by eight weeks after boosting was higher in all recipients of boosting vaccines expressing IDO1 (FIG. 16; p=0.03 by one-sided Student's t test).

Example 4. Ad-SARS2S1-IRES-IDO1 Preparation and Vaccination

Under some circumstances it is desirable to elicit a robust CD4$^+$ T-cell response in order to augment a simultaneous antibody response. We therefore created adenoviral vectors that combine IDO1 expression with that of a secreted protein, i.e., the SARS-CoV-2 spike 51 domain (FIG. 11; SEQ ID NO:4). E1- and E3-deleted Ad26 and Ad35 backbones were engineered to contain a bicistronic expression cassette coding for the SARS-CoV-2 spike S1 domain and rhesus macaque IDO1 (SEQ ID NO:5). The S1 protein sequence is that from the original Wuhan isolate and is present in the expression cassette in codon-optimized form, carrying its endogenous signal sequence and terminated after 690 amino acids (SEQ ID NO:6). Expression of the message is confirmed by RT-PCR. These vectors are injected into rhesus macaques shortly in order to drive simultaneous antibody responses and CD4$^+$ T-cell responses against the SARS-CoV-2 spike S1 domain.

Example 5. Ad-Gag-IRES-Arginase Preparation and Vaccination

Figure 12:
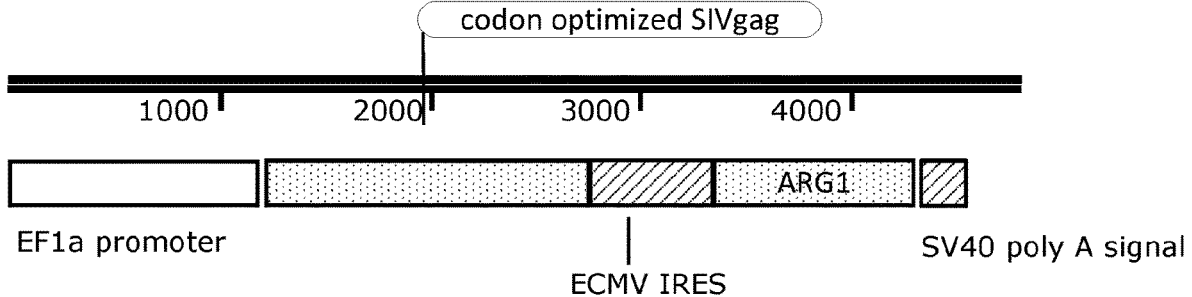
FIG. 12 illustrates a bicistronic expression cassette for driving production of both the SIV Gag gene and arginase in cells. Ad-SIVgagNF-IRES-ARG1 vaccine contains this cassette in "vectorized" Ad5 or Ad26. Expression of the bicistronic transcript is driven by a human EF1α promoter containing the first intron; the coding regions for SIV Gag and ARG1 are separated by an ECMV internal ribosomal entry site; and the cassette is terminated by an SV40 virus polyadenylation signal.

CD4$^+$ T-cell responses contribute to immune control over HIV. To create strong CD4$^+$ T-cell responses by vaccination, we engineer Ad5, Ad26, and Ad35 vaccines expressing SIV Gag sequences in combination with the macaque ARG1 coding sequences (FIG. 12). By mechanisms similar to those described for vaccines containing the tryptophan-degrading enzyme, IDO1, vectors expressing ARG1 drive robust CD4$^+$ T-cell responses that are protective against SIV in macaques and HIV in humans.

The terms "first" and "second" when used herein with reference to nucleic acid sequences or other elements or properties are simply to more clearly distinguish the two elements or properties and are not intended to indicate order.

Although the foregoing disclosure has been described in some detail by way of illustration and example for purpose of clarity of understanding, one of skill in the art will appreciate that certain changes and modifications within the spirit and scope of the disclosure may be practiced, e.g., within the scope of the appended claims. It should also be understood that aspects of the disclosure and portions of various recited embodiments and features can be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the disclosure. In addition, each reference provided herein is incorporated by reference in its entirety for all purposes to the same extent as if each reference was individually incorporated by reference.

INFORMAL SEQUENCE LISTING

| SEQ ID NO: | Sequence | Description |
|---|---|---|
| 1 | CGTGAGGCTCCGGTGCCCGTCAGTG GGCAGAGCGCACATCGCCCACAGTC CCCGAGAAGTTGGGGGGAGGGATCG GCAATTGAACCGGTGCCTAGAGAAG GTGGCGCGGGGTAAACTGGGAAAGT GATGTCGTGTACTGGCTCCGCCTTT TTCCCGAGGGTGGGGGAGAACCGTA TATAAGTGCAGTAGTCGCCGTGAAC GTTCTTTTTCGCAACGGGTTTGCCG CCAGAACACAGGTAGTGCCGTGTG TGGTTCCCGCGGGCCTGGCCTCTTT ACGGGTTATGGCCCTTGCGTGCCTT GAATTACTTCCACCTGGCTGCAGTA CGTGATTCTTGATCCCGAGCTTCGG GTTGGAAGTGGGTGGGAGAGTTCGA GGCCTTGCGCTTAAGGAGCCCCTTC GCCTCGTGCTTGAGTTGAGGCCTGG CCTGGGCGCTGGGGCCGCCGCGTGC GAATCTGGTGGCACCTTCGCGCCTG TCTCGCTGCTTTCGATAAGTCTCTA GCCATTTAAAATTTTTGATGACCTG CTGCGACGCTTTTTTTCTGGCAAGA TAGTCTTGTAAATGCGGGCCAAGAT CTGCACACTGGTATTTCGGTTTTTG GGGCCGCGGGCGGCGACGGGGCCCG TGCGTCCCAGCGCACATGTTCGGCG AGGCGGGGCCTGCGAGCGCGGCCAC CGAGAATCGGACGGGGGTAGTCTCA AGCTGGCCGGCCTGCTCTGGTGCCT GGCCTCGCGCCGCCGTGTATCGCCC CGCCCTGGGCGGCAAGGCTGGCCCG GTCGGCACCAGTTGCGTGAGCGGAA AGATGGCCGCTTCCCGGCCCTGCTG CAGGGAGCTCAAAATGGAGGACGCG GCGCTCGGGAGAGCGGGCGGGTGAG TCACCCACACAAAGGAAAAGGGCCT TTCCGTCCTCAGCCGTCGCTTCATG TGACTCCACGGAGTACCGGGCGCCG TCCAGGCACCTCGATTAGTTCTCGA GCTTTTGGAGTACGTCGTCTTTAGG TTGGGGGGAGGGGTTTTATGCGATG GAGTTTCCCCACACTGAGTGGGTGG AGACTGAAGTTAGGCCAGCTTGGCA CTTGATGTAATTCTCCTTGGAATTT GCCCTTTTTGAGTTTGGATCTTGGT TCATTCTCAAGCCTCAGACAGTGGT | Bicistronic cassette driving production of SIV Gag and *rhesus macaque* IDO1 |

-continued

| SEQ ID NO: | Sequence | Description |
|---|---|---|
| | TCAAAGTTTTTTTCTTCCATTTCAG GTGTCGTGAGGAATTAGCTGGCGCG CCTTCCCGCCACCATGGGCGTGAGA AACTCCGTCTTGTCAGGGAAGAAAG CAGATGAATTAGAAAAAATTAGGCT ACGACCCAACGGAAAGAAAAAGTAC ATGTTGAAGCATGTAGTATGGGCAG CAAATGAATTAGATAGATTTGGATT AGCAGAAAGCCTGTTGGAGAACAAA GAAGGATGTCAAAAAATACTTTCGG TCTTAGCTCCATTAGTGCCAACAGG CTCAGAAAATTTAAAAAGCCTTTAT AATACTGTCTGCGTCATCTGGTGCA TTCACGCAGAAGAGAAAGTGAAACA CACTGAGGAAGCAAAACAGATAGTG CAGAGACACCTAGTGGTGGAAACAG GAACCACCGAAACCATGCCGAAGAC CTCTCGACCAACAGCACCATCTAGC GGCAGAGGAGGAAACTACCCAGTAC AGCAGATCGGTGGCAACTACGTCCA CCTGCCACTGTCCCCGAGAACCCTG AACGCTTGGGTCAAGCTGATCGAGG AGAAGAAGTTCGGAGCAGAAGTAGT GCCAGGATTCCAGGCACTGTCAGAA GGTTGCACCCCCTACGACATCAACC AGATGCTGAACTGCGTTGGAGACCA TCAGGCGGCTATGCAGATCATCCGT GACATCATCAACGAGGAGGCTGCAG ATTGGGACTTGCAGCACCCACAACC AGCTCCACAACAAGGACAACTTAGG GAGCCGTCAGGATCAGACATCGCAG GAACCACCTCCTCAGTTGACGAACA GATCCAGTGGATGTACCGTCAGCAG AACCCGATCCCAGTAGGCAACATCT ACCGTCGATGGATCCAGCTGGGTCT GCAGAAATGCGTCCGTATGTACAAC CCGACCAACATTCTAGATGTAAAAC AAGGGCCAAAAGAGCCATTTCAGAG CTATGTAGACAGGTTCTACAAAAGT TTAAGAGCAGAACAGACAGATGCAG CAGTAAAGAATTGGATGACTCAAAC ACTGCTGATTCAAAATGCTAACCCA GATTGCAAGCTAGTGCTGAAGGGGC TGGGTGTGAATCCCACCCTAGAAGA AATGCTGACGGCTTGTCAAGGAGTA GGGGGGCCGGGACAGAAGGCTAGAT TAATGGCAGAAGCCCTGAAAGAGGC CCTCGCACCAGTGCCAATCCCTTTT GCAGCAGCCCAACAGAGGGGACCAA GAAAGCCAATTAAGTGTTGGAATTG TGGGAAAGAGGGACACTCTGCAAGG CAATGCAGAGCCCCAAGAAGACAGG GATGCTGGAAATGTGGAAAAATGGA CCATGTTATGGCCAAATGCCCAGAC AGACAGGCGGGTTTTTTAGGCCTTG GTCCATGGGGAAAGAAGCCCCGCAA TTTCCCCATGGCTCAAGTGCATCAG GGGCTGATGCCAACTGCTCCCCCAG AGGACCCAGCTGTGGATCTGCTAAA GAACTACATGCAGTTGGGCAAGCAG CAGAGAGAAAAGCAGAGAGAAAGCA GAGAGAAGCCTTACAAGGAGGTGAC AGAGGATTTGCTGCACCTCAATTCT CTCTTTGGAGGAGACCAGTAGTAGC CTGCAGGCCCCTCTCCCTCCCCCCC CCCTAACGTTACTGGCCGAAGCCGC TTGGAATAAGGCCGGTGTGCGTTTG TCTATATGTTATTTTCCACCATATT GCCGTCTTTTGGCAATGTGAGGGCC CGGAAACCTGGCCCTGTCTTCTTGA CGAGCATTCCTAGGGGTCTTTCCCC TCTCGCCAAAGGAATGCAAGGTCTG TTGAATGTCGTGAAGGAAGCAGTTC CTCTGGAAGCTTCTTGAAGACAAAC AACGTCTGTAGCGACCCTTTGCAGG | |

-continued

| SEQ ID NO: | Sequence | Description |
|---|---|---|
| | CAGCGGAACCCCCCACCTGGCGACA | |
| | GGTGCCTCTGCGGCCAAAAGCCACG | |
| | TGTATAAGATACACCTGCAAAGGCG | |
| | GCACAACCCCAGTGCCACGTTGTGA | |
| | GTTGGATAGTTGTGGAAAGAGTCAA | |
| | ATGGCTCTCCTCAAGCGTATTCAAC | |
| | AAGGGGCTGAAGGATGCCCAGAAGG | |
| | TACCCCATTGTATGGGATCTGATCT | |
| | GGGGCCTCGGTGCACATGCTTTACA | |
| | TGTGTTTAGTCGAGGTTAAAAAAAC | |
| | GTCTAGGCCCCCGAACCACGGGGA | |
| | CGTGGTTTTCCTTTGAAAAACACGA | |
| | TGATAAAGCCACCATGGCACATGCT | |
| | ATGGAAAACTCCTGGACAATCAGTG | |
| | AAGAGTACCATATTGATGAAGAAGT | |
| | GGGCTTCGCTCTGCCAAATCCACAG | |
| | GAAAATCTACCTGATTTTTATAATG | |
| | ACTGGATGTTCATTGCCAAACATCT | |
| | GCCTGATCTCATAGAGTCTGGCCAA | |
| | CTTCGAGAAAGAGTTGAGAAGTTAG | |
| | ACATGCTCAGCATTGATCATCTCAC | |
| | AGACCACAAGTCACGCGCCTTGCA | |
| | CATCTAGTTCTGGGATGCATCACCA | |
| | TGGCATATGTGTGGGATAAAGGTCA | |
| | TGGAGACGTCCGTAAGGTCTTGCCA | |
| | AGAAATATTGCTGTTCTTACTGCC | |
| | AACTCTCCAAGAAACTGGGCCTGCC | |
| | TCCTATTCTGGTTTATGCAGACTGT | |
| | GTCTTGGCAAACTGGAAGAAAAAGG | |
| | ATCCTAATAAGCCCCTGACTTATGA | |
| | GAACATGGACGTTTTGTTCTCCTTT | |
| | CGTGATGGAGACTGCAGTAAAGGAT | |
| | TCTTCCTGGTTTCTCTATTGGTGGA | |
| | AATAGCAGCTGCTTCTGCTATCAAA | |
| | GAAATTCCTACTGTATTCAGGGCAA | |
| | TGCAATTGCGAGAACGGGACACTCT | |
| | GCTAAAGGCACTGTTGGAAATAGCT | |
| | TCTTGCCTGGAGAAAGCCCGTCAAG | |
| | TGTTTCAGCAAATGCACGATCACGT | |
| | AAACCCAAATGCATTTTACAGTGTT | |
| | CTTCGCATATATTTGGCTGGCTGGA | |
| | AAGGCAACCCCCAGCTATCAGACGG | |
| | TCTGGTGTATGAGGGGTTCTGGGAA | |
| | GGCCCAAAGAAGTTTGCAGGGGGCA | |
| | GTGCAGCACAAAGCAGCATCTTTCA | |
| | GTGCTTTGACGTCCTGCTGGGCATC | |
| | CAACAGAATGCTGGTGGAGGACATG | |
| | CTGCTCAGTTCCTCCAGGACATGAG | |
| | AACATATATGCCACCAGCTCACAGG | |
| | AACTTCCTGTACTCATTAGAGTCAA | |
| | GTCCCTCAGTCCGTGAGTTTGTCCT | |
| | TTCAAAAGGTGATGCTGGCCTGCGG | |
| | GAAGCTTATGATGCCTGTGTGAAAG | |
| | CTCTGGTCTCCCTGAGGAGCTACCA | |
| | TCTGCAAATCGTGACTAAGTACGTC | |
| | CTGATTCCTGCAAGCCAGCAGCCAA | |
| | AGGAAACAAGACCTCTGAAGACCC | |
| | TTCAAAACTGGATGCCAAAGGAACT | |
| | GGAGGCACTGATTTAATGGAATTCC | |
| | TAAAGACTGTGAGAAGTACAACCGA | |
| | GAAATACCGTTTGAAGGAAGGTTAA | |
| | GACCTGCAGGACGCCACAGCTCTGA | |
| | TCATAATCAGCCATACCACATTTGT | |
| | AGAGGTTTTACTTGCTTTAAAAAAC | |
| | CTCCCACACCTCCCCCTGAACCTGA | |
| | AACATAAAATGAATGCAATTGTTGT | |
| | TGTTAACTTGTTTATTGCAGCTTAT | |
| | AATGGTTACAAATAAAGCAATAGCA | |
| | TCACAAATTTCACAAATAAAGCATT | |
| | TTTTTCACTGCATTCTAGTTGTGGT | |
| | TTGTCCAAACTCATCAATGTATCTG | |
| | C | |
| 2 | MSDNGPQNQRNAPRITFGGPSDSTG | SARS-CoV-2 |
| | SNQNGERSGARSKQRRPQGLPNNTA | nucleoprotein |

-continued

| SEQ ID NO: | Sequence | Description |
|---|---|---|
| | SWFTALTQHGKEDLKFPRGQGVPIN | sequence |
| | TNSSPDDQIGYYRRATRRIRGGDGK | |
| | MKDLSPRWYFYYLGTGPEAGLPYGA | |
| | NKDGIIWVATEGALNTPKDHIGTRN | |
| | PANNAAIVLQLPQGTTLPKGFYAEG | |
| | SRGGSQASSRSSSRSRNSSRNSTPG | |
| | SSRGTSPARMAGNGGDAALALLLLD | |
| | RLNQLESKMSGKGQQQQGQTVTKKS | |
| | AAEASKKPRQKRTATKAYNVTQAFG | |
| | RRGPEQTQGNFGDQELIRQGTDYKH | |
| | WPQIAQFAPSASAFFGMSRIGMEVT | |
| | PSGTWLTYTGAIKLDDKDPNFKDQV | |
| | ILLNKHIDAYKTFPPTEPKKDKKKK | |
| | ADETQALPQRQKKQQTVTLLPAADL | |
| | DDFSKQLQQSMSSADSTQA | |
| 3 | CGTGAGGCTCCGGTGCCCGTCAGTG | Bicistronic |
| | GGCAGAGCGCACATCGCCCACAGTC | cassette driving |
| | CCCGAGAAGTTGGGGGGGAGGGGTCG | production of |
| | GCAATTGAACCGGTGCCTAGAGAAG | SARS-CoV-2 |
| | GTGGCGCGGGGTAAACTGGGAAAGT | nucleoprotein and |
| | GATGTCGTGTACTGGCTCCGCCTTT | *rhesus macaque* |
| | TTCCCGAGGGTGGGGGAGAACCGTA | IDO1 |
| | TATAAGTGCAGTAGTCGCCGTGAAC | |
| | GTTCTTTTTCGCAACGGGTTTGCCG | |
| | CCAGAACACAGGTAAGTGCCGTGTG | |
| | TGGTTCCCGCGGGCCTGGCCTCTTT | |
| | ACGGGTTATGGCCCTTGCGTGCCTT | |
| | GAATTACTTCCACCTGGCTGCAGTA | |
| | CGTGATTCTTGATCCCGAGCTTCGG | |
| | GTTGGAAGTGGGTGGGAGAGTTCGA | |
| | GGCCTTGCGCTTAAGGAGCCCCTTC | |
| | GCCTCGTGCTTGAGTTGAGGCCTGG | |
| | CCTGGGCGCTGGGGCCGCCGCGTGC | |
| | GAATCTGGTGGCACCTTCGCGCCTG | |
| | TCTCGCTGCTTTCGATAAGTCTCTA | |
| | GCCATTTAAAATTTTTGATGACCTG | |
| | CTGCGACGCTTTTTTTCTGGCAAGA | |
| | TAGTCTTGTAAATGCGGGCCAAGAT | |
| | CTGCACACTGGTATTTCGGTTTTTG | |
| | GGGCCGCGGGCGGCGACGGGGCCCG | |
| | TGCGTCCCAGCGCACATGTTCGGCG | |
| | AGGCGGGGCCTGCGAGCGCGGCCAC | |
| | CGAGAATCGGACGGGGGTAGTCTCA | |
| | AGCTGGCCGGCCTGCTCTGGTGCCT | |
| | GGCCTCGCGCCGCCGTGTATCGCCC | |
| | CGCCCTGGGCGGCAAGGCTGGCCCG | |
| | GTCGGCACCAGTTGCGTGAGCGGAA | |
| | AGATGGCCGCTTCCCGGCCCTGCTG | |
| | CAGGGAGCTCAAAATGGAGGACGCG | |
| | GCGCTCGGGAGAGCGGGCGGGTGAG | |
| | TCACCCACACAAAGGAAAAGGGCCT | |
| | TTCCGTCCTCAGCCGTCGCTTCATG | |
| | TGACTCCACGGAGTACCGGGCGCCG | |
| | TCCAGGCACCTCGATTAGTTCTCGA | |
| | GCTTTTGGAGTACGTCGTCTTTAGG | |
| | TTGGGGGGAGGGGTTTTATGCGATG | |
| | GAGTTTCCCCACACTGAGTGGGTGG | |
| | AGACTGAAGTTAGGCCAGCTTGGCA | |
| | CTTGATGTAATTCTCCTTGGAATTT | |
| | GCCCTTTTTGAGTTTGGATCTTGGT | |
| | TCATTCTCAAGCCTCAGACAGTGGT | |
| | TCAAAGTTTTTTTCTTCCATTTCAG | |
| | GTGTCGTGAGGAATTAGCTGGCGCG | |
| | CCTTCCCGCCACCATGAGCGATAAC | |
| | GGCCCCCAGAATCAGAGGAATGCAC | |
| | CTAGGATAACATTTGGAGGTCCGTC | |
| | AGACAGCACTGGCTCCAACCAGAAT | |
| | GGCGAGCGGTCTGGCGCGCGGTCTA | |
| | AGCAAAGGAGACCACAAGGTCTCCC | |
| | GAATAACACGGCCTCCTGGTTTACA | |
| | GCGCTCACCCAGCACGGTAAAGAGG | |
| | ACCTGAAGTTCCCTAGGGGGCAAGG | |
| | TGTACCGATTAATACCAACAGCTCC | |
| | CCCGATGACCAGATTGGTTATTATA | |

| | |
|---|---|
| 37 | 38 |
| -continued | -continued |

| SEQ ID NO: | Sequence | Description |
|---|---|---|
| | GAAGAGCTACAAGACGCATACGGGG | |
| | TGGAGATGGGAAGATGAAGGACCTC | |
| | TCCCCTCGGTGGTATTTTTATTATC | |
| | TGGGCACCGGACCGGAAGCCGGGCT | |
| | CCCCTACGGCGCCAATAAGGACGGT | |
| | ATAATATGGGTCGCCACTGAGGGTG | |
| | CCCTCAATACCCCGAAGGACCACAT | |
| | TGGCACTCGAAACCCGGCAAACAAC | |
| | GCAGCTATTGTCCTGCAACTCCCAC | |
| | AGGGTACCACGCTCCCGAAAGGTTT | |
| | TTATGCCGAAGGGTCTCGCGGGGGT | |
| | TCACAGGCTAGCAGTCGAAGCTCAT | |
| | CTCGGAGCCGAAATAGCTCAAGGAA | |
| | TTCAACACCCGGAAGCTCCAGAGGC | |
| | ACAAGCCCTGCGCGGATGGCAGGGA | |
| | ACGGAGGCGATGCTGCCCTGGCCCT | |
| | CCTTCTCTTGGATAGACTTAATCAG | |
| | CTGGAATCCAAAATGTCAGGAAAGG | |
| | GCCAGCAACAACAAGGTCAGACAGT | |
| | GACCAAAAAATCCGCCGCAGAGGCC | |
| | AGTAAGAAACCTAGACAGAAGCGAA | |
| | CTGCTACAAAGGCTATAATGTAAC | |
| | TCAGGCGTTCGGACGGCGAGGCCCT | |
| | GAACAAACCCAGGGCAATTTCGGTG | |
| | ACCAAGAACTCATAAGACAGGGAAC | |
| | TGACTACAAACATTGGCCCCAGATT | |
| | GCACAATTTGCCCCATCCGCCTCAG | |
| | CCTTCTTCGGAATGTCTCGCATCGG | |
| | GATGGAGGTAACACCGAGCGGGACC | |
| | TGGCTCACATACACAGGTGCGATAA | |
| | AGCTCGATGACAAAGATCCCAATTT | |
| | TAAAGACCAAGTGATACTTCTTAAT | |
| | AAGCACATAGACGCCTATAAAACCT | |
| | TCCCGCCCACTGAGCCAAAGAAAGA | |
| | CAAGAAAAAAAAGCGGACGAGACA | |
| | CAAGCCCTTCCGCAAAGACAGAAAA | |
| | AACAGCAAACGGTTACATTGCTTCC | |
| | TGCGGCAGACCTGGATGATTTTTCC | |
| | AAACAGCTTCAGCAATCTATGTCTA | |
| | GCGCAGATAGTACCCAGGCGTAATA | |
| | GCCTGCAGGCCCCTCTCCCTCCCCC | |
| | CCCCCTAACGTTACTGGCCGAAGCC | |
| | GCTTGGAATAAGGCCGGTGTGCGTT | |
| | TGTCTATATGTTATTTTCCACCATA | |
| | TTGCCGTCTTTTGGCAATGTGAGGG | |
| | CCCCGGAAACCTGGCCCTGTCTTCTT | |
| | GACGAGCATTCCTAGGGGTCTTTCC | |
| | CCTCTCGCCAAAGGAATGCAAGGTC | |
| | TGTTGAATGTCGTGAAGGAAGCAGT | |
| | TCCTCTGGAAGCTTCTTGAAGACAA | |
| | ACAACGTCTGTAGCGACCCTTTGCA | |
| | GGCAGCGGAACCCCCCACCTGGCGA | |
| | CAGGTGCCTCTGCGGCCAAAAGCCA | |
| | CGTGTATAAGATACACCTGCAAAGG | |
| | CGGCACAACCCCAGTGCCCACGTTGT | |
| | GAGTTGGATAGTGTGTGGAAAGAGTC | |
| | AAATGGCTCTCCTCAAGCGTATTCA | |
| | ACAAGGGGCTGAAGGATGCCCAGAA | |
| | GGTACCCCATTGTATGGGATCTGAT | |
| | CTGGGGCCTCGGTGCACATGCTTTA | |
| | CATGTGTTTAGTCGAGGTTAAAAAA | |
| | ACGTCTAGGCCCCCCGAACCACGGG | |
| | GACGTGGTTTTCCTTTGAAAAACAC | |
| | GATGATAAAGCCACCATGGCACATG | |
| | CTATGGAAAACTCCTGGACAATCAG | |
| | TGAAGAGTACCATATTGATGAAGAA | |
| | GTGGGCTTCGCTCTGCCAAATCCAC | |
| | AGGAAAATCTACCTGATTTTTATAA | |
| | TGACTGGATGTTCATTGCCAAACAT | |
| | CTGCCTGATCTCATAGAGTCTGGCC | |
| | AACTTCGAGAAAGAGTTGAGAAGTT | |
| | AGACATGCTCAGCATTGATCATCTC | |
| | ACAGACCACAAGTCACAGCGCCTTG | |
| | CACATCTAGTTCTGGGATGCATCAC | |
| | CATGGCATATGTGTGGGATAAAGGT | |

| SEQ ID NO: | Sequence | Description |
|---|---|---|
| | CATGGAGACGTCCGTAAGGTCTTGC | |
| | CAAGAAATATTGCTGTTCCTTACTG | |
| | CCAACTCTCCAAGAAACTGGGCCTG | |
| | CCTCCTATTCTGGTTTATGCAGACT | |
| | GTGTCTTGGCAAACTGGAAGAAAAA | |
| | GGATCCTAATAAGCCCCTGACTTAT | |
| | GAGAACATGGACGTTTTGTTCTCCT | |
| | TTCGTGATGGAGACTGCAGTAAAGG | |
| | ATTCTTCCTGGTTTCTCTATTGGTG | |
| | GAAATAGCAGCTGCTTCTGCTATCA | |
| | AAGAAATTCCTACTGTATTCAGGGC | |
| | AATGCAATTGCGAGAACGGGACACT | |
| | CTGCTAAAGGCACTGTTGGAAATAG | |
| | CTTCTTGCCTGGAGAAAGCCCGTCA | |
| | AGTGTTTCAGCAAATGCACGATCAC | |
| | GTAAACCCAAATGCATTTTACAGTG | |
| | TTCTTCGCATATATTTGGCTGGCTG | |
| | GAAAGGCAACCCCCAGCTATCAGAC | |
| | GGTCTGGTGTATGAGGGGTTCTGGG | |
| | AAGGCCCAAAGAAGTTTGCAGGGGG | |
| | CAGTGCAGCACAAAGCAGCATCTTT | |
| | CAGTGCTTTGACGTCCTGCTGGGCA | |
| | TCCAACAGAATGCTGGTGGAGGACA | |
| | TGCTGCTCAGTTCCTCCAGGACATG | |
| | AGAACATATATGCCACCAGCTCACA | |
| | GGAACTTCCTGTACTCATTAGAGTC | |
| | AAGTCCCTCAGTCCGTGAGTTTGTC | |
| | CTTTCAAAAGGTGATGCTGGCCTGC | |
| | GGGAAGCTTATGATGCCTGTGTGAA | |
| | AGCTCTGGTCTCCCTGAGGAGCTAC | |
| | CATCTGCAAATCGTGACTAAGTACG | |
| | TCCTGATTCCTGCAAGCCAGCAGCC | |
| | AAAGGAAAACAAGACCTCTGAAGAC | |
| | CCTTCAAAACTGGATGCCAAAGGAA | |
| | CTGGAGGCACTGATTTAATGGAATT | |
| | CCTAAAGACTGTGAGAAGTACAACC | |
| | GAGAAATACCGTTTGAAGGAAGGTT | |
| | AAGACCTGCAGGACGCCACACGCTCT | |
| | GATCATAATCAGCCATACCACACATTT | |
| | GTAGAGGTTTTACTTGCTTTAAAAA | |
| | ACCTCCCACACCTCCCCCTGAACCT | |
| | GAAACATAAAATGAATGCAATTGTT | |
| | GTTGTTAACTTGTTTATTGCAGCTT | |
| | ATAATGGTTACAAATAAAGCAATAG | |
| | CATCACAAATTTCACAAATAAAGCA | |
| | TTTTTTTTCACTGCATTCTAGTTGTG | |
| | GTTTGTCCAAACTCATCAATGTATC | |
| | T | |
| 4 | MFVFLVLLPLVSSQCVNLTTRTQLP PAYTNSFTRGVYYPDKVFRSSVLHS TQDLFLPFFSNVTWFHAIHVSGTNG TKRFDNPVLPFNDGVYFASTEKSNI IRGWIFGTTLDSKTQSLLIVNNATN VVIKVCEFQFCNDPFLGVYYHKNNK SWMESEFRVYSSANNCTFEYVSQPF LMDLEGKQGNFKNLREFVFKNIDGY FKIYSKHTPINLVRDLPQGFSALEP LVDLPIGINITRFQTLLALHRSYLT PGDSSSGWTAGAAAYYVGYLQPRTF LLKYNENGTITDAVDCALDPLSETK CTLKSFTVEKGIYQTSNFRVQPTES IVRFPNITNLCPFGEVFNATRFASV YAWNRKRISNCVADYSVLYNSASFS TFKCYGVSPTKLNDLCFTNVYADSF VIRGDEVRQIAPGQTGKIADYNYKL PDDFTGCVIAWNSNNLDSKVGGNYN YLYRLFRKSNLKPFERDISTEIYQA GSTPCNGVEGFNCYFPLQSYGFQPT NGVGYQPYRVVVLSFELLHAPATVC GPKKSTNLVKNKCVNFNFNGLTGTG VLTESNKKFLPFQQFGRDIADTTDA VRDPQTLEILDITPCSFGGVSVITP GTNTSNQVAVLYQDVNCTEVPVAIH ADQLTPTWRVYSTGSNVFQTRAGCL | SARS-CoV-2 spike S1 domain protein sequence |

| SEQ ID NO: | Sequence | Description |
|---|---|---|
| | IGAEHVNNSYECDIPIGAGICASYQ TQTNSPRRARSVASQ* | |
| 5 | CGTGAGGCTCCGGTGCCCGTCAGTG GGCAGAGCGCACATCGCCCACAGTC CCCGAGAAGTTGGGGGGAGGGGTCG GCAATTGAACCGGTGCCTAGAGAAG GTGGCGCGGGGTAAACTGGGAAAGT GATGTCGTGTACTGGCTCCGCCTTT TTCCCGAGGGTGGGGGAGAACCGTA TATAAGTGCAGTAGTCGCCGTGAAC GTTCTTTTTCGCAACGGGTTTGCCG CCAGAACACAGGTAAGTGCCGTGTG TGGTTCCCGCGGGCCTGGCCTCTTT ACGGGTTATGGCCCTTGCGTGCCTT GAATTACTTCCACCTGGCTGCAGTA CGTGATTCTTGATCCCGAGCTTCGG GTTGGAAGTGGGTGGGAGAGTTCGA GGCCTTGCGCTTAAGGAGCCCCTTC GCCTCGTGCTTGAGTTGAGGCCTGG CCTGGGCGCTGGGGCCGCCGCGTGC GAATCTGGTGGCACCTTCGCGCCTG TCTCGCTGCTTTCGATAAGTCTCTA GCCATTTAAAATTTTTGATGACCTG CTGCGACGCTTTTTTTCTGGCAAGA TAGTCTTGTAAATGCAGGCCAAGAT CTGCACACTGGTATTTCGGTTTTTG GGGCCGCGGGCGGCGACGGGGCCCG TGCGTCCCAGCGCACATGTTCGGCG AGGCGGGGCCTGCGAGCGCGGCCAC CGAGAATCGGACGGGGGGTAGTCTCA AGCTGGCCGGCCTGCTCTGGTGCCT GGCCTCGCGCCGCCGTGTATCGCCC CGCCCTGGGCGGCAAGGCTGGCCCG GTCGGCACCAGTTGCGTGAGCGGAA AGATGGCCGCTTCCCGGCCCTGCTG CAGGGAGCTCAAAATGGAGGACGCG GCGCTCGGGAGAGCGGGCGGGTGAG TCACCCACACAAAGGAAAAGGGCCT TTCCGTCCTCAGCCGTCGCTTCATG TGACTCCACGGAGTACCGGGCGCCG TCCAGGCACCTCGATTAGTTCTCGA GCTTTTGGAGTACGTCGTCTTTAGG TTGGGGGGAGGGGTTTTATGCGATG GAGTTTCCCCACACTGAGTGGGTGG AGACTGAAGTTAGGCCAGCTTGGCA CTTGATGTAATTCTCCTTGGAATTT GCCCTTTTTGAGTTTGGATCTTGGT TCATTCTCAAGCCTCAGACAGTGGT TCAAAGTTTTTTTCTTCCATTTCAG GTGTCGTGAGGAATTAGCTGGCGCG CCTTCCCGCCACCATGTTTGTGTTT CTGGTATTGCTGCCATTGGTCTCCA GCCAATGTGTTAATCTCACGACCAG GACCCAATTGCCTCCCGCGTATACT AACTCTTTCACGAGGGGAGTCTACT ATCCTGACAAAGTATTTAGGTCTTC AGTGCTGCATAGTACACAAGACCTG TTCCTTCCGTTTTCAGCAACGTGA CTTGGTTCCACGCTATACACGTCTC AGGGACGAATGGAACAAAGCGCTTC GATAATCCGGTTTTGCCATTTAATG ATGGTGTCTATTTCGCATCCACAGA AAAGTCCAACATTATCAGGGGGTGG ATCTTTGGTACGACGCTGGATAGCA AAACACAGTCCCTCCTTATCGTCAA CAATGCCACGAATGTGGTGATTAAG GTTTGCGAATTTCAATTTTGTAACG ACCCTTTTCTTGGCGTATATTATCA TAAAAACAACAAGTCCTGGATGGAA AGCGAATTCCGCGTATACAGTTCCG CAAACAACTGTACATTTGAATATGT GAGCCAACCTTTTCTGATGGACCTG GAGGGCAAACAGGGCAACTTTAAAA ATTTGAGAGAGTTCGTCTTCAAAAA | Bicistronic cassette driving production of SARS-CoV-2 spike S1 domain and *rhesus macaque* IDO1 |

| SEQ ID NO: | Sequence | Description |
|---|---|---|
| | TATTGATGGATATTTCAAGATTTAT AGTAAGCATACGCCCATAAATCTTG TCCGGGATCTGCCGCAGGGTTTTAG CGCTCTCGAACCCTTGGTAGACCTC CCGATTGGTATAAACATCACCAGGT TTCAGACCCTTCTTGCGTTGCACCG CAGCTATCTCACGCCAGGCGATAGT AGTTCAGGTTGGACTGCCGGAGCAG CAGCCTACTACGTAGGCTACCTTCA ACCTAGAACGTTTCTGTTGAAATAT AATGAAAATGGTACAATCACAGACG CGGTCGACTGCGCACTGGACCCGCT GAGCGAAACCAAATGTACGCTCAAG TCCTTCACCGTAGAGAAAGGCATCT ACCAGACTTCTAATTTCCGAGTGCA GCCGACGGAGTCAATCGTGAGATTC CCTAACATAACTAATTTGTGTCCAT TTGGCGAAGTGTTCAATGCAACCAG ATTCGCCTCCGTCTATGCGTGGAAT CGAAAAAGAATTTCAAACTGCGTAG CGGATTATTCTGTCTTGTACAATAG TGCCTCCTTTAGTACGTTCAAGTGT TATGGGGTGTCACCAACGAAGTTGA ATGATCTTTGTTTCACGAATGTTTA CGCTGATTCATTTGTAATACGCGGA GACGAAGTTAGACAAATCGCACCAG GGCAGACAGGCAAGATCGCGGATTA TAATTATAAGCTGCCAGACGACTTC ACTGGGTGCGTTATCGCATGGAACT CCAACAACTTGGATAGTAAAGTGGG CGGGAATTACAACTACCTGTATAGA CTTTTCCGAAAGTCCAATTTGAAGC CATTCGAAAGGGACATTTCTACTGA AATATATCAAGCGGGATCAACACCT TGCAACGGAGTGGAAGGGTTCAACT GCTACTTTCCGCTGCAATCTTATGG GTTTCAACCGACTAATGGAGTCGGG TATCAGCCTTACAGAGTTGTTGTTC TTTCCTTTGAGCTGTTGCATGCCCC GGCAACCGTATGTGGGCCCAAGAAA TCTACAAACCTCGTTAAGAATAAAT GCGTGAATTTCAACTTCAATGGTCT CACCGGGACGGGGGTCCTGACCGAA AGTAACAAGAAATTTCTGCCCCTTTC AGCAATTCGGAAGAGACATCGCGGA CACTACAGACGCCGTTCGGGACCCG CAGACTCTCGAAATTCTTGACATCA CGCCGTGTTCATTCGGAGGCGTTTC CGTGATTACACCAGGAACGAATACC AGCAATCAAGTGGCAGTGTTGTATC AAGATGTTAATTGCACTGAAGTGCC TGTCGCTATCCACGCGGACCAGCTC ACGCCTACGTGGAGGGTGTATTCAA CAGGAAGCAACGTGTTCCAAACACG AGCGGGTTGTCTTATAGGGGCGGAG CACGTGAACAATAGTTACGAATGTG ATATACCGATAGGGGCTGGGATATG TGCGTCTTATCAAACACAGACGAAT AGCCCCAGGCGCGCTCGAAGTGTGG CAAGCCAATAGTAGCCTGCAGGCCC CTCTCCCTCCCCCCCCCCTAACGTT ACTGGCCGAAGCCGCTTGGAATAAG GCCGGTGTGCGTTTGTCTATATGTT ATTTTCCACCATATTGCCGTCTTTT GGCAATGTGAGGGCCCGGAAACCTG GCCCTGTCTTCTTGACGAGCATTCC TAGGGGTCTTTCCCCTCTCGCCAAA GGAATGCAAGGTCTGTTGAATGTCG TGAAGGAAGCAGTTCCTCTGGAAGC TTCTTGAAGACAAACAACGTCTGTA GCGACCCTTTGCAGGCAGCGGAACC CCCCACCTGGCGACAGGTGCCTCTG CGGCCAAAAGCCACGTGTATAAGAT ACACCTGCAAAGGCGGCACAACCCC AGTGCCACGTTGTGAGTTGGATAGT | |

-continued

| SEQ ID NO: | Sequence | Description |
|---|---|---|
| | TGTGGAAAGAGTCAAATGGCTCTCC | |
| | TCAAGCGTATTCAACAAGGGGCTGA | |
| | AGGATGCCCAGAAGGTACCCCATTG | |
| | TATGGGATCTGATCTGGGGCCTCGG | |
| | TGCACATGCTTTACATGTGTTTAGT | |
| | CGAGGTTAAAAAAACGTCTAGGCCC | |
| | CCCGAACCACGGGGACGTGGTTTTC | |
| | CTTTGAAAAACACGATGATAAAGCC | |
| | ACCATGGCACATGCTATGGAAAACT | |
| | CCTGGACAATCAGTGAAGAGTACCA | |
| | TATTGATGAAGAGTGGGCTTCGCT | |
| | CTGCCAAATCCACAGGAAAATCTAC | |
| | CTGATTTTTATAATGACTGGATGTT | |
| | CATTGCCAAACATCTGCCTGATCTC | |
| | ATAGAGTCTGGCCAACTTCGAGAAA | |
| | GAGTTGAGAAGTTAGACATGCTCAG | |
| | CATTGATCATCTCACAGACCACAAG | |
| | TCACAGCGCCTTGCACATCTAGTTC | |
| | TGGGATGCATCACCATGGCATATGT | |
| | GTGGGATAAAGGTCATGGAGACGTC | |
| | CGTAAGGTCTTGCCAAGAAATATTG | |
| | CTGTTCCTTACTGCCAACTCTCCAA | |
| | GAAACTGGGCCTGCCTCCTATTCTG | |
| | GTTTATGCAGACTGTGTCTTGGCAA | |
| | ACTGGAAGAAAAAGGATCCTAATAA | |
| | GCCCCTGACTTATGAGAACATGGAC | |
| | GTTTTGTTCTCCTTTCGTGATGGAG | |
| | ACTGCAGTAAAGGATTCTTCCTGGT | |
| | TTCTCTATTGGTGGAAATAGCAGCT | |
| | GCTTCTGCTATCAAAGAAATTCCTA | |
| | CTGTATTCAGGGCAATGCAATTGCG | |
| | AGAACGGGACACTCTGCTAAAGGCA | |
| | CTGTTGGAAATAGCTTCTTGCCTGG | |
| | AGAAAGCCCGTCAAGTGTTTCAGCA | |
| | AATGCACGATCACGTAAACCCAAAT | |
| | GCATTTTACAGTGTTCTTCGCATAT | |
| | ATTTGGCTGGCTGGAAAGGCAACCC | |
| | CCAGCTATCAGACGGTCTGGTGTAT | |
| | GAGGGGTTCTGGGAAGGCCCAAAGA | |
| | AGTTTGCAGGGGGCAGTGCAGCACA | |
| | AAGCAGCATCTTTCAGTGCTTTGAC | |
| | GTCCTGCTGGGCATCCAACAGAATG | |
| | CTGGTGGAGGACATGCTGCTCAGTT | |
| | CCTCCAGGACATGAGAACATATATG | |
| | CCACCAGCTCACAGGAACTTCCTGT | |
| | ACTCATTAGAGTCAAGTCCCTCAGT | |
| | CCGTGAGTTTGTCCTTTCAAAAGGT | |
| | GATGCTGGCCTGCGGGAAGCTTATG | |
| | ATGCCTGTGTGAAAGCTCTGGTCTC | |
| | CCTGAGGAGCTACCATCTGCAAATC | |
| | GTGACTAAGTACGTCCTGATTCCTG | |
| | CAAGCCAGCAGCCAAAGGAAAACAA | |
| | GACCTCTGAAGACCCTTCAAAACTG | |
| | GATGCCAAAGGAACTGGAGGCACTG | |
| | ATTTAATGGAATTCCTAAAGACTGT | |
| | GAGAAGTACAACCGAGAAATACCGT | |
| | TTGAAGGAAGGTTAAGACCTGCAGG | |
| | ACGCCACAGCTCTGATCATAATCAG | |
| | CCATACCACATTTGTAGAGGTTTA | |
| | CTTGCTTTAAAAAACCTCCCACACC | |
| | TCCCCCTGAACCTGAAACATAAAT | |
| | GAATGCAATTGTTGTTGTTAACTTG | |
| | TTTATTGCAGCTTATAATGGTTACA | |
| | AATAAAGCATAGCATCACAAATTT | |
| | CACAAATAAAGCATTTTTTTCACTG | |
| | CATTCTAGTTGTGGTTTGTCCAAAC | |
| | TCATCAATGTATCT | |
| 6 | ATGTTTGTGTTTCTGGTATTGCTGC | Codon-optimized |
| | CATTGGTCTCCAGCCAATGTGTTAA | S1 coding |
| | TCTCACGACCAGGACCCAATTGCCT | sequence |
| | CCCGCGTATACTAACTCTTTCACGA | |
| | GGGGAGTCTACTATCCTGACAAAGT | |
| | ATTTAGGTCTTCAGTGCTGCATAGT | |
| | ACACAAGACCTGTTCCTTCCGTTTT | |

-continued

| SEQ ID NO: | Sequence | Description |
|---|---|---|
| | TCAGCAACGTGACTTGGTTCCACGC | |
| | TATACACGTCTCAGGGACGAATGGA | |
| | ACAAAGCGCTTCGATAATCCGGTTT | |
| | TGCCATTTAATGATGGTGTCTATTT | |
| | CGCATCCACAGAAAAGTCCAACATT | |
| | ATCAGGGGGTGGATCTTTGGTACGA | |
| | CGCTGGATAGCAAAACACAGTCCCT | |
| | CCTTATCGTCAACAATGCCACGAAT | |
| | GTGGTGATTAAGGTTTGCGAATTTC | |
| | AATTTTGTAACGACCCTTTTCTTGG | |
| | CGTATATTATCATAAAAACAACAAG | |
| | TCCTGGATGGAAAGCGAATTCCGCG | |
| | TATACAGTTCCGCAAACAACTGTAC | |
| | ATTTGAATATGTGAGCCAACCTTTT | |
| | CTGATGGACCTGGAGGGCAAACAGG | |
| | GCAACTTTAAAAATTTGAGAGAGTT | |
| | CGTCTTCAAAAATATTGATGGATAT | |
| | TTCAAGATTTATAGTAAGCATACGC | |
| | CCATAAATCTTGTCCGGGATCTGCC | |
| | GCAGGGTTTTAGCGCTCTCGAACCC | |
| | TTGGTAGACCTCCCGATTGGTATAA | |
| | ACATCACCAGGTTTCAGACCCTTCT | |
| | TGCGTTGCACCGCAGCTATCTCACG | |
| | CCAGGCGATAGTAGTTCAGGTTGGA | |
| | CTGCCGGAGCAGCAGCCTACTACGT | |
| | AGGCTACCTTCAACCTAGAACGTTT | |
| | CTGTTGAAATATAATGAAAATGGTA | |
| | CAATCACAGACGCGGTCGACTGCGC | |
| | ACTGGACCCGCTGAGCGAAACCAAA | |
| | TGTACGCTCAAGTCCTTCACCGTAG | |
| | AGAAAGGCATCTACCAGACTTCTAA | |
| | TTTCCGAGTGCAGCCGACGGAGTCA | |
| | ATCGTGAGATTCCCTAACATAACTA | |
| | ATTTGTGTCCATTTGGCGAAGTGTT | |
| | CAATGCAACCAGATTCGCCTCCGTC | |
| | TATGCGTGGAATCGAAAAAGAATTT | |
| | CAAACTGCGTAGCGGATTATTCTGT | |
| | CTTGTACAATAGTGCCTCCTTTAGT | |
| | ACGTTCAAGTGTTATGGGGTGTCAC | |
| | CAACGAAGTTGAATGATCTTTGTTT | |
| | CACGAATGTTTACGCTGATTCATTT | |
| | GTAATACGCGGAGACGAAGTTAGAC | |
| | AAATCGCACCAGGGCAGACAGGCAA | |
| | GATCGCGGATTATAATTATAAGCTG | |
| | CCAGACGACTTCACTGGGTGCGTTA | |
| | TCGCATGGAACTCCAACAACTTGGA | |
| | TAGTAAAGTGGGCGGGAATTACAAC | |
| | TACCTGTATAGACTTTTCCGAAAGT | |
| | CCAATTTGAAGCCATTCGAAAGGGA | |
| | CATTTCTACTGAAATATATCAAGCG | |
| | GGATCAACACCTTGCAACGGAGTGG | |
| | AAGGGTTCAACTGCTACTTTCCGCT | |
| | GCAATCTTATGGGTTTCAACCGACT | |
| | AATGGAGTCGGGTATCAGCCTTACA | |
| | GAGTTGTTGTTCTTTCCTTTGAGCT | |
| | GTTGCATGCCCCGGCAACCGTATGT | |
| | GGGCCCAAGAAATCTACAAACCTCG | |
| | TTAAGAATAAATGCGTGAATTTCAA | |
| | CTTCAATGGTCTCACCGGGACGGGG | |
| | GTCCTGACCGAAAGTAACAAGAAAT | |
| | TTCTGCCCTTTCAGCAATTCGGAAG | |
| | AGACATCGCGGACACTACAGACGCC | |
| | GTTCGGGACCCGCAGACTCTCGAAA | |
| | TTCTTGACATCACGCCGTGTTCATT | |
| | CGGAGGCGTTTCCGTGATTACACCA | |
| | GGAACGAATACCAGCAGTCAAGTGG | |
| | CAGTGTTGTATCAAGATGTTAATTG | |
| | CACTGAAGTGCCTGTCGCTATCCAC | |
| | GCGGACCAGCTCACGCCTACGTGGA | |
| | GGGTGTATTCAACAGGAAGCAACGT | |
| | GTTCCAAACACGAGCGGGTTGTCTT | |
| | ATAGGGGCGGAGCACGTGAACAATA | |

43

-continued

| SEQ ID NO: | Sequence | Description |
|---|---|---|
| | GTTACGAATGTGATATACCGATAGG GGCTGGGATATGTGCGTCTTATCAA | |

44

-continued

| SEQ ID NO: | Sequence | Description |
|---|---|---|
| | ACACAGACGAATAGCCCCAGGCGCG CTCGAAGTGTGGCAAGCCAA | |

What is claimed is:

1. A recombinant polynucleotide comprising:
   a first nucleic acid molecule encoding an antigen; and
   a second nucleic acid molecule encoding an enzyme of an amino acid catabolic pathway, wherein the amino acid catabolic pathway comprises an L-tryptophan catabolic pathway or an L-arginine catabolic pathway.

2. The recombinant polynucleotide of claim 1, wherein the enzyme of the L-tryptophan catabolic pathway comprises indoleamine 2,3-dioxygenase 1, indoleamine 2,3-dioxygenase 2, tryptophan 2,3-dioxygenase or a paralogue or isoform thereof.

3. The recombinant polynucleotide of claim 1, wherein the enzyme of the L-tryptophan catabolic pathway comprises indoleamine 2,3-dioxygenase 1 or a paralogue or isoform thereof.

4. The recombinant polynucleotide of claim 1, wherein the enzyme of the L-arginine catabolic pathway comprises arginase 1, nitric oxide synthase 2, or a paralogue or isoform thereof.

5. The recombinant polynucleotide of claim 1, wherein the enzyme comprises interleukin 4-induced gene 1.

6. The recombinant polynucleotide of claim 1, wherein the antigen comprises a viral nucleoprotein.

7. The recombinant polynucleotide of claim 1, wherein the antigen comprises a secreted protein.

8. The recombinant polynucleotide of claim 1, wherein the antigen comprises an infectious disease antigen.

9. The recombinant polynucleotide of claim 8, wherein the infectious disease antigen is a bacterial antigen, a viral antigen, a fungal antigen, a protozoal antigen, a helminthic antigen, or a combination thereof.

10. The recombinant polynucleotide of claim 8, wherein the infectious disease antigen is a severe acute respiratory syndrome coronavirus (SARS-CoV) antigen, a severe acute respiratory syndrome coronavirus 2 (SARS-CoV-2) antigen, a Middle East respiratory syndrome coronavirus (MERS-CoV) antigen, a simian immunodeficiency virus (SIV) antigen, a human immunodeficiency virus (HIV) antigen, a hepatitis C virus antigen, a herpes simplex virus antigen, an Epstein-Barr virus antigen, a cytomegalovirus antigen, an influenza virus antigen, or a combination thereof.

11. The recombinant polynucleotide of claim 8, wherein the infectious disease antigen is an SIV group-specific antigen (gag) protein, an HIV gag protein, or a combination thereof.

12. The recombinant polynucleotide of claim 8, wherein the infectious disease antigen is a bacterial disease antigen from *Mycobacterium tuberculosis, Borrelia burgdorferi, Brucella abortus, Listeria monocytogenes, Chlamydia trachomatis, Coxiella burnetii, Salmonella enterica, Francisella tularensis*, or *Rickettsia* spp.

13. The recombinant polynucleotide of claim 8, wherein the infectious disease antigen is a protozoal disease antigen from *Plasmodium falciparum* or *Toxoplasma gondii*.

14. The recombinant polynucleotide of claim 1, wherein the antigen comprises a tumor-associated antigen.

15. The recombinant polynucleotide of claim 14, wherein the tumor-associated antigen is a prostate-specific antigen, melanoma-associated antigen 4 (MAGEA4), melanoma-associated antigen 10 (MAGEA10), New York esophageal squamous cell carcinoma 1 (NY-ESO-1), a neoantigen, or a combination thereof.

16. The recombinant polynucleotide of claim 1, wherein upon administration of the recombinant polynucleotide to a subject, an immune response against the antigen is induced in the subject, the immune response comprising an increased production of CD4+ memory cells compared to an administration of a recombinant polynucleotide that does not contain a nucleic acid molecule encoding the enzyme of the amino acid catabolic pathway.

17. The recombinant polynucleotide of claim 1, wherein upon administration of the recombinant polynucleotide to a subject, an immune response against the antigen is induced in the subject, the immune response comprising an increased ratio of CD4+ cells to CD8+ cells compared to an administration of a recombinant polynucleotide that does not contain a nucleic acid molecule encoding the enzyme of the amino acid catabolic pathway.

18. The recombinant polynucleotide of claim 16, wherein the immune response comprises an increased production of T memory stem cells.

19. The recombinant polynucleotide of claim 16, wherein the immune response comprises an increased production of interleukin 10 (IL-10).

* * * * *

SEQUENCE LISTING

<160> NUMBER OF SEQ ID NOS: 6

<210> SEQ ID NO 1
<211> LENGTH: 4801
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
cgtgaggctc cggtgcccgt cagtgggcag agcgcacatc gcccacagtc cccgagaagt      60 tgggggggagg gatcggcaat tgaaccggtg cctagagaag gtggcgcggg gtaaactggg     120
aaagtgatgt cgtgtactgg ctccgccttt ttcccgaggg tggggagaa ccgtatataa     180 gtgcagtagt cgccgtgaac gttcttttc gcaacgggtt tgccgccaga acacaggtaa     240
gtgccgtgtg tggttcccgc gggcctggcc tctttacggg ttatggccct tgcgtgcctt     300
gaattacttc cacctggctg cagtacgtga ttcttgatcc cgagcttcgg gttggaagtg     360
ggtgggagag ttcgaggcct tgcgcttaag gagccccttc gcctcgtgct tgagttgagg     420
cctggcctgg gcgctggggc cgccgcgtgc gaatctggtg gcaccttcgc gcctgtctcg     480
ctgctttcga taagtctcta gccatttaaa attttttgatg acctgctgcg acgctttttt     540
tctggcaaga tagtcttgta aatgcgggcc aagatctgca cactggtatt tcggtttttg     600
gggccgcggg cggcgacggg gcccgtgcgt cccagcgcac atgttcggcg aggcggggcc     660
tgcgagcgcg gccaccgaga atcggacggg ggtagtctca agctggccgg cctgctctgg     720
tgcctggcct cgcgccgccg tgtatcgccc cgccctgggc ggcaaggctg gcccggtcgg     780
caccagttgc gtgagcggaa agatggccgc ttcccggccc tgctgcaggg agctcaaaat     840
ggaggacgcg gcgctcggga gagcgggcgg gtgagtcacc cacacaaagg aaaagggcct     900
ttccgtcctc agccgtcgct tcatgtgact ccacggagta ccgggcgccg tccaggcacc     960
tcgattagtt ctcgagcttt tggagtacgt cgtctttagg ttgggggag gggtttttatg    1020 cgatggagtt tccccacact gagtgggtgg agactgaagt taggccagct tggcacttga    1080
tgtaattctc cttggaattt gcccttttg agtttggatc ttggttcatt ctcaagcctc    1140
agacagtggt tcaaagtttt tttcttccat ttcaggtgtc gtgaggaatt agctggcgcg    1200
ccttcccgcc accatgggcg tgagaaactc cgtcttgtca gggaagaaag cagatgaatt    1260
agaaaaaatt aggctacgac ccaacggaaa gaaaaagtac atgttgaagc atgtagtatg    1320
ggcagcaaat gaattagata gatttggatt agcagaaagc ctgttggaga caaagaagg    1380 atgtcaaaaa atactttcgg tcttagctcc attagtgcca acaggctcag aaaatttaaa    1440
aagcctttat aatactgtct gcgtcatctg gtgcattcac gcagaagaga aagtgaaaca    1500
cactgaggaa gcaaaacaga tagtgcagag acacctagtg gtgaaacag gaaccaccga    1560 aaccatgccg aagacctctc gaccaacagc accatctagc ggcagaggag gaaactaccc    1620
```

-continued

```
agtacagcag atcggtggca actacgtcca cctgccactg tccccgagaa ccctgaacgc    1680
ttgggtcaag ctgatcgagg agaagaagtt cggagcagaa gtagtgccag gattccaggc    1740
actgtcagaa ggttgcaccc cctacgacat caaccagatg ctgaactgcg ttggagacca    1800
tcaggcggct atgcagatca tccgtgacat catcaacgag gaggctgcag attgggactt    1860
gcagcaccca caaccagctc cacaacaagg acaacttagg gagccgtcag gatcagacat    1920
cgcaggaacc acctcctcag ttgacgaaca gatccagtgg atgtaccgtc agcagaaccc    1980
gatcccagta ggcaacatct accgtcgatg gatccagctg ggtctgcaga aatgcgtccg    2040
tatgtacaac ccgaccaaca ttctagatgt aaaacaaggg ccaaaagagc catttcagag    2100
ctatgtagac aggttctaca aaagtttaag agcagaacag acagatgcag cagtaaagaa    2160
ttggatgact caaacactgc tgattcaaaa tgctaaccca gattgcaagc tagtgctgaa    2220
ggggctgggt gtgaatccca ccctagaaga aatgctgacg gcttgtcaag gagtaggggg    2280
gccgggacag aaggctagat taatggcaga agccctgaaa gaggccctcg caccagtgcc    2340
aatccctttt gcagcagccc aacagagggg accaagaaag ccaattaagt gttggaattg    2400
tgggaaagag ggacactctg caaggcaatg cagagcccca agaagacagg gatgctggaa    2460
atgtggaaaa atggaccatg ttatggccaa atgcccagac agacaggcgg ttttttagg     2520 ccttggtcca tggggaaaga agccccgcaa tttccccatg gctcaagtgc atcaggggct    2580
gatgccaact gctcccccag aggacccagc tgtggatctg ctaaagaact acatgcagtt    2640
gggcaagcag cagagagaaa agcagagaga aagcagagag aagccttaca aggaggtgac    2700
agaggatttg ctgcacctca attctctctt tggaggagac cagtagtagc ctgcaggccc    2760
ctctccctcc cccccccta acgttactgg ccgaagccgc ttggaataag gccggtgtgc     2820
gtttgtctat atgttatttt ccaccatatt gccgtctttt ggcaatgtga gggcccggaa     2880
acctggccct gtcttcttga cgagcattcc taggggtctt tccctctcg ccaaaggaat      2940 gcaaggtctg ttgaatgtcg tgaaggaagc agttcctctg gaagcttctt gaagacaaac     3000
aacgtctgta gcgacccttt gcaggcagcg gaaccccca cctggcgaca ggtgcctctg      3060
cggccaaaag ccacgtgtat aagatacacc tgcaaaggcg gcacaacccc agtgccacgt     3120
tgtgagttgg atagttgtgg aaagagtcaa atggctctcc tcaagcgtat tcaacaaggg     3180
gctgaaggat gcccagaagg tacccccattg tatgggatct gatctggggc ctcggtgcac    3240
atgctttaca tgtgtttagt cgaggttaaa aaaacgtcta ggccccccga accacgggga     3300
cgtggttttc ctttgaaaaa cacgatgata aagccaccat ggcacatgct atggaaaact     3360
cctggacaat cagtgaagag taccatattg atgaagaagt gggcttcgct ctgccaaatc     3420
cacaggaaaa tctacctgat ttttataatg actggatgtt cattgccaaa catctgcctg     3480
atctcataga gtctggccaa cttcgagaaa gagttgagaa gttagacatg ctcagcattg     3540
atcatctcac agaccacaag tcacagcgcc ttgcacatct agttctggga tgcatcacca    3600
tggcatatgt gtgggataaa ggtcatggag acgtccgtaa ggtcttgcca agaaatattg     3660
ctgttcctta ctgccaactc tccaagaaac tgggcctgcc tcctattctg gtttatgcag    3720
actgtgtctt ggcaaactgg aagaaaaagg atcctaataa gcccctgact tatgagaaca    3780
tggacgtttt gttctccttt cgtgatggag actgcagtaa aggattcttc ctggtttctc    3840
tattggtgga aatagcagct gcttctgcta tcaaagaaat tcctactgta ttcagggcaa     3900
tgcaattgcg agaacgggac actctgctaa aggcactgtt ggaaatagct tcttgcctgg    3960
agaaagcccg tcaagtgttt cagcaaatgc acgatcacgt aaacccaaat gcattttaca    4020
```

-continued

```
gtgttcttcg catatatttg gctggctgga aaggcaaccc ccagctatca gacggtctgg      4080
tgtatgaggg gttctgggaa ggcccaaaga agtttgcagg gggcagtgca gcacaaagca      4140
gcatctttca gtgctttgac gtcctgctgg gcatccaaca gaatgctggt ggaggacatg      4200
ctgctcagtt cctccaggac atgagaacat atatgccacc agctcacagg aacttcctgt      4260
actcattaga gtcaagtccc tcagtccgtg agtttgtcct ttcaaaaggt gatgctggcc      4320
tgcgggaagc ttatgatgcc tgtgtgaaag ctctggtctc cctgaggagc taccatctgc      4380
aaatcgtgac taagtacgtc ctgattcctg caagccagca gccaaaggaa aacaagacct      4440
ctgaagaccc ttcaaaactg gatgccaaag gaactggagg cactgattta atggaattcc      4500
taaagactgt gagaagtaca accgagaaat accgtttgaa ggaaggttaa gacctgcagg      4560
acgccacagc tctgatcata atcagccata ccacatttgt agaggtttta cttgctttaa      4620
aaaacctccc acacctcccc ctgaacctga aacataaaat gaatgcaatt gttgttgtta      4680
acttgtttat tgcagcttat aatggttaca aataaagcaa tagcatcaca aatttcacaa      4740
ataaagcatt tttttcactg cattctagtt gtggtttgtc caaactcatc aatgtatctg      4800
c                                                                      4801
```

<210> SEQ ID NO 2
<211> LENGTH: 419
<212> TYPE: PRT
<213> ORGANISM: Severe acute respiratory syndrome coronavirus 2

<400> SEQUENCE: 2

```
Met Ser Asp Asn Gly Pro Gln Asn Gln Arg Asn Ala Pro Arg Ile Thr
1               5                   10                  15

Phe Gly Gly Pro Ser Asp Ser Thr Gly Ser Asn Gln Asn Gly Glu Arg
            20                  25                  30

Ser Gly Ala Arg Ser Lys Gln Arg Arg Pro Gln Gly Leu Pro Asn Asn
        35                  40                  45

Thr Ala Ser Trp Phe Thr Ala Leu Thr Gln His Gly Lys Glu Asp Leu
    50                  55                  60

Lys Phe Pro Arg Gly Gln Gly Val Pro Ile Asn Thr Asn Ser Ser Pro
65                  70                  75                  80

Asp Asp Gln Ile Gly Tyr Tyr Arg Arg Ala Thr Arg Arg Ile Arg Gly
                85                  90                  95

Gly Asp Gly Lys Met Lys Asp Leu Ser Pro Arg Trp Tyr Phe Tyr Tyr
            100                 105                 110

Leu Gly Thr Gly Pro Glu Ala Gly Leu Pro Tyr Gly Ala Asn Lys Asp
        115                 120                 125

Gly Ile Ile Trp Val Ala Thr Glu Gly Ala Leu Asn Thr Pro Lys Asp
        130                 135                 140

His Ile Gly Thr Arg Asn Pro Ala Asn Asn Ala Ala Ile Val Leu Gln
145                 150                 155                 160

Leu Pro Gln Gly Thr Thr Leu Pro Lys Gly Phe Tyr Ala Glu Gly Ser
                165                 170                 175

Arg Gly Gly Ser Gln Ala Ser Ser Arg Ser Ser Ser Arg Ser Arg Asn
            180                 185                 190

Ser Ser Arg Asn Ser Thr Pro Gly Ser Ser Arg Gly Thr Ser Pro Ala
        195                 200                 205

Arg Met Ala Gly Asn Gly Gly Asp Ala Ala Leu Ala Leu Leu Leu Leu
        210                 215                 220
```

-continued

```
Asp Arg Leu Asn Gln Leu Glu Ser Lys Met Ser Gly Lys Gly Gln Gln
225                 230                 235                 240

Gln Gln Gly Gln Thr Val Thr Lys Lys Ser Ala Ala Glu Ala Ser Lys
                245                 250                 255

Lys Pro Arg Gln Lys Arg Thr Ala Thr Lys Ala Tyr Asn Val Thr Gln
            260                 265                 270

Ala Phe Gly Arg Arg Gly Pro Glu Gln Thr Gln Gly Asn Phe Gly Asp
        275                 280                 285

Gln Glu Leu Ile Arg Gln Gly Thr Asp Tyr Lys His Trp Pro Gln Ile
    290                 295                 300

Ala Gln Phe Ala Pro Ser Ala Ser Ala Phe Phe Gly Met Ser Arg Ile
305                 310                 315                 320

Gly Met Glu Val Thr Pro Ser Gly Thr Trp Leu Thr Tyr Thr Gly Ala
                325                 330                 335

Ile Lys Leu Asp Asp Lys Asp Pro Asn Phe Lys Asp Gln Val Ile Leu
            340                 345                 350

Leu Asn Lys His Ile Asp Ala Tyr Lys Thr Phe Pro Pro Thr Glu Pro
        355                 360                 365

Lys Lys Asp Lys Lys Lys Lys Ala Asp Glu Thr Gln Ala Leu Pro Gln
    370                 375                 380

Arg Gln Lys Lys Gln Gln Thr Val Thr Leu Leu Pro Ala Ala Asp Leu
385                 390                 395                 400

Asp Asp Phe Ser Lys Gln Leu Gln Gln Ser Met Ser Ser Ala Asp Ser
                405                 410                 415

Thr Gln Ala
```

```
<210> SEQ ID NO 3
<211> LENGTH: 4526
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
cgtgaggctc cggtgcccgt cagtgggcag agcgcacatc gcccacagtc cccgagaagt      60
tggggggagg ggtcggcaat tgaaccggtg cctagagaag gtggcgcggg gtaaactggg     120
aaagtgatgt cgtgtactgg ctccgccttt ttcccgaggg tggggagaa ccgtatataa      180 gtgcagtagt cgccgtgaac gttctttttc gcaacgggtt tgccgccaga acacaggtaa     240
gtgccgtgtg tggttcccgc gggcctggcc tctttacggg ttatggccct tgcgtgcctt     300
gaattacttc cacctggctg cagtacgtga ttcttgatcc cgagcttcgg gttggaagtg     360
ggtgggagag ttcgaggcct tgcgcttaag gagcccttc gcctcgtgct tgagttgagg      420
cctggcctgg gcgctggggc cgccgcgtgc gaatctggtg gcaccttcgc gcctgtctcg     480
ctgctttcga taagtctcta gccatttaaa attttttgatg acctgctgcg acgctttttt     540
tctggcaaga tagtcttgta aatgcgggcc aagatctgca cactggtatt tcggtttttg     600
gggccgcggg cggcgacggg gcccgtgcgt cccagcgcac atgttcggcg aggcggggcc     660
tgcgagcgcg gccaccgaga tcggacggg ggtagtctca agctggccgg cctgctctgg      720
tgcctggcct cgcgccgccg tgtatcgccc cgccctgggc ggcaaggctg gcccggtcgg     780
caccagttgc gtgagcggaa agatggccgc ttcccggccc tgctgcaggg agctcaaaat     840
ggaggacgcg gcgctcggga gagcgggcgg gtgagtcacc cacacaaagg aaaagggcct     900
```

-continued

```
ttccgtcctc agccgtcgct tcatgtgact ccacggagta ccgggcgccg tccaggcacc      960
tcgattagtt ctcgagcttt tggagtacgt cgtctttagg ttgggggggag gggttttatg     1020 cgatggagtt tccccacact gagtgggtgg agactgaagt taggccagct tggcacttga     1080
tgtaattctc cttggaattt gccctttttg agtttggatc ttggttcatt ctcaagcctc     1140
agacagtggt tcaaagtttt tttcttccat ttcaggtgtc gtgaggaatt agctggcgcg     1200
ccttcccgcc accatgagcg ataacggccc ccagaatcag aggaatgcac ctaggataac     1260
atttggaggt ccgtcagaca gcactggctc caaccagaat ggcgagcggt ctggcgcgcg     1320
gtctaagcaa aggagaccac aaggtctccc gaataacacg gcctcctggt ttacagcgct     1380
cacccagcac ggtaaagagg acctgaagtt ccctaggggg caaggtgtac cgattaatac     1440
caacagctcc cccgatgacc agattggtta ttatagaaga gctacaagac gcatacgggg     1500
tggagatggg aagatgaagg acctctcccc tcggtggtat ttttattatc tgggcaccgg     1560
accggaagcc gggctcccct acggcgccaa taaggacggt ataatatggg tcgccactga     1620
gggtgccctc aataccccga aggaccacat tggcactcga aacccggcaa acaacgcagc     1680
tattgtcctg caactcccac agggtaccac gctcccgaaa ggttttttatg ccgaagggtc     1740 tcgcggggggt tcacaggcta gcagtcgaag ctcatctcgg agccgaaata gctcaaggaa     1800
ttcaacaccc ggaagctcca gaggcacaag ccctgcgcgg atggcaggga acggaggcga     1860
tgctgccctg ccctccttc tcttggatag acttaatcag ctggaatcca aaatgtcagg      1920
aaagggccag caacaacaag gtcagacagt gaccaaaaaa tccgccgcag aggccagtaa     1980
gaaacctaga cagaagcgaa ctgctacaaa ggcctataat gtaactcagg cgttcggacg     2040
gcgaggccct gaacaaaccc agggcaattt cggtgaccaa gaactcataa gacagggaac     2100
tgactacaaa cattggcccc agattgcaca atttgcccca tccgcctcag ccttcttcgg     2160
aatgtctcgc atcgggatgg aggtaacacc gagcgggacc tggctcacat acacaggtgc     2220
gataaagctc gatgacaaag atcccaattt taaagaccaa gtgatacttc ttaataagca     2280
catagacgcc tataaaacct tcccgcccac tgagccaaag aaagacaaga aaaaaaaagc     2340
ggacgagaca caagcccttc cgcaaagaca gaaaaaacag caaacggtta cattgcttcc     2400
tgcggcagac ctggatgatt tttccaaaca gcttcagcaa tctatgtcta cgcagatag      2460 tacccaggcg taatagcctg caggcccctc tccctccccc cccctaacg ttactggccg      2520 aagccgcttg gaataaggcc ggtgtgcgtt tgtctatatg ttattttcca ccatattgcc     2580
gtcttttggc aatgtgaggg cccggaaacc tggccctgtc ttcttgacga gcattcctag     2640
gggtctttcc cctctcgcca aaggaatgca aggtctgttg aatgtcgtga aggaagcagt     2700
tcctctggaa gcttcttgaa gacaaacaac gtctgtagcg accctttgca ggcagcggaa     2760 cccccccacct ggcgacaggt gcctctgcgg ccaaaagcca cgtgtataag atacacctgc     2820
aaaggcggca caaccccagt gccacgttgt gagttggata gttgtggaaa gagtcaaatg     2880
gctctcctca agcgtattca acaaggggct gaaggatgcc cagaaggtac cccattgtat     2940
gggatctgat ctggggcctc ggtgcacatg ctttacatgt gtttagtcga ggttaaaaaa     3000
acgtctaggc cccccgaacc acgggggacgt ggttttcctt tgaaaaacac gatgataaag     3060
ccaccatggc acatgctatg gaaaactcct ggacaatcag tgaagagtac catattgatg     3120
aagaagtggg cttcgctctg ccaaatccac aggaaaatct acctgatttt tataatgact     3180
ggatgttcat tgccaaacat ctgcctgatc tcatagagtc tggccaactt cgagaaagag     3240
ttgagaagtt agacatgctc agcattgatc atctcacaga ccacaagtca cagcgccttg     3300
```

-continued

```
cacatctagt tctgggatgc atcaccatgg catatgtgtg ggataaaggt catggagacg    3360
tccgtaaggt cttgccaaga aatattgctg ttccttactg ccaactctcc aagaaactgg    3420
gcctgcctcc tattctggtt tatgcagact gtgtcttggc aaactggaag aaaaaggatc    3480
ctaataagcc cctgacttat gagaacatgg acgtttgtt ctcctttcgt gatggagact    3540
gcagtaaagg attcttcctg gtttctctat tggtggaaat agcagctgct tctgctatca    3600
aagaaattcc tactgtattc agggcaatgc aattgcgaga acgggacact ctgctaaagg    3660
cactgttgga aatagcttct tgcctggaga aagcccgtca agtgtttcag caaatgcacg    3720
atcacgtaaa cccaaatgca ttttacagtg ttcttcgcat atatttggct ggctggaaag    3780 gcaacccca gctatcagac ggtctggtgt atgaggggtt ctgggaaggc ccaaagaagt    3840
ttgcaggggg cagtgcagca caaagcagca tctttcagtg ctttgacgtc ctgctgggca    3900
tccaacagaa tgctggtgga ggacatgctg ctcagttcct ccaggacatg agaacatata    3960
tgccaccagc tcacaggaac ttcctgtact cattagagtc aagtccctca gtccgtgagt    4020
ttgtcctttc aaaaggtgat gctggcctgc gggaagctta tgatgcctgt gtgaaagctc    4080
tggtctccct gaggagctac catctgcaaa tcgtgactaa gtacgtcctg attcctgcaa    4140
gccagcagcc aaaggaaaac aagacctctg aagacccttc aaaactggat gccaaaggaa    4200
ctggaggcac tgatttaatg gaattcctaa agactgtgag aagtacaacc gagaaatacc    4260
gtttgaagga aggttaagac ctgcaggacg ccacagctct gatcataatc agccatacca    4320
catttgtaga ggttttactt gctttaaaaa acctcccaca cctcccccctg aacctgaaac    4380 ataaaatgaa tgcaattgtt gttgttaact tgtttattgc agcttataat ggttacaaat    4440
aaagcaatag catcacaaat ttcacaaata aagcattttt ttcactgcat tctagttgtg    4500
gtttgtccaa actcatcaat gtatct                                        4526
```

<210> SEQ ID NO 4
<211> LENGTH: 690
<212> TYPE: PRT
<213> ORGANISM: Severe acute respiratory syndrome coronavirus 2

<400> SEQUENCE: 4

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
```

-continued

```
145              150              155              160

Ser Ser Ala Asn Asn Cys Thr Phe Glu Tyr Val Ser Gln Pro Phe Leu
            165              170              175

Met Asp Leu Glu Gly Lys Gln Gly Asn Phe Lys Asn Leu Arg Glu Phe
            180              185              190

Val Phe Lys Asn Ile Asp Gly Tyr Phe Lys Ile Tyr Ser Lys His Thr
            195              200              205

Pro Ile Asn Leu Val Arg Asp Leu Pro Gln Gly Phe Ser Ala Leu Glu
    210              215              220

Pro Leu Val Asp Leu Pro Ile Gly Ile Asn Ile Thr Arg Phe Gln Thr
225              230              235              240

Leu Leu Ala Leu His Arg Ser Tyr Leu Thr Pro Gly Asp Ser Ser Ser
            245              250              255

Gly Trp Thr Ala Gly Ala Ala Ala Tyr Tyr Val Gly Tyr Leu Gln Pro
            260              265              270

Arg Thr Phe Leu Leu Lys Tyr Asn Glu Asn Gly Thr Ile Thr Asp Ala
            275              280              285

Val Asp Cys Ala Leu Asp Pro Leu Ser Glu Thr Lys Cys Thr Leu Lys
    290              295              300

Ser Phe Thr Val Glu Lys Gly Ile Tyr Gln Thr Ser Asn Phe Arg Val
305              310              315              320

Gln Pro Thr Glu Ser Ile Val Arg Phe Pro Asn Ile Thr Asn Leu Cys
            325              330              335

Pro Phe Gly Glu Val Phe Asn Ala Thr Arg Phe Ala Ser Val Tyr Ala
            340              345              350

Trp Asn Arg Lys Arg Ile Ser Asn Cys Val Ala Asp Tyr Ser Val Leu
            355              360              365

Tyr Asn Ser Ala Ser Phe Ser Thr Phe Lys Cys Tyr Gly Val Ser Pro
    370              375              380

Thr Lys Leu Asn Asp Leu Cys Phe Thr Asn Val Tyr Ala Asp Ser Phe
385              390              395              400

Val Ile Arg Gly Asp Glu Val Arg Gln Ile Ala Pro Gly Gln Thr Gly
            405              410              415

Lys Ile Ala Asp Tyr Asn Tyr Lys Leu Pro Asp Asp Phe Thr Gly Cys
            420              425              430

Val Ile Ala Trp Asn Ser Asn Asn Leu Asp Ser Lys Val Gly Gly Asn
            435              440              445

Tyr Asn Tyr Leu Tyr Arg Leu Phe Arg Lys Ser Asn Leu Lys Pro Phe
    450              455              460

Glu Arg Asp Ile Ser Thr Glu Ile Tyr Gln Ala Gly Ser Thr Pro Cys
465              470              475              480

Asn Gly Val Glu Gly Phe Asn Cys Tyr Phe Pro Leu Gln Ser Tyr Gly
            485              490              495

Phe Gln Pro Thr Asn Gly Val Gly Tyr Gln Pro Tyr Arg Val Val Val
            500              505              510

Leu Ser Phe Glu Leu Leu His Ala Pro Ala Thr Val Cys Gly Pro Lys
            515              520              525

Lys Ser Thr Asn Leu Val Lys Asn Lys Cys Val Asn Phe Asn Phe Asn
    530              535              540

Gly Leu Thr Gly Thr Gly Val Leu Thr Glu Ser Asn Lys Lys Phe Leu
545              550              555              560

Pro Phe Gln Gln Phe Gly Arg Asp Ile Ala Asp Thr Thr Asp Ala Val
            565              570              575
```

```
Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
            610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Arg Ala Arg Ser Val Ala
            675                 680                 685

Ser Gln
    690
```

<210> SEQ ID NO 5
<211> LENGTH: 5339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
cgtgaggctc cggtgcccgt cagtgggcag agcgcacatc gcccacagtc cccgagaagt      60
tggggggagg ggtcggcaat tgaaccggtg cctagagaag gtggcgcggg gtaaactggg     120
aaagtgatgt cgtgtactgg ctccgccttt ttcccgaggg tgggggagaa ccgtatataa     180
gtgcagtagt cgccgtgaac gttctttttc gcaacgggtt tgccgccaga acacaggtaa     240
gtgccgtgtg tggttcccgc gggcctggcc tctttacggg ttatggccct tgcgtgcctt     300
gaattacttc cacctggctg cagtacgtga ttcttgatcc cgagcttcgg gttggaagtg     360
ggtgggagag ttcgaggcct tgcgcttaag gagccccttc gcctcgtgct tgagttgagg     420
cctggcctgg gcgctggggc cgccgcgtgc gaatctggtg gcaccttcgc gcctgtctcg     480
ctgctttcga taagtctcta gccatttaaa attttttgatg acctgctgcg acgcttttt     540 tctggcaaga tagtcttgta aatgcgggcc aagatctgca cactggtatt tcggtttttg     600
gggccgcggg cggcgacggg gcccgtgcgt cccagcgcac atgttcggcg aggcgggggcc     660 tgcgagcgcg gccaccgaga atcggacggg ggtagtctca agctggccgg cctgctctgg     720
tgcctggcct cgcgccgccg tgtatcgccc cgccctgggc ggcaaggctg gcccggtcgg     780
caccagttgc gtgagcggaa agatggccgc ttcccggccc tgctgcaggg agctcaaaat     840
ggaggacgcg gcgctcggga gagcgggcgg gtgagtcacc cacacaaagg aaaagggcct     900
ttccgtcctc agccgtcgct tcatgtgact ccacggagta ccgggcgccg tccaggcacc     960
tcgattagtt ctcgagcttt tggagtacgt cgtctttagg ttggggggag gggttttatg    1020
cgatggagtt tccccacact gagtgggtgg agactgaagt taggccagct tggcacttga    1080
tgtaattctc cttggaattt gcccttttttg agtttggatc ttggttcatt ctcaagcctc    1140
agacagtggt tcaaagtttt tttcttccat ttcaggtgtc gtgaggaatt agctggcgcg    1200
ccttcccgcc accatgtttg tgtttctggt attgctgcca ttggtctcca gccaatgtgt    1260
taatctcacg accaggaccc aattgcctcc cgcgtatact aactctttca cgaggggagt    1320
```

-continued

```
ctactatcct gacaaagtat ttaggtcttc agtgctgcat agtacacaag acctgttcct    1380 tccgttttc agcaacgtga cttggttcca cgctatacac gtctcaggga cgaatggaac     1440
aaagcgcttc gataatccgg ttttgccatt taatgatggt gtctatttcg catccacaga    1500
aaagtccaac attatcaggg ggtggatctt tggtacgacg ctggatagca aaacacagtc    1560
cctccttatc gtcaacaatg ccacgaatgt ggtgattaag gtttgcgaat ttcaattttg    1620
taacgaccct tttcttggcg tatattatca taaaaacaac aagtcctgga tggaaagcga    1680
attccgcgta tacagttccg caaacaactg tacatttgaa tatgtgagcc aacctttct     1740 gatggacctg gagggcaaac agggcaactt taaaaatttg agagagttcg tcttcaaaaa    1800
tattgatgga tatttcaaga tttatagtaa gcatacgccc ataaatcttg tccgggatct    1860
gccgcagggt tttagcgctc tcgaaccctt ggtagacctc ccgattggta taaacatcac    1920
caggtttcag acccttcttg cgttgcaccg cagctatctc acgccaggcg atagtagttc    1980
aggttggact gccggagcag cagcctacta cgtaggctac cttcaaccta gaacgtttct    2040
gttgaaatat aatgaaaatg gtacaatcac agacgcggtc gactgcgcac tggacccgct    2100
gagcgaaacc aaatgtacgc tcaagtcctt caccgtagag aaaggcatct accagacttc    2160
taatttccga gtgcagccga cggagtcaat cgtgagattc cctaacataa ctaatttgtg    2220
tccatttggc gaagtgttca atgcaaccag attcgcctcc gtctatgcgt ggaatcgaaa    2280
aagaatttca aactgcgtag cggattattc tgtcttgtac aatagtgcct cctttagtac    2340
gttcaagtgt tatggggtgt caccaacgaa gttgaatgat ctttgtttca cgaatgttta    2400
cgctgattca tttgtaatac gcggagacga agttagacaa atcgcaccag ggcagacagg    2460
caagatcgcg gattataatt ataagctgcc agacgacttc actgggtgcg ttatcgcatg    2520
gaactccaac aacttggata gtaaagtggg cgggaattac aactacctgt atagacttt     2580 ccgaaagtcc aatttgaagc cattcgaaag ggacatttct actgaaatat atcaagcggg    2640
atcaacacct tgcaacggag tggaagggtt caactgctac tttccgctgc aatcttatgg    2700
gtttcaaccg actaatggag tcgggtatca gccttacaga gttgttgttc tttcctttga    2760
gctgttgcat gcccccggcaa ccgtatgtgg gcccaagaaa tctacaaacc tcgttaagaa    2820
taaatgcgtg aatttcaact tcaatggtct caccgggacg ggggtcctga ccgaaagtaa    2880
caagaaattt ctgcccttc agcaattcgg aagagacatc gcggacacta cagacgccgt     2940
tcgggacccg cagactctcg aaattcttga catcacgccg tgttcattcg gaggcgtttc    3000
cgtgattaca ccaggaacga ataccagcaa tcaagtggca gtgttgtatc aagatgttaa    3060
ttgcactgaa gtgcctgtcg ctatccacgc ggaccagctc acgcctacgt ggagggtgta    3120
ttcaacagga agcaacgtgt tccaaacacg agcgggttgt cttataggggg cggagcacgt    3180 gaacaatagt tacgaatgtg atataccgat aggggctggg atatgtgcgt cttatcaaac    3240
acagacgaat agcccccaggc gcgctcgaag tgtggcaagc caatagtagc ctgcaggccc    3300
ctctccctcc ccccccccta acgttactgg ccgaagccgc ttggaataag gccggtgtgc    3360
gtttgtctat atgttatttt ccaccatatt gccgtctttt ggcaatgtga gggcccggaa    3420
acctggccct gtcttcttga cgagcattcc taggggtctt tccctctcg ccaaaggaat      3480 gcaaggtctg ttgaatgtcg tgaaggaagc agttcctctg gaagcttctt gaagacaaac    3540
aacgtctgta gcgaccctt gcaggcagcg gaaccccca cctggcgaca ggtgcctctg       3600
cggccaaaag ccacgtgtat aagatacacc tgcaaaggcg gcacaacccc agtgccacgt    3660
```

```
tgtgagttgg atagttgtgg aaagagtcaa atggctctcc tcaagcgtat tcaacaaggg    3720
gctgaaggat gcccagaagg tacccccattg tatgggatct gatctggggc ctcggtgcac   3780
atgctttaca tgtgtttagt cgaggttaaa aaaacgtcta ggccccccga accacgggga    3840
cgtggttttc ctttgaaaaa cacgatgata aagccaccat ggcacatgct atggaaaact    3900
cctggacaat cagtgaagag taccatattg atgaagaagt gggcttcgct ctgccaaatc    3960
cacaggaaaa tctacctgat ttttataatg actggatgtt cattgccaaa catctgcctg    4020
atctcataga gtctggccaa cttcgagaaa gagttgagaa gttagacatg ctcagcattg    4080
atcatctcac agaccacaag tcacagcgcc ttgcacatct agttctggga tgcatcacca    4140
tggcatatgt gtgggataaa ggtcatggag acgtccgtaa ggtcttgcca agaaatattg    4200
ctgttcctta ctgccaactc tccaagaaac tgggcctgcc tcctattctg gtttatgcag    4260
actgtgtctt ggcaaactgg aagaaaaagg atcctaataa gcccctgact tatgagaaca    4320
tggacgtttt gttctccttt cgtgatggag actgcagtaa aggattcttc ctggtttctc    4380
tattggtgga aatagcagct gcttctgcta tcaaagaaat tcctactgta ttcagggcaa    4440
tgcaattgcg agaacgggac actctgctaa aggcactgtt ggaaatagct tcttgcctgg    4500
agaaagcccg tcaagtgttt cagcaaatgc acgatcacgt aaacccaaat gcattttaca    4560
gtgttcttcg catatatttg gctggctgga aaggcaaccc ccagctatca gacggtctgg    4620
tgtatgaggg gttctgggaa ggcccaaaga agtttgcagg gggcagtgca gcacaaagca    4680
gcatctttca gtgctttgac gtcctgctgg gcatccaaca gaatgctggt ggaggacatg    4740
ctgctcagtt cctccaggac atgagaacat atatgccacc agctcacagg aacttcctgt    4800
actcattaga gtcaagtccc tcagtccgtg agtttgtcct ttcaaaaggt gatgctggcc    4860
tgcgggaagc ttatgatgcc tgtgtgaaag ctctggtctc cctgaggagc taccatctgc    4920
aaatcgtgac taagtacgtc ctgattcctg caagccagca gccaaaggaa aacaagacct    4980
ctgaagaccc ttcaaaactg gatgccaaag gaactggagg cactgattta atggaattcc    5040
taaagactgt gagaagtaca accgagaaat accgtttgaa ggaaggttaa gacctgcagg    5100
acgccacagc tctgatcata atcagccata ccacatttgt agaggtttta cttgctttaa    5160
aaaacctccc acacctcccc ctgaacctga aacataaaat gaatgcaatt gttgttgtta    5220
acttgtttat tgcagcttat aatggttaca aataaagcaa tagcatcaca aatttcacaa    5280
ataaagcatt tttttcactg cattctagtt gtggtttgtc caaactcatc aatgtatct     5339
```

```
<210> SEQ ID NO 6
<211> LENGTH: 2070
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
atgtttgtgt ttctggtatt gctgccattg gtctccagcc aatgtgttaa tctcacgacc      60
aggacccaat tgcctcccgc gtatactaac tctttcacga ggggagtcta ctatcctgac     120
aaagtattta ggtcttcagt gctgcatagt acacaagacc tgttccttcc gttttttcagc    180 aacgtgactt ggttccacgc tatacacgtc tcagggacga atggaacaaa gcgcttcgat     240
aatccggttt tgccatttaa tgatggtgtc tatttcgcat ccacagaaaa gtccaacatt     300 atcaggggggt ggatctttgg tacgacgctg gatagcaaaa cacagtccct ccttatcgtc    360
```

-continued

```
aacaatgcca cgaatgtggt gattaaggtt tgcgaatttc aattttgtaa cgaccctttt    420
cttggcgtat attatcataa aaacaacaag tcctggatgg aaagcgaatt ccgcgtatac    480
agttccgcaa acaactgtac atttgaatat gtgagccaac cttttctgat ggacctggag    540
ggcaaacagg gcaactttaa aaatttgaga gagttcgtct tcaaaaatat tgatggatat    600
ttcaagattt atagtaagca tacgcccata aatcttgtcc gggatctgcc gcagggtttt    660
agcgctctcg aacccttggt agacctcccg attggtataa acatcaccag gtttcagacc    720
cttcttgcgt tgcaccgcag ctatctcacg ccaggcgata gtagttcagg ttggactgcc    780
ggagcagcag cctactacgt aggctacctt caacctagaa cgtttctgtt gaaatataat    840
gaaaatggta caatcacaga cgcggtcgac tgcgcactgg acccgctgag cgaaaccaaa    900
tgtacgctca agtccttcac cgtagagaaa ggcatctacc agacttctaa tttccgagtg    960
cagccgacgg agtcaatcgt gagattccct aacataacta atttgtgtcc atttggcgaa   1020
gtgttcaatg caaccagatt cgcctccgtc tatgcgtgga atcgaaaaag aatttcaaac   1080
tgcgtagcgg attattctgt cttgtacaat agtgcctcct ttagtacgtt caagtgttat   1140
ggggtgtcac caacgaagtt gaatgatctt tgtttcacga atgtttacgc tgattcattt   1200
gtaatacgcg gagacgaagt tagacaaatc gcaccagggc agacaggcaa gatcgcggat   1260
tataattata agctgccaga cgacttcact gggtgcgtta tcgcatggaa ctccaacaac   1320
ttggatagta aagtgggcgg gaattacaac tacctgtata gacttttccg aaagtccaat   1380
ttgaagccat tcgaaaggga catttctact gaaatatatc aagcgggatc aacaccttgc   1440 aacgagtgg aagggttcaa ctgctacttt ccgctgcaat cttatgggtt tcaaccgact   1500
aatggagtcg ggtatcagcc ttacagagtt gttgttcttt cctttgagct gttgcatgcc   1560
ccggcaaccg tatgtgggcc caagaaatct acaaacctcg ttaagaataa atgcgtgaat   1620
ttcaacttca atggtctcac cgggacgggg gtcctgaccg aaagtaacaa gaaatttctg   1680
ccctttcagc aattcggaag agacatcgcg gacactacag acgccgttcg ggacccgcag   1740
actctcgaaa ttcttgacat cacgccgtgt tcattcggag gcgtttccgt gattacacca   1800
ggaacgaata ccagcaatca agtggcagtg ttgtatcaag atgttaattg cactgaagtg   1860
cctgtcgcta tccacgcgga ccagctcacg cctacgtgga gggtgtattc aacaggaagc   1920
aacgtgttcc aaaacgagc gggttgtctt ataggggcgg agcacgtgaa caatagttac   1980
gaatgtgata taccgatagg ggctgggata tgtgcgtctt atcaaacaca gacgaatagc   2040
cccaggcgcg ctcgaagtgt ggcaagccaa                                     2070
```